US012024507B2

(12) United States Patent
Reeves et al.

(10) Patent No.: US 12,024,507 B2
(45) Date of Patent: Jul. 2, 2024

(54) COMPOUNDS AS GLP-1R AGONISTS

(71) Applicant: Terns Pharmaceuticals, Inc.

(72) Inventors: Corey Reeves, Foster City, CA (US); F. Anthony Romero, Redwood City, CA (US); Christopher T. Jones, Foster City, CA (US); Martijn Fenaux, San Mateo, CA (US); Gary W. Luehr, Foster City, CA (US)

(73) Assignee: Terns Pharmaceuticals, Inc., Foster City, CA (US)

( * ) Notice: Subject to any disclaimer, the term of this patent is extended or adjusted under 35 U.S.C. 154(b) by 0 days.

(21) Appl. No.: 17/973,225

(22) Filed: Oct. 25, 2022

(65) Prior Publication Data

US 2023/0159512 A1     May 25, 2023

Related U.S. Application Data

(60) Provisional application No. 63/263,003, filed on Oct. 25, 2021.

(51) Int. Cl.
| | | |
|---|---|---|
| *C07D 413/14* | (2006.01) | |
| *A61K 9/00* | (2006.01) | |
| *A61P 1/16* | (2006.01) | |
| *C07D 417/14* | (2006.01) | |

(52) U.S. Cl.
CPC .......... *C07D 413/14* (2013.01); *A61K 9/0019* (2013.01); *A61P 1/16* (2018.01); *C07D 417/14* (2013.01)

(58) Field of Classification Search
CPC ....... C07D 413/14; C07D 417/14; A61P 1/16; A61K 9/0019
USPC .......................................................... 514/322
See application file for complete search history.

(56) References Cited

U.S. PATENT DOCUMENTS

| | | | |
|---|---|---|---|
| 5,665,732 A | 9/1997 | Baker et al. | |
| 5,714,498 A | 2/1998 | Kulagowski et al. | |
| 5,763,263 A | 6/1998 | Dehlinger | |
| 5,780,475 A | 7/1998 | Baker et al. | |
| 10,208,019 B2 | 2/2019 | Aspnes et al. | |
| 11,512,070 B2 | 11/2022 | Aspnes et al. | |
| 2003/0162790 A1 | 8/2003 | Cowart et al. | |
| 2003/0176438 A1 | 9/2003 | Arienti et al. | |
| 2004/0127504 A1 | 7/2004 | Cowart et al. | |
| 2005/0004114 A1 | 1/2005 | Whitehouse et al. | |
| 2007/0244126 A1 | 10/2007 | Edwards et al. | |
| 2008/0280933 A1 | 11/2008 | Efremov et al. | |
| 2012/0028959 A1 | 2/2012 | Thunuguntla et al. | |
| 2018/0170908 A1 | 6/2018 | Aspnes et al. | |
| 2019/0119255 A1 | 4/2019 | Aspnes et al. | |
| 2020/0071306 A1 | 3/2020 | Esler et al. | |
| 2022/0089578 A1 | 3/2022 | Romero et al. | |
| 2022/0348564 A1 * | 11/2022 | Ren .................. | C07D 405/14 |
| 2023/0124938 A1 | 4/2023 | Aspnes et al. | |
| 2023/0150998 A1 | 5/2023 | Reeves et al. | |
| 2023/0322744 A1 | 10/2023 | Romero et al. | |
| 2023/0322758 A1 | 10/2023 | Reeves et al. | |

FOREIGN PATENT DOCUMENTS

| | | |
|---|---|---|
| CN | 113493447 A | 10/2021 |
| EP | 3555064 B1 | 11/2022 |
| TW | 202128659 A | 8/2021 |
| WO | WO-2010114957 A1 | 10/2010 |
| WO | WO-2011143365 A1 | 11/2011 |
| WO | WO-2015166398 A1 | 11/2015 |
| WO | WO-2018109607 A1 | 6/2018 |
| WO | WO-2019239319 A1 | 12/2019 |
| WO | WO-2019239371 A1 | 12/2019 |
| WO | WO-2020103815 A1 | 5/2020 |
| WO | WO-2020207474 A1 | 10/2020 |
| WO | WO-2020263695 A1 | 12/2020 |
| WO | WO-2021018023 A1 | 2/2021 |
| WO | WO-2021081207 A1 | 4/2021 |
| WO | WO-2021096284 A1 | 5/2021 |
| WO | WO-2021096304 A1 | 5/2021 |
| WO | WO-2021112538 A1 | 6/2021 |
| WO | WO-2021116874 A1 | 6/2021 |
| WO | WO-2021154796 A1 | 8/2021 |
| WO | WO-2021160127 A1 | 8/2021 |
| WO | WO-2021187886 A1 | 9/2021 |
| WO | WO-2021197464 A1 | 10/2021 |
| WO | WO-2021219019 A1 | 11/2021 |
| WO | WO-2021242817 A1 | 12/2021 |

(Continued)

OTHER PUBLICATIONS

International Preliminary Report on Patentability, dated Mar. 2, 2023, for International Application No. PCT/US2021/047015, 8 pages.

International Search Report and Written Opinion for International Application No. PCT/US2021/047015, dated Jan. 13, 2022, 11 Pages.

International Search Report and Written Opinion for International Application No. PCT/US2022/047687 dated Feb. 16, 2023, 13 pages.

International Search Report and Written Opinion, dated Apr. 28, 2023, for PCT International Application No. PCT/US2023/013700 (11 total pages).

(Continued)

*Primary Examiner* — Kahsay Habte

(74) *Attorney, Agent, or Firm* — COOLEY LLP; Heidi A. Erlacher; Eric A. Owens

(57) ABSTRACT

The present application provides compounds that may be used as a glucagon-like peptide-1 receptors (GLP-1R) agonist, or pharmaceutically acceptable salts thereof. Also provided are pharmaceutical compositions containing such compounds, or pharmaceutically acceptable salts thereof. Methods of preparing these compounds and compositions, and methods of using these compounds and compositions to treat or prevent a disease or a condition mediated by GLP-1R, are also provided.

32 Claims, No Drawings

(56) References Cited

FOREIGN PATENT DOCUMENTS

| WO | WO-2021244391 A1 | 12/2021 |
|---|---|---|
| WO | WO-2021244645 A1 | 12/2021 |
| WO | WO-2021249492 A1 | 12/2021 |
| WO | WO-2021254470 A1 | 12/2021 |
| WO | WO-2021259309 A1 | 12/2021 |
| WO | WO-2022007979 A1 | 1/2022 |
| WO | WO-2022028572 A1 | 2/2022 |
| WO | WO-2022040600 A1 | 2/2022 |
| WO | WO-2022042691 A1 | 3/2022 |
| WO | WO-2022048665 A1 | 3/2022 |
| WO | WO-2022052958 A1 | 3/2022 |
| WO | WO-2022078152 A1 | 4/2022 |
| WO | WO-2022078352 A1 | 4/2022 |
| WO | WO-2022078380 A1 | 4/2022 |
| WO | WO-2022078407 A1 | 4/2022 |
| WO | WO-2022109182 A1 | 5/2022 |
| WO | WO-2022111624 A1 | 6/2022 |
| WO | WO-2022116693 A1 | 6/2022 |
| WO | WO-2022192428 A1 | 9/2022 |
| WO | WO-2022192430 A1 | 9/2022 |
| WO | WO-2022199661 A1 | 9/2022 |
| WO | WO-2022202864 A1 | 9/2022 |
| WO | WO-2022216094 A1 | 10/2022 |
| WO | WO-2022219495 A1 | 10/2022 |
| WO | WO-2022225941 A1 | 10/2022 |
| WO | WO-2022235717 A1 | 11/2022 |
| WO | WO-2022246019 A1 | 11/2022 |
| WO | WO-2022268152 A1 | 12/2022 |
| WO | WO-2023000834 A1 | 1/2023 |
| WO | WO-2023001237 A1 | 1/2023 |
| WO | WO-2023029380 A1 | 3/2023 |
| WO | WO-2023031741 A1 | 3/2023 |
| WO | WO-2023049518 A1 | 3/2023 |
| WO | WO-2023057414 A1 | 4/2023 |
| WO | WO-2023057427 A1 | 4/2023 |
| WO | WO-2023057429 A1 | 4/2023 |
| WO | WO-2023066356 A1 | 4/2023 |
| WO | WO-2023076237 A1 | 5/2023 |
| WO | WO-2023103310 A1 | 6/2023 |
| WO | WO-2023111145 A1 | 6/2023 |
| WO | WO-2023164050 A1 | 8/2023 |

OTHER PUBLICATIONS

International Search Report and Written Opinion, dated Dec. 5, 2022, for International Application No. PCT/US2022/044915 (13 total pages).

Invitation to Pay Additional Fees and, Where Applicable, Protest Fee, dated Oct. 25, 2021, for International Application No. PCT/US2021/047015 (2 total pages).

1H-Benzimidazole-6-carboxylic acid, 2-[[4-[(2S)-2-(5-chloro-2-pyridinyl)-2-methyl-1,3-benzodioxol-4-yl]-1-piperidinyl]methyl]-1-[(2S)-2-oxetanylmethyl]-, Chemical Book, 2017, 2 pages.

Balaban, A. T., et al., Aromaticity as a Cornerstone of Heterocyclic Chemistry, Chem. Rev. 2004, 104, 2777-2812.

Beker, W, et al., "Reactivity Patterns of Imidazole, Oxazole, and Thiazole as Reflected by the Polarization Justified Fukui Functions," J. Phys. Chem. A 2013, 117, 1596-1600.

Beulah, K., et al., "Design, Synthesis and Biological Evaluation of Benzimidazole-pyridine-Piperidine Hybrids as a New Class of Potent Antimicrobial Agents," Letters in Drug Design & Discovery, 2015, vol. 12, No. 1, pp. 38-45.

Davies, D. T., Aromatic Heterocyclic Chemistry, Chapters 3 and 4, Oxford University Press 1992, 21 pages.

Dorwald, Side Reactions in Organic Synthesis. Wiley-VCH, 1-16 (2005).

Griffith, D. A., et al., "A Small-Molecule Oral Agonist of the Human Glucagon-like Peptide-1 Receptor," Journal of Medicinal Chemistry, 2022, 65, pp. 8208-8226.

Haberhauer, G., et al., "Structural Investigation of Westiellamide Analogues," Tetrahedron 2008, 64, 1853-1859.

Horner, K. E., et al., "Shielding in and around Oxazole, Imidazole, and Thiazole: How Does the Second Heteroatom Affect Aromaticity and Bonding?," J. Org. Chem. 2015, 80, 7150-7157.

Kaspady, M., et al., "Synthesis, Antibacterial Activity of 2,4-Disubstituted Oxazoles and Thiazoles as Bioisosteres," Letters in Drug Design & Discovery, 2009, 6, pp. 21-28.

Ognyaov, V. I., et al., "Design of Potent, Orally Available Antagonists of the Transient Receptor Potential Vanilloid 1. Structure-Activity Relationships of 2-Piperazin-1-yl-1H-benzimidazoles," J. Med Chem, 2006, vol. 49, No. 12, pp. 3719-3742.

Pathway: HSA04911, Insulin secretion—*Homo sapiens* (human), KEGG, Jun. 6, 2017, 6 pages.

Saxena, A.R., et al., "Efficacy and Safety of Oral Small Molecule Glucagon-Like Peptide 1 Receptor Agonist Danuglipron for Glycemic Control Among Patients With Type 2 Diabetes: A Randomized Clinical Trial," JAMA Network Open, May 1, 2023, vol. 6(5), pp. 2314493.

Shaffer, A. A, et al., "Comparison of Computational Methods Applied to Oxazole, Thiazole, and Other Heterocyclic Compounds," Journal of Computational Chemistry, vol. 14, No. 1, pp. 75-88 (1993).

Sharma, M. C., "QSAR studies of novel 1-(4-methoxyphenethyl)-1H-benzimidazole-5-carboxylic acid derivatives and their precursors as antileukaemic agents," Journal of Taibah University for Science, 2016, vol. 10, pp. 122-130.

\* cited by examiner

COMPOUNDS AS GLP-1R AGONISTS

CROSS REFERENCE TO RELATED APPLICATIONS

This application claims priority to and the benefit of U.S. Provisional Patent Application No. 63/263,003, filed Oct. 25, 2021, the disclosure of which is hereby incorporated by reference in its entirety for all purposes.

BACKGROUND

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. Use of Antidiabetic Drugs in the U.S., 2003-2012, Diabetes Care 2014, 37, 1367-1374). One of them is glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Marketed GLP-1R agonists are peptides administered by subcutaneous injection. Liraglutide is additionally approved for the treatment of obesity.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier et al. Biodrugs. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. Diabetes. 2001. 50; 609-613).

Holst (Physiol. Rev. 2007, 87, 1409) and Meier (Nat. Rev. Endocrinol. 2012, 8, 728) describe that GLP-1 receptor agonists, such as liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need of developing GLP-1 receptor agonists for an easily-administered prevention and/or treatment for cardiometabolic and associated diseases.

SUMMARY

Disclosed are compounds that can be used as glucagon-like peptide-1 receptor (GLP-1R) agonists, compositions containing these compounds and methods for treating diseases and/or conditions mediated by GLP-1R.

In one aspect, provided is a compound of Formula (I) (including subformulae thereof) or selected from the compounds listed in Table 1, or a pharmaceutically acceptable salt thereof, as detailed herein.

Further provided is a pharmaceutical composition comprising a compound of Formula (I) (including subformulae thereof) or selected from the compounds listed in Table 1, or a pharmaceutically acceptable salt thereof, and a pharmaceutically acceptable carrier or excipient.

In another aspect, provided is a method of treating a disease or a condition mediated by GLP-1R in a subject in need thereof comprises administering to the subject a therapeutically effective amount of a compound of Formula (I) (including subformulae thereof) or selected from the compounds listed in Table 1, or a pharmaceutically acceptable salt thereof. In some embodiments, the disease or the condition is a cardiometabolic disease. In some embodiments, the disease or the condition is diabetes. In some embodiments, the disease or the condition is a liver disease.

Also provided is a compound of Formula (I) (including subformulae thereof) or selected from the compounds listed in Table 1, or a pharmaceutically acceptable salt thereof, as detailed herein, for the treatment.

Also provided is use of a compound of Formula (I) (including subformulae thereof) or selected from the compounds listed in Table 1, or a pharmaceutically acceptable salt thereof, as detailed herein, in the manufacture of a medicament for the treatment.

Further provided is a kit comprising a compound of Formula (I) (including subformulae thereof) or selected from the compounds listed in Table 1, or a pharmaceutically acceptable salt thereof. In some embodiments, the kit comprises instructions for use according to a method described herein.

In yet another aspect, provided is a method of making a compound of Formula (I) (including subformulae thereof) or selected from the compounds listed in Table 1, or a pharmaceutically acceptable salt thereof. Also provided are compound intermediates useful in synthesis of a compound of Formula (I) (including subformulae thereof) or selected from the compounds listed in Table 1, or a pharmaceutically acceptable salt thereof.

In one aspect, the present disclosure provides a compound of formula (I):

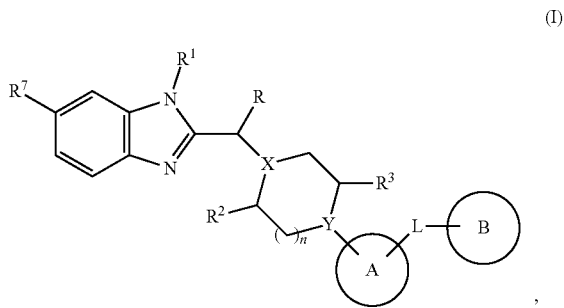

or a pharmaceutically acceptable salt thereof, wherein:
X is N or CH;
Y is N or CR$^4$;
n is 0 or 1;
R is hydrogen;
R$^1$ is —C$_1$-C$_6$ alkylene-R$^5$;
R$^2$ is hydrogen, oxo, or C$_1$-C$_6$ alkyl;
R$^3$ is hydrogen, oxo, or C$_1$-C$_6$ alkyl and R$^4$ is hydrogen, OH or C$_1$-C$_6$ alkyl,
or R$^3$ and R$^4$ are taken together with the carbon atoms to which they are attached to form C$_3$-C$_6$ cycloalkyl optionally substituted by halo or C$_1$-C$_3$ alkyl;
R$^5$ is 3- to 6-membered heterocyclyl or 5- to 6-membered heteroaryl, wherein the 3- to 6-membered heterocyclyl or 5- to 6-membered heteroaryl of R$^5$ is independently optionally substituted by halo, C$_1$-C$_6$ alkyl, C$_1$-C$_6$ alkoxy, C$_1$-C$_6$ alkenyl, or C$_1$-C$_6$ haloalkyl;
R$^7$ is selected from the group consisting of

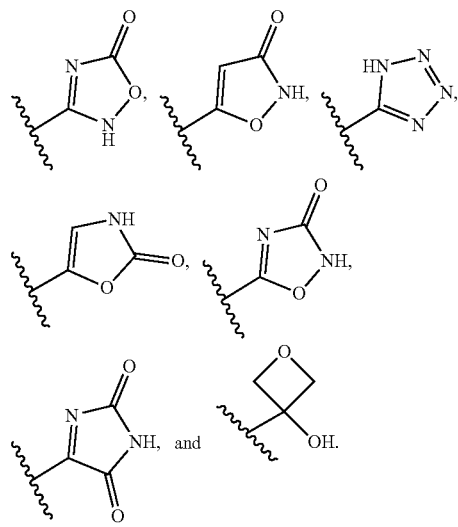

or R$^7$ is —C(O)NH—R$^8$, wherein R$^8$ is hydrogen, —OH, —S(O)$_2$—C$_1$-C$_6$ alkyl, or —C$_1$-C$_6$ alkyl optionally substituted by halo;
Ring A is 5- to 12-membered heterocyclyl, 5- to 12-membered heteroaryl, or C$_6$-C$_{14}$ aryl, each of which is independently optionally substituted by halo, oxo, —CN, C$_3$-C$_6$ cycloalkyl, or C$_1$-C$_6$ alkyl optionally substituted by halo or OH;
L is a bond, —O—, C$_1$-C$_6$ alkylene, *—O—C$_1$-C$_6$ alkylene-**, *—C$_1$-C$_6$ alkylene-O—**, or *—NR$^6$—C$_1$-C$_6$ alkylene-**, wherein:
* represents the point of attachment to ring A and ** represents the point of attachment to ring B;
when L is *—O—C$_1$-C$_6$ alkylene-**, the C$_1$-C$_6$ alkylene is optionally substituted by R$^L$, wherein each R$^L$ is independently C$_1$-C$_6$ alkyl or halo, or two R$^L$ are taken together with the carbon atom or atoms to which they are attached to form C$_3$-C$_6$ cycloalkyl or 3- to 6-membered heterocyclyl; and
when L is C$_1$-C$_6$ alkylene, the C$_1$-C$_6$ alkylene is optionally substituted by R$^{L1}$, wherein each R$^{L1}$ is independently halo, OH, oxo, or C$_1$-C$_6$ alkyl, or two R$^{L1}$ are taken together with the carbon atom or atoms to which they are attached to form C$_3$-C$_6$ cycloalkyl or 3- to 6-membered heterocyclyl;

R$^6$ is hydrogen or C$_1$-C$_6$ alkyl; and
Ring B is C$_3$-C$_{10}$ cycloalkyl, C$_6$-C$_{14}$ aryl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —C(O)CH$_3$, —C(O)NH$_2$, —S(O)$_2$CH$_3$, cyclopropyl, and phenyl,
with the proviso that:
when R$^7$ is —C(O)NH—R$^8$, R$^1$ is

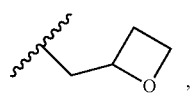

X is N, Y is CH, n is 1, R$^2$ and R$^3$ are each hydrogen, ring A is 6-membered heteroaryl, and L is *—OCH$_2$—**, then ring B is not

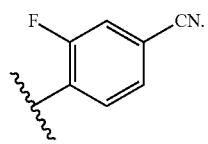 [SMILES: *c1ccc(C#N)cc1F]

In some embodiments, the compound is of Formula Ia:

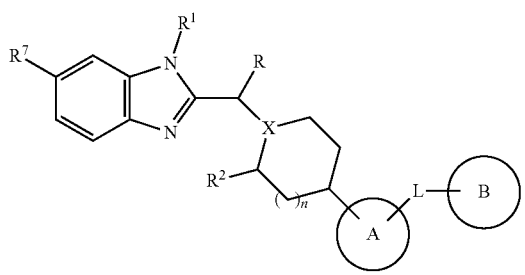

(Ia)

or a pharmaceutically acceptable salt thereof.
In some embodiments, the compound is of Formula Ib:

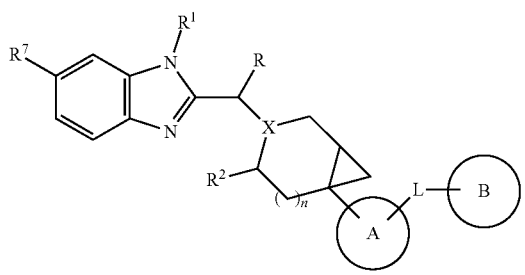

(Ib)

or a pharmaceutically acceptable salt thereof.
In some embodiments:
n is 1;
X is N;
R$^2$ is hydrogen;
R$^5$ is an optionally substituted five-membered heteroaryl comprising one or two heteroatoms selected from the group consist of oxygen, nitrogen, and sulfur, or an optionally substituted four-membered heterocycle comprising one oxygen atom;

$R^7$ is

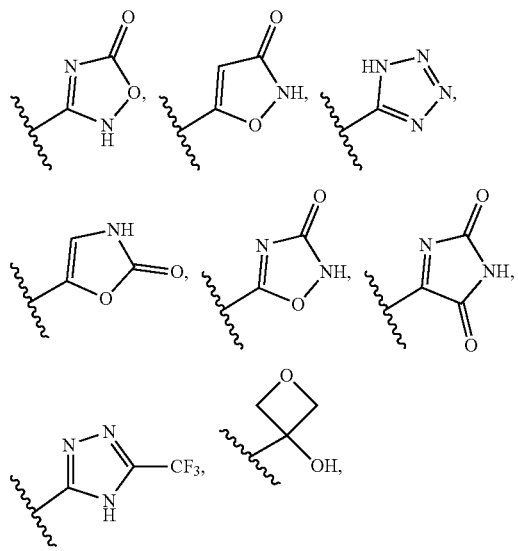

—C(O)NHCH$_3$, —C(O)NH$_2$, C(O)NHCH$_2$CF$_3$, C(O)NHS(O)$_2$CH$_3$, or C(O)NHOH.

Ring A is an optionally substituted 6-9-membered heteroaryl;

L is a bond or *—O—CH$_2$—**; and

Ring B is phenyl optionally substituted by one to three substituents independently selected from the group consisting of halo and cyano.

In some embodiments, $R^1$ is —CH$_2$—$R^5$.

In some embodiments, $R^5$ is 4-membered heterocyclyl comprising one oxygen atom optionally substituted by halo, C$_1$-C$_6$ alkyl, C$_1$-C$_6$ alkoxy, C$_1$-C$_6$ alkenyl, or C$_1$-C$_6$ haloalkyl. In some embodiments, $R^5$ is

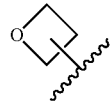

optionally substituted by halo, C$_1$-C$_6$ alkyl, C$_1$-C$_6$ alkoxy, C$_1$-C$_6$ alkenyl, or C$_1$-C$_6$ haloalkyl. In some embodiments, $R^5$ is

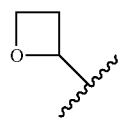

In some embodiments, $R^5$ is 5-membered heteroaryl optionally substituted by halo, C$_1$-C$_6$ alkyl, C$_1$-C$_6$ alkoxy, C$_1$-C$_6$ alkenyl, or C$_1$-C$_6$ haloalkyl. In some embodiments, $R^5$ is

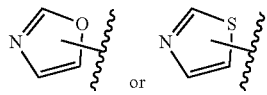

optionally substituted by halo, C$_1$-C$_6$ alkyl, C$_1$-C$_6$ alkoxy, C$_1$-C$_6$ alkenyl, or C$_1$-C$_6$ haloalkyl. In some embodiments, $R^5$ is

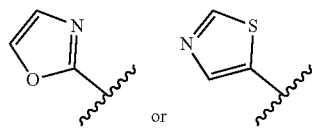 [SMILES: *c1ncco1 ; *c1cncs1]

optionally substituted by halo C$_1$-C$_6$ alkyl, C$_1$-C$_6$ alkoxy, C$_1$-C$_6$ alkenyl, or C$_1$-C$_6$ haloalkyl. In some embodiments, $R^5$ is

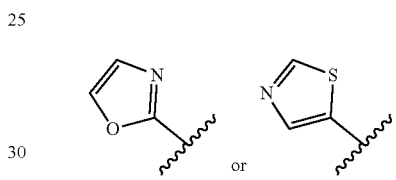

In some embodiments, X is N.

In some embodiments, n is 1.

In some embodiments, Y is N.

In some embodiments, Y is CR$^4$.

In some embodiments, $R^3$ and $R^4$ are taken together with the carbon atoms to which they are attached to form a cyclopropyl group.

In some embodiments, $R^7$ is selected from the group consisting of

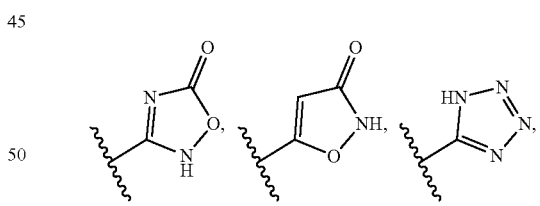

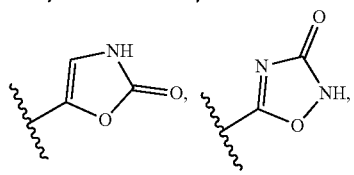

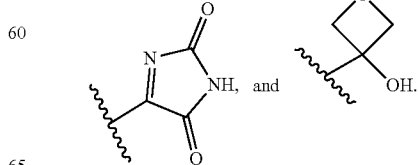

In some embodiments, $R^7$ is

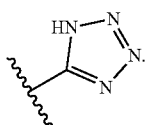

In some embodiments, $R^7$ is

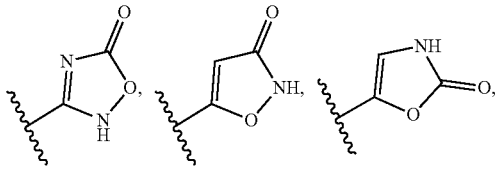

In some embodiments, $R^7$ is

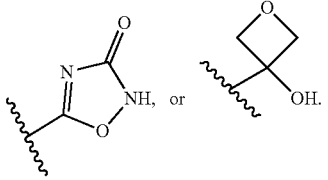

In some embodiments, $R^7$ is

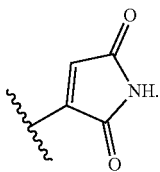 [SMILES: *C1=CC(=O)NC1=O]

In some embodiments, $R^7$ is

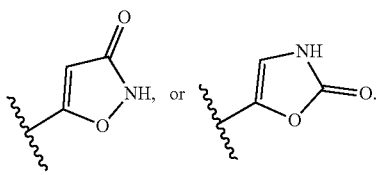 [SMILES: *c1cc(=O)[nH]o1 ; *c1c[nH]c(=O)o1]

In some embodiments, $R^7$ is

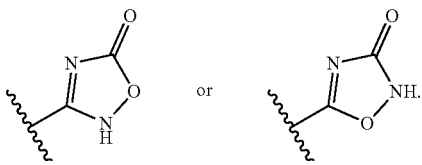 [SMILES: *c1nc(=O)o[nH]1 ; "or" ; *c1nc(=O)[nH]o1]

In some embodiments, $R^7$ is —C(O)NH—$R^8$. In some embodiments, $R^8$ is hydrogen. In some embodiments, $R^8$ is —OH. In some embodiments, $R^8$ is —S(O)$_2$—C$_1$-C$_6$ alkyl. In some embodiments, $R^8$ is —S(O)$_2$CH$_3$. In some embodiments, $R^8$ is —C$_1$-C$_6$ alkyl optionally substituted by halo. In some embodiments, $R^8$ is —C$_1$-C$_2$ alkyl, each of which is independently optionally substituted by halo. In some embodiments, $R^8$ is —CH$_2$CF$_3$. In some embodiments, $R^8$ is —CH$_3$.

In some embodiments, Ring A is 6-membered heteroaryl. In some embodiments, Ring A is

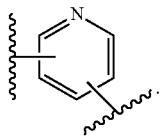

In some embodiments, Ring A is

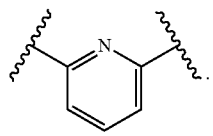 [SMILES: *c1cccc(*)n1]

In some embodiments, Ring A is 9-membered heteroaryl. In some embodiments, Ring A is

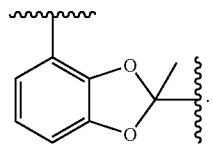

In some embodiments, L is *—O—C$_1$-C$_6$ alkylene-**. In some embodiments, L is *—O—CH$_2$—**.

In some embodiments, Ring B is C$_6$ aryl, which is optionally substituted by one to three substituents independently selected from the group consisting of halo and CN. In some embodiments, Ring B is C$_6$ aryl, which is optionally substituted by one to three substituents independently selected from the group consisting of —F, —Cl, —Br, and —CN. In some embodiments, Ring B is

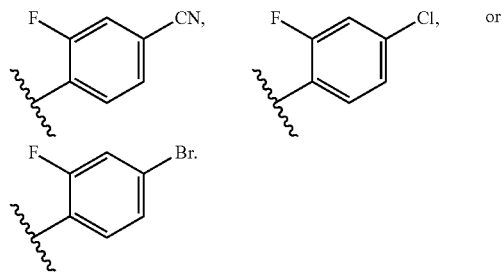

In an aspect, the present disclosure provides any one of the compounds in Table 1, or a pharmaceutically acceptable salt thereof.

In some embodiments, the present disclosure provides a pharmaceutical composition comprising any one of the compounds disclosed herein, or a pharmaceutically acceptable salt thereof, and a pharmaceutical acceptable excipient.

In some embodiments, the present disclosure provides a method of treating a disease mediated by glucagon-like peptide-1 receptor (GLP-1R) in an individual in need thereof, comprising administering to the individual a therapeutically effective amount of any one of the compounds disclosed herein, or a pharmaceutically acceptable salt thereof, or a pharmaceutical composition disclosed herein. In some embodiments, the disease is a liver disease. IN some embodiments, the liver disease is primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, or oti-antitrypsin deficiency. In some embodiments, the disease is diabetes. In some embodiments, the disease is a cardiometabolic disease.

In some embodiments, the present disclosure provides the use of any one of the compounds disclosed herein, or a pharmaceutically acceptable salt thereof, in the manufacture of a medicament for treating a disease mediated by mediated by GLP-1R.

DETAILED DESCRIPTION

Definitions

As used herein, the following definitions shall apply unless otherwise indicated. Further, if any term or symbol used herein is not defined as set forth below, it shall have its ordinary meaning in the art.

As used herein and in the appended claims, the singular forms "a", "an" and "the" include plural forms, unless the context clearly dictates otherwise.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in connection with a value, contemplate a variation within ±15%, within ±10%, within ±5%, within ±4%, within ±3%, within ±2%, within ±1%, or within ±0.5% of the specified value. Reference to "about" a value or parameter herein includes (and describes) embodiments that are directed to that value or parameter per se. For example, description referring to "about X" includes description of "X".

"Comprising" is intended to mean that the compositions and methods include the recited elements, but not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

As used herein, the term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, "treatment" or "treating" is an approach for obtaining beneficial or desired results including clinical results. For purposes of this disclosure, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of this disclosure contemplate any one or more of these aspects of treatment.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)(CH$_3$CH$_2$)CH—), t-butyl (($CH_3$)$_3$C—), n-pentyl ($CH_3CH_2CH_2CH_2CH_2$—), and neopentyl (($CH_3$)$_3$CCH$_2$—). $C_x$ alkyl refers to an alkyl group having x number of carbon atoms.

"Alkylene" refers to a divalent saturated aliphatic hydrocarbyl group having from 1 to 12 carbon atoms, preferably from 1 to 10 carbon atoms, and more preferably from 1 to 6 carbon atoms. This term includes, by way of example, linear and branched hydrocarbyl groups such as methylene (—$CH_2$—), ethylene (—$CH_2CH_2$— or —CH(Me)-), propylene (—$CH_2CH_2CH_2$— or —CH(Me)CH$_2$—, or —CH(Et)-) and the likes.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Cyano" refers to the group —C≡N.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, sulfonyloxy, thioacyl, thiol, alkylthio, and substituted alkylthio, wherein said substituents are defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, and furanyl. Other preferred heteroaryls include 9 or 10 membered heteroaryls, such as indolyl, quinolinyl, quinolonyl, isoquinolinyl, and isoquinolonyl.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, and oxygen. $C_x$ heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl (S(O)), sulfonyl (S(O)$_2$)moieties.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]

thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Oxo" refers to the atom (=O) or (O).

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

It is understood that an optionally substituted moiety can be substituted with more than five substituents, if permitted by the number of valences available for substitution on the moiety. For example, a propyl group can be substituted with seven halogen atoms to provide a perhalopropyl group. The substituents may be the same or different.

Compounds

In one aspect, provided is a compound of formula (I):

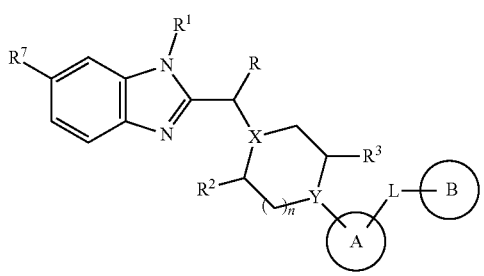

(I)

or a pharmaceutically acceptable salt thereof, wherein:
X is N or CH;
Y is N or $CR^4$;
n is 0 or 1;
R is hydrogen;
$R^1$ is —$C_1$-$C_6$ alkylene-$R^5$;
$R^2$ is hydrogen, oxo, or $C_1$-$C_6$ alkyl;
$R^3$ is hydrogen, oxo, or $C_1$-$C_6$ alkyl and $R^4$ is hydrogen, OH or $C_1$-$C_6$ alkyl,
or $R^3$ and $R^4$ are optionally taken together with the carbon atoms to which they are attached to form $C_3$-$C_6$ cycloalkyl optionally substituted by halo or $C_1$-$C_3$ alkyl;
$R^5$ is 3- to 6-membered heterocyclyl, or 5- to 6-membered heteroaryl, wherein the 3- to 6-membered heterocyclyl or 5- to 6-membered heteroaryl of $R^5$ is independently optionally substituted by halo, $C_1$-$C_6$ alkyl, $C_1$-$C_6$ alkoxy, $C_1$-$C_6$ alkenyl, or $C_1$-$C_6$ haloalkyl;
$R^7$ is 5- to 12-membered heterocyclyl, or 5- to 12-membered heteroaryl, wherein each 5- to 12-membered heterocyclyl or 5- to 12-membered heteroaryl is independently optionally substituted by oxo, or $R^7$ is —C(O)NH—$R^8$, wherein $R^8$ is hydrogen, —OH, —S(O)$_2$—$C_1$-$C_6$ alkyl, or —$C_1$-$C_6$ alkyl optionally substituted by halo;
Ring A is 5- to 12-membered heterocyclyl, 5- to 12-membered heteroaryl, or $C_6$-$C_{14}$ aryl, each of which is independently optionally substituted by halo, oxo, —CN, $C_3$-$C_6$ cycloalkyl, or $C_1$-$C_6$ alkyl optionally substituted by halo or OH;
L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein
* represents the point of attachment to ring A and ** represents the point of attachment to ring B;
when L is *—O—$C_1$-$C_6$ alkylene-**, the $C_1$-$C_6$ alkylene is optionally substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and
when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;
$R^6$ is hydrogen or $C_1$-$C_6$ alkyl; and
Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, and phenyl,
with the proviso that
when $R^7$ is —C(O)NH—$R^8$, $R^1$ is

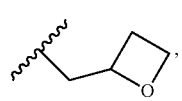 [SMILES: *CC1CCO1],

X is N, Y is CH, n is 1, $R^2$ and $R^3$ are independently hydrogen, ring A is 6-membered heteroaryl, and L is *—OCH$_2$—**, then ring B is not

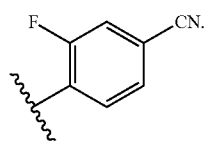 [SMILES: *c1ccc(C#N)cc1F]

In the descriptions herein, it is understood that every description, variation, embodiment or aspect of a moiety/variable may be combined with every description, variation, embodiment or aspect of other moieties/variables the same as if each and every combination of descriptions is specifically and individually listed. For example, every description, variation, embodiment or aspect provided herein with respect to R¹ of Formula (I) may be combined with every description, variation, embodiment or aspect of Ring A the same as if each and every combination were specifically and individually listed.

It is also understood that the provisos provided herein may apply to each embodiment of compounds of Formulae (I) (and subformulae thereof) described herein as long as any of them are applicable.

In some embodiments, the present disclosure provides a compound of formula I, or a pharmaceutically acceptable salt thereof, wherein:

X is N or CH;
Y is N or CR⁴;
n is 0 or 1;
R is hydrogen;
R¹ is —C₁-C₆ alkylene-R⁵;
R² is hydrogen, oxo, or C₁-C₆ alkyl;
R³ is hydrogen, oxo, or C₁-C₆ alkyl and R⁴ is hydrogen, OH or C₁-C₆ alkyl,
or R³ and R⁴ are optionally taken together with the carbon atoms to which they are attached to form C₃-C₆ cycloalkyl optionally substituted by halo or C₁-C₃ alkyl;
R⁵ is 3- to 6-membered heterocyclyl, or 5- to 6-membered heteroaryl, wherein the 3- to 6-membered heterocyclyl or 5- to 6-membered heteroaryl of R⁵ is independently optionally substituted by halo, C₁-C₆ alkyl, C₁-C₆ alkoxy, C₁-C₆ alkenyl, or C₁-C₆ haloalkyl;
R⁷ is selected from the group consisting of

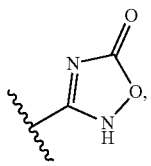 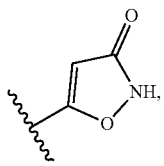 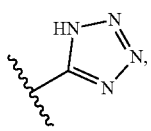

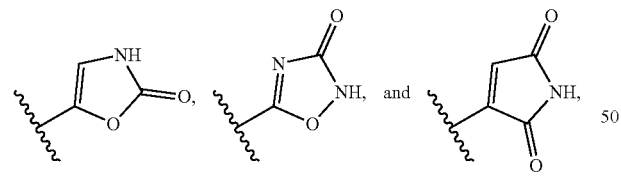

or R⁷ is —C(O)NH—R⁸, wherein R⁸ is hydrogen, —OH, —S(O)₂—C₁-C₆ alkyl, or —C₁-C₆ alkyl optionally substituted by halo;

Ring A is 5- to 12-membered heterocyclyl, 5- to 12-membered heteroaryl, or C₆-C₁₄ aryl, each of which is independently optionally substituted by halo, oxo, —CN, C₃-C₆ cycloalkyl, or C₁-C₆ alkyl optionally substituted by halo or OH;

L is a bond, —O—, C₁-C₆ alkylene, *—O—C₁-C₆ alkylene-**, *—C₁-C₆ alkylene-O—**, or *—NR⁶—C₁-C₆ alkylene-**, wherein
* represents the point of attachment to ring A and ** represents the point of attachment to ring B;

when L is *—O—C₁-C₆ alkylene-**, the C₁-C₆ alkylene is optionally substituted by R^L, wherein each R^L is independently C₁-C₆ alkyl or halo, or two R^L are taken together with the carbon atom or atoms to which they are attached to form C₃-C₆ cycloalkyl or 3- to 6-membered heterocyclyl; and when L is C₁-C₆ alkylene, the C₁-C₆ alkylene is optionally substituted by R^L1, wherein each R^L1 is independently halo, OH, oxo, or C₁-C₆ alkyl, or two R^L1 are taken together with the carbon atom or atoms to which they are attached to form C₃-C₆ cycloalkyl or 3- to 6-membered heterocyclyl;

R⁶ is hydrogen or C₁-C₆ alkyl; and

Ring B is C₃-C₁₀ cycloalkyl, C₆-C₁₄ aryl, 4- to 12-membered heterocyclyl, or 5- to 12-membered heteroaryl, each of which is independently optionally substituted by one to three substituents independently selected from the group consisting of halo, CN, oxo, C₁-C₆ alkyl, C₁-C₆ haloalkyl, —C(O)CH₃, —C(O)NH₂, —S(O)₂CH₃, cyclopropyl, and phenyl, with the proviso that:
when R⁷ is —C(O)NH—R⁸, R¹ is

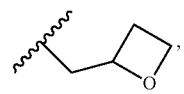

X is N, Y is CH, n is 1, R² and R³ are each hydrogen, ring A is 6-membered heteroaryl, and L is *—OCH₂—**, then ring B is not

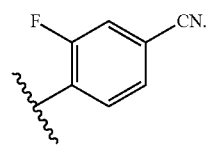 [SMILES: *c1ccc(C#N)cc1F]

In some embodiments of Formula (I), provided is a compound of Formula (I-a):

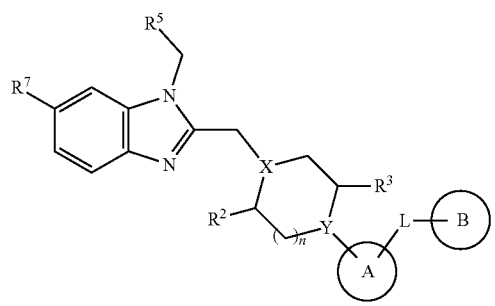

(I-a)

or a pharmaceutically acceptable salt thereof, wherein X, Y, n, R², R³, R⁵, R⁷, Ring A, L, and Ring B are as defined for Formula (I).

In some embodiments of Formula (I-a), X is N and Y is N. In some embodiments, the compound is of Formula (I-b):

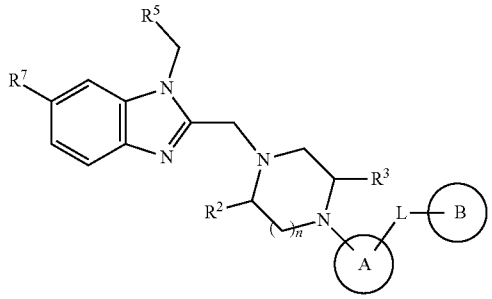

(I-b)

or a pharmaceutically acceptable salt thereof, wherein n, $R^2$, $R^3$, $R^5$, $R^7$, Ring A, L, and Ring B are as defined for Formula (I).

In some embodiments of Formula (I-a), X is N and Y is $CR^4$. In some embodiments, the compound is of Formula (I-c):

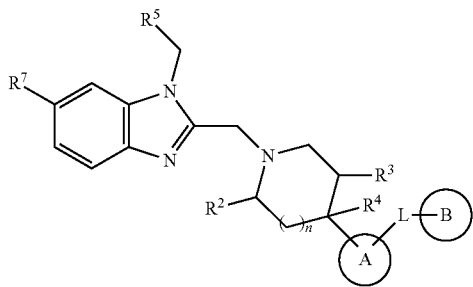

(I-c)

or a pharmaceutically acceptable salt thereof, wherein n, $R^2$, $R^3$, $R^4$, $R^5$, $R^7$, Ring A, L, and Ring B are as defined for Formula (I).

In some embodiments of Formula (I-c), X is N, Y is $CR^4$, and $R^3$ and $R^4$ are taken together with the carbon atoms to which they are attached to form a cyclopropyl group. In some embodiments, the compound is of Formula (I-d-1), (I-d-2), or (I-d-3):

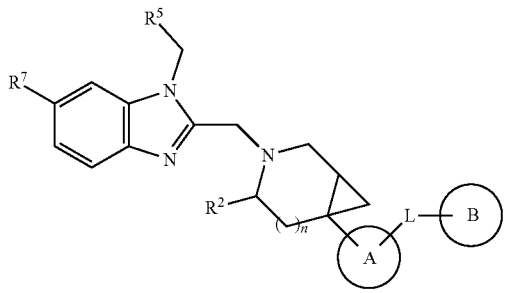

(I-d-1)

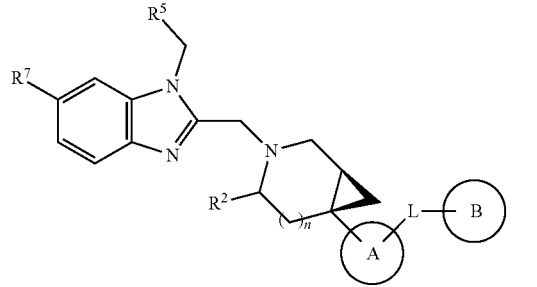

(I-d-2)

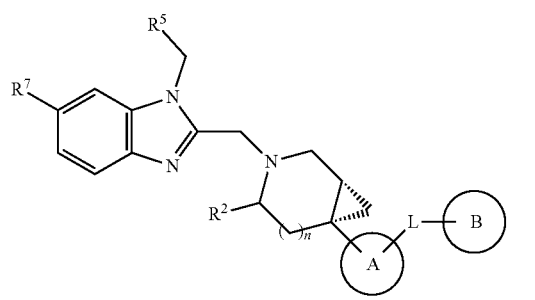

(I-d-3)

or a pharmaceutically acceptable salt thereof, wherein n, $R^2$, $R^5$, $R^7$, Ring A, L, and Ring B are as defined for Formula (I).
In some embodiments, the compound is of formula (I-d-1).
In some embodiments, the compound is of formula (I-d-2).
In some embodiments, the compound is of formula (I-d-3).

In some embodiments of Formula (I-a), Ring A is a 6-membered heteroaryl comprising 1, 2, or 3 heteroatoms. In some embodiments the compound is of Formula (I-e):

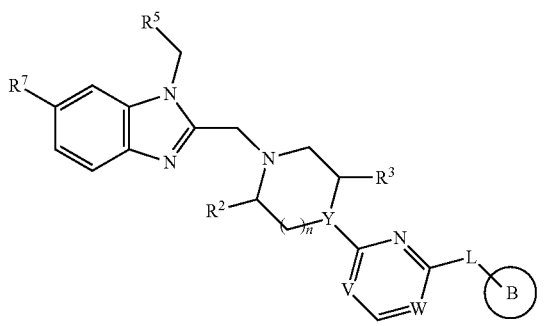

(I-e)

or a pharmaceutically acceptable salt thereof, wherein X, Y, n, $R^2$, $R^3$, $R^5$, $R^7$, L, and Ring B are as defined for Formula (I), and V and W are independently N or $CR^4$, wherein each $R^4$ is H, halo, CN, $C_3$-$C_6$ cycloalkyl, or $C_1$-$C_6$ alkyl optionally substituted by halo or OH. In some embodiments, V is N and W is $CR^4$. In some embodiments, V is $CR^4$ and W is N. In some embodiments, V and W are each $CR^4$. In some embodiments, V and W are each N. In some embodiments, V is N and W is CH. In some embodiments, V is CH and W is N. In some embodiments, V and W are each CH.

In some embodiments of Formula (I-e), L is *—O—$C_1$-$C_6$ alkylene-**, optionally substituted by $R^L$ as described for Formula (I). In some embodiments, L is *—O—$CH_2$—**. In some embodiments the compound is of Formula (I-f):

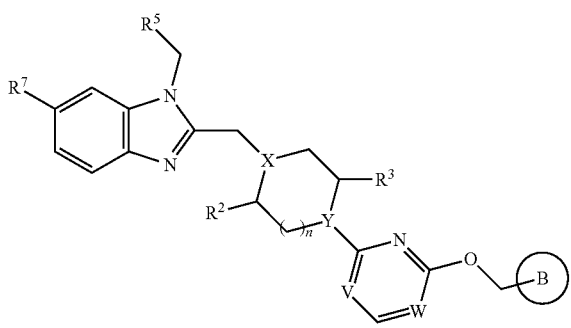

(I-f)

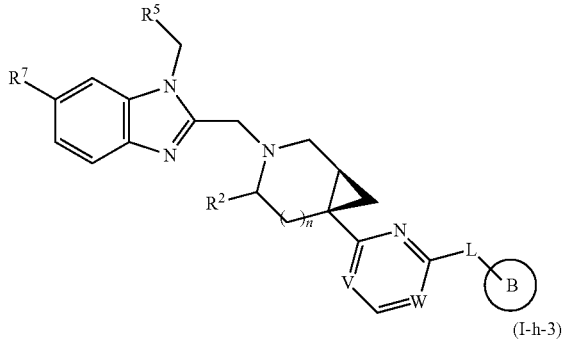

(I-h-2)

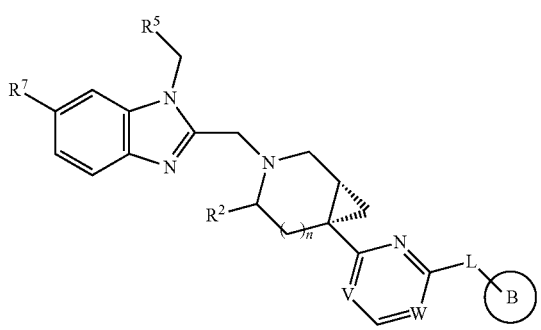

(I-h-3)

wherein n, X, Y, $R^2$, $R^3$, $R^5$, $R^7$, and Ring B are as defined for Formula (I), and V and W are as defined for formula (I-e).

In some embodiments of Formula (I-f), Ring B is a phenyl group optionally substituted by one or more $R^B$, wherein each $R^B$ is independently selected from the group consisting of halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2C_1$-$C_6$ alkyl, and phenyl. In some embodiments the compound is of Formula (I-g):

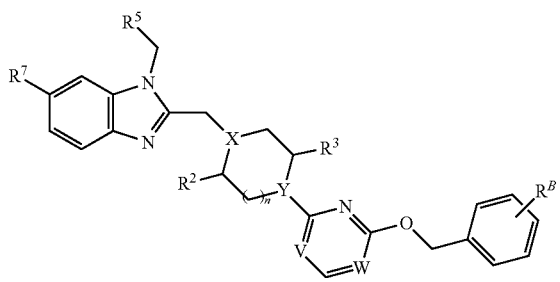

(I-g)

wherein n, X, Y, $R^2$, $R^3$, $R^5$, and $R^7$ are as defined for Formula (I), and V and W are as defined for formula (I-e).

In some embodiments of Formula (I-e), X is N, Y is $CR^4$, and $R^3$ and $R^4$ are taken together with the carbon atoms to which they are attached to form a cyclopropyl group. In some embodiments the compound is of Formula (I-h-1), (I-h-2), (I-h-3):

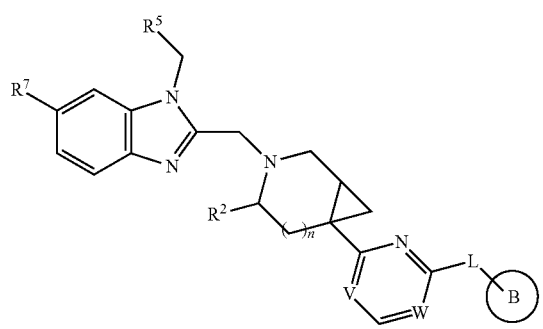

(I-h-1)

wherein n, $R^2$, $R^5$, $R^7$, L, and Ring B are as defined for Formula (I), and V and W are as defined for formula (I-e). In some embodiments, the compound is of formula (I-h-1). In some embodiments, the compound is of formula (I-h-2). In some embodiments, the compound is of formula (I-h-3).

In some embodiments of Formula (I-e), X is N, Y is $CR^4$, $R^3$ and $R^4$ are taken together with the carbon atoms to which they are attached to form a cyclopropyl group, and Ring B is a phenyl group optionally substituted by one or more $R^B$, wherein each $R^B$ is independently selected from the group consisting of halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2C_1$-$C_6$ alkyl, and phenyl. In some embodiments the compound is of Formula (I-i):

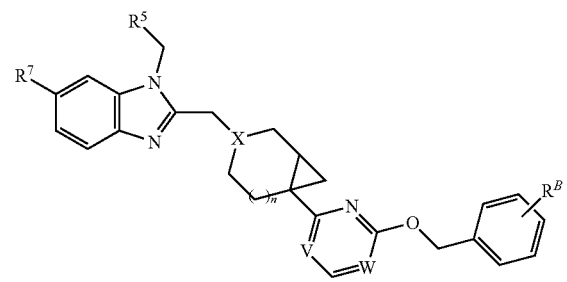

(I-i)

or a pharmaceutically acceptable salt thereof, wherein n, $R^5$, and $R^7$ are as defined for Formula (I), and V and W are as defined for formula (I-e).

In some embodiments of Formula (I-a), Ring A is pyridine and L is *—O—$C_1$-$C_6$ alkylene-**, optionally substituted by $R^L$ as described for Formula (I). In some embodiments, Ring A is pyridine and L is *—O—CH$_2$—**. In some embodiments, the compound is of Formula (I-j):

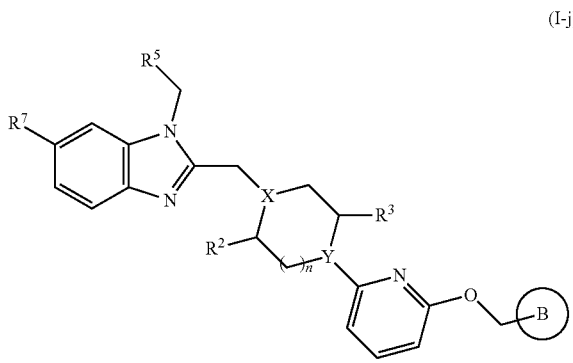

(I-j)

or a pharmaceutically acceptable salt thereof, wherein n, X, Y, $R^5$, $R^7$, and Ring B are as defined for Formula (I).

In some embodiments of Formula (I-j), X is N, Y is N, $R^2$ is H, $R^3$ is H, and n is 1. In some embodiments, the compound is of Formula (I-k):

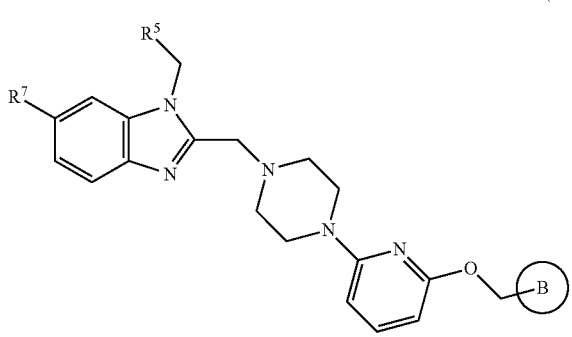

(I-k)

or a pharmaceutically acceptable salt thereof, wherein $R^5$, $R^7$, and Ring B are as defined for Formula (I).

In some embodiments of Formula (I-j), X is N, Y is CH, $R^2$ is H, $R^3$ is H, and n is 1. In some embodiments, the compound is of Formula (I-1):

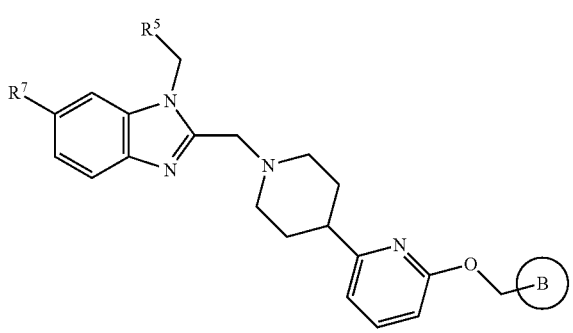

(I-1)

or a pharmaceutically acceptable salt thereof, wherein $R^5$, $R^7$, and Ring B are as defined for Formula (I).

In some embodiments of Formula (I-j), $R^2$ is H, n is 1, and Ring B is phenyl, optionally substituted by one or more $R^x$, wherein each $R^x$ is independently selected from the group consisting of halo and —CN. In some embodiments, the compound is of Formula (I-m):

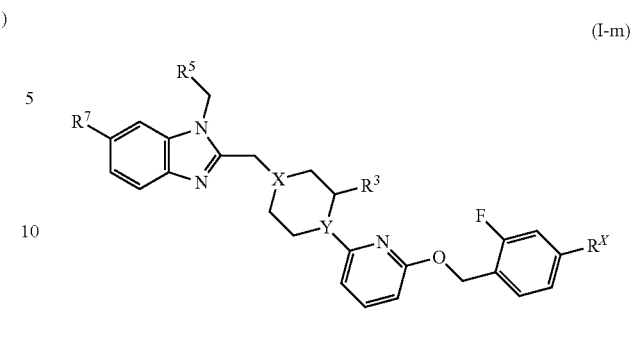

(I-m)

or a pharmaceutically acceptable salt thereof, wherein X, Y, $R^3$, $R^5$, and $R^7$ are as defined for Formula (I), and $R^x$ is as defined above.

In some embodiments of Formula (I-a), X is N, Y is $CR^4$, $R^3$ and $R^4$ are taken together with the carbon atoms to which they are attached to form a cyclopropyl group, and Ring B is 2-fluoro-4-cyanophenyl. In some embodiments, provided is a compound of Formula (I-n):

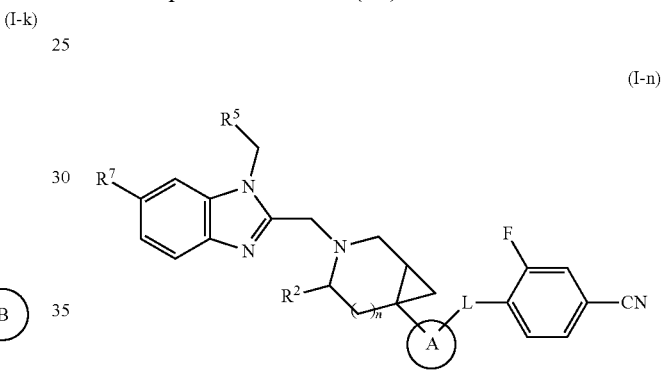

(I-n)

or a pharmaceutically acceptable salt thereof, wherein n, $R^2$, $R^5$, $R^7$, Ring A, and L are as defined for Formula (I).

In some embodiments of Formula (I), L is —O—. In some embodiments, provided is a compound of Formula (I-o):

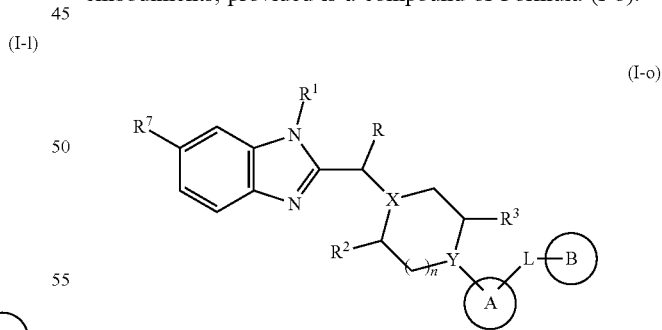

(I-o)

or a pharmaceutically acceptable salt thereof, wherein n, X, Y, $R^1$, $R^2$, $R^3$, $R^7$, Ring A, and Ring B are as defined for Formula (I).

In some embodiments of Formula (I), L is *—$NR^6$—$C_1$-$C_6$ alkylene-**, wherein $R^6$ is hydrogen or $C_1$-$C_6$ alkyl. In some embodiments, L is *—$NR^6$—$CH_2$—** wherein $R^6$ is hydrogen or $C_1$-$C_6$ alkyl. In some embodiments, provided is a compound of Formula (I-p):

(I-p)

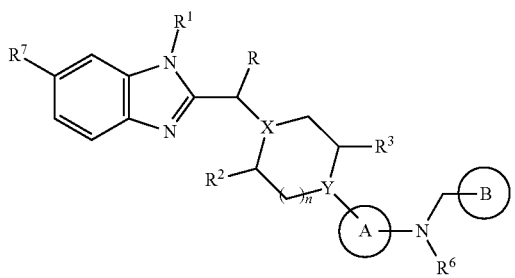

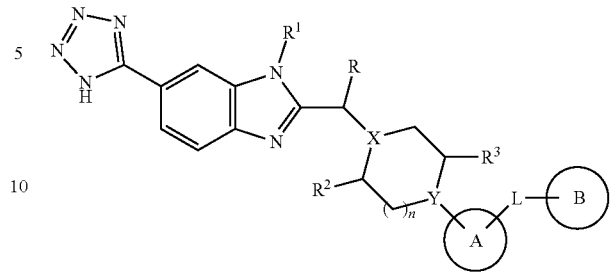

(I-q-4)

or a pharmaceutically acceptable salt thereof, wherein n, X, Y, R, $R^1$, $R^2$, $R^3$, $R^6$, $R^7$, Ring A, and Ring B are as defined for Formula (I).

In some embodiments of Formula (I), provided is a compound of Formula (I-q-1), (I-q-2), (I-q-3), (I-q-4), (I-q-5), (I-q-6), or (I-q-7):

(I-q-1)

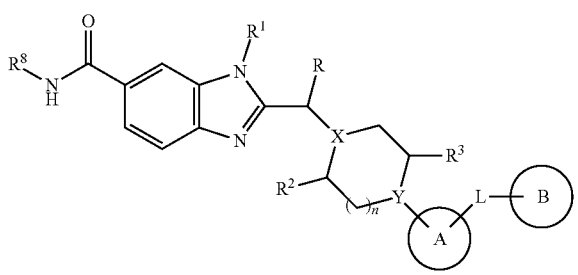

(I-q-5)

(I-q-6)

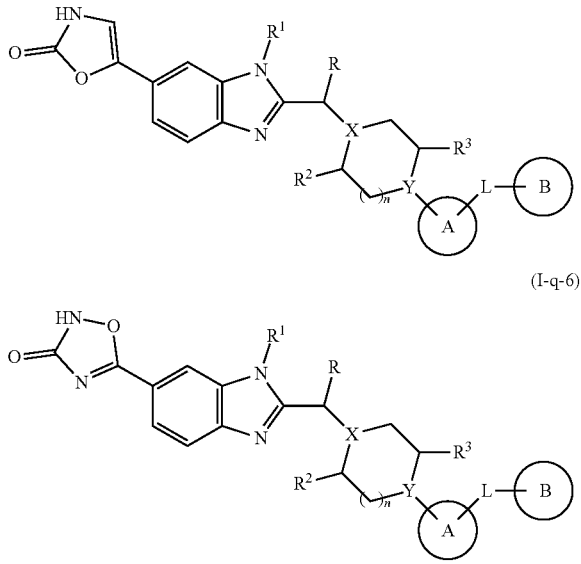

(I-q-2)

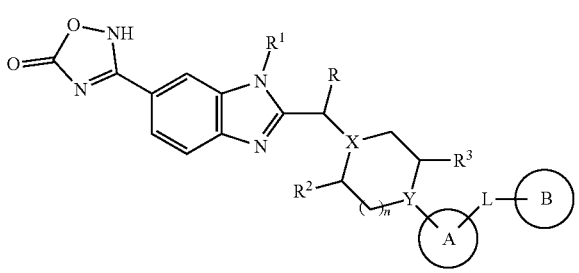

(I-q-7)

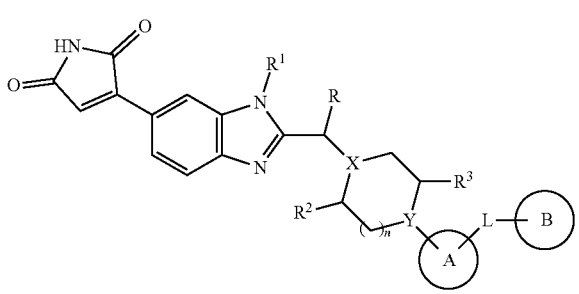

(I-q-3)

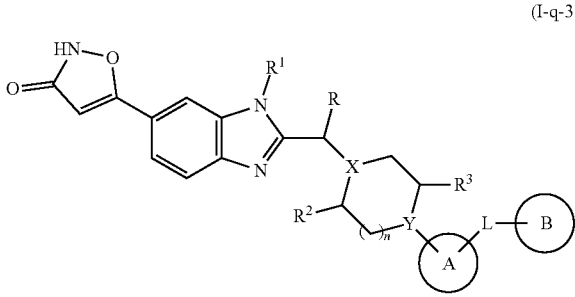

or a pharmaceutically acceptable salt thereof, wherein X, Y, n, $R^1$, $R^2$, $R^3$, Ring A, L, and Ring B are as defined for Formula (I). In some embodiments, the compound is of formula (I-q-1). In some embodiments, the compound is of formula (I-q-2). In some embodiments, the compound is of formula (I-q-3). In some embodiments, the compound is of formula (I-q-4). In some embodiments, the compound is of formula (I-q-5). In some embodiments, the compound is of formula (I-q-6). In some embodiments, the compound is of formula (I-q-7).

In some embodiments, the present disclosure provides a compound wherein the compound of Formula I is of Formula I-s:

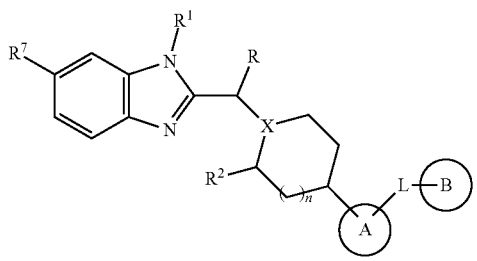

(I-s)

or a pharmaceutically acceptable salt thereof.

In some embodiments, the present disclosure provides a compound wherein the compound of Formula I is of Formula I-t:

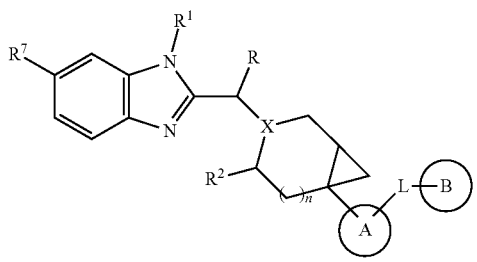

(I-t)

or a pharmaceutically acceptable salt thereof.

In some embodiments of a compound of Formula (I) (including subformulae thereof, if applicable), or a pharmaceutically acceptable salt thereof:

n is 1;
X is N;
$R^2$ is hydrogen;
$R^5$ is an optionally substituted five-membered heteroaryl comprising one or two heteroatoms selected from the group consist of oxygen, nitrogen, and sulfur, or an optionally substituted four-membered heterocycle comprising one oxygen atom;
$R^7$ is

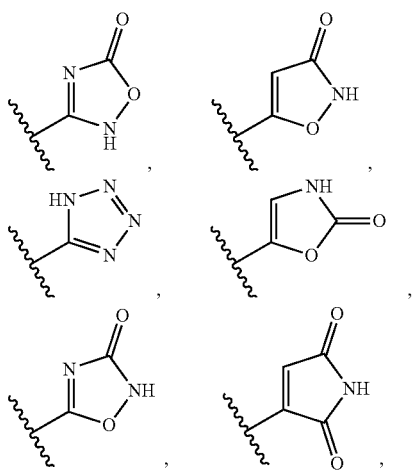

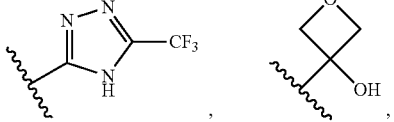

—C(O)NHCH$_3$, —C(O)NH$_2$, C(O)NHCH$_2$CF$_3$, C(O)NHS (O)$_2$CH$_3$, or C(O)NHOH.

Ring A is an optionally substituted 6-9-membered heteroaryl;
L is a bond or *—O—CH$_2$—**; and
Ring B is phenyl optionally substituted by one to three substituents independently selected from the group consisting of halo and cyano.

In some embodiments of a compound of Formula (I) (including subformulae thereof, if applicable), or a pharmaceutically acceptable salt thereof, $R^1$ is —CH$_2$—$R^5$.

In some embodiments of a compound of Formula (I) (including subformulae thereof, if applicable), or a pharmaceutically acceptable salt thereof, $R^1$ is —CH$_2$—$R^5$ and $R^5$ is 4-membered heterocyclyl optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is

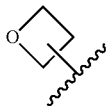

optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is

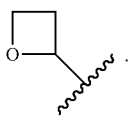

In some embodiments of a compound of Formula (I) (including subformulae thereof, if applicable), or a pharmaceutically acceptable salt thereof, $R^1$ is —CH$_2$—$R^5$ and $R^5$ is 5-membered heteroaryl optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is

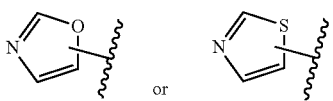

or optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is

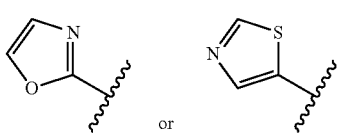 [SMILES: *c1ncco1 ; *c1cncs1]

or optionally substituted by halo, $C_1$-$C_6$ alkyl, $C_1$-$C_6$ alkoxy, $C_1$-$C_6$ alkenyl, or $C_1$-$C_6$ haloalkyl. In some embodiments, $R^5$ is

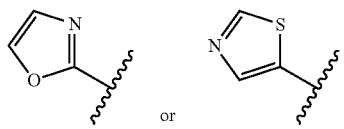

or .

In some embodiments of a compound of Formula (I) (including subformulae thereof, if applicable), or a pharmaceutically acceptable salt thereof, X is N.

In some embodiments of a compound of Formula (I) (including subformulae thereof, if applicable), or a pharmaceutically acceptable salt thereof, n is 1.

In some embodiments of a compound of Formula (I) (including subformulae thereof, if applicable), or a pharmaceutically acceptable salt thereof, Y is N. In other embodiments, Y is $CR^4$. In some such embodiments, $R^3$ and $R^4$ are taken together with the carbon atoms to which they are attached to form cyclopropyl optionally substituted by halo or $C_1$-$C_3$ alkyl.

In some embodiments of a compound of Formula (I) (including subformulae thereof, if applicable), or a pharmaceutically acceptable salt thereof, $R^7$ is

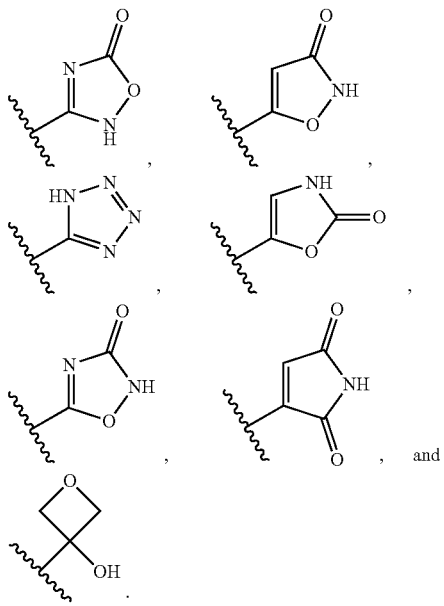

, and

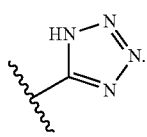 [SMILES: *c1nnn[nH]1]

.

In some embodiments of a compound of Formula (I) (including subformulae thereof, if applicable), or a pharmaceutically acceptable salt thereof, $R^7$ is In some embodiments of a compound of Formula (I) (including subformulae thereof, if applicable), or a pharmaceutically acceptable salt thereof, $R^7$ is

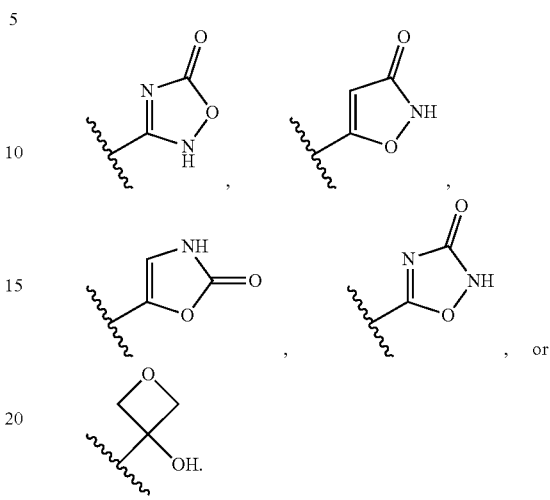

, or .

In some embodiments of a compound of Formula (I) (including subformulae thereof, if applicable), or a pharmaceutically acceptable salt thereof, $R^7$ is

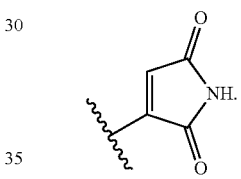

.

In some embodiments of a compound of Formula (I) (including subformulae thereof, if applicable), or a pharmaceutically acceptable salt thereof, $R^7$ is

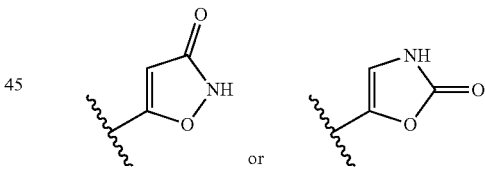

or .

In some embodiments of a compound of Formula (I) (including subformulae thereof, if applicable), or a pharmaceutically acceptable salt thereof, $R^7$ is

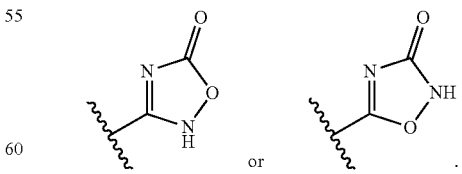

or .

In some embodiments of a compound of Formula (I) (including subformulae thereof, if applicable), or a pharmaceutically acceptable salt thereof, $R^7$ is —C(O)NH—$R^8$. In some such embodiments, $R^8$ is hydrogen. In other such embodiments, $R^8$ is —OH.

In some embodiments of a compound of Formula (I) (including subformulae thereof, if applicable), or a pharmaceutically acceptable salt thereof, $R^7$ is —C(O)NH—$R^8$ and $R^8$ is —S(O)$_2$—C$_1$-C$_6$ alkyl. In some such embodiments, $R^8$ is —S(O)$_2$CH$_3$.

In some embodiments of a compound of Formula (I) (including subformulae thereof, if applicable), or a pharmaceutically acceptable salt thereof, $R^7$ is —C(O)NH—$R^8$ and $R^8$ is —C$_1$-C$_6$ alkyl optionally substituted by halo. In some such embodiments, $R^8$ is —C$_1$-C$_2$ alkyl, each of which is independently optionally substituted by halo. In some such embodiments, $R^8$ is —CH$_2$CF$_3$. In other such embodiments, $R^8$ is —CH$_3$.

In some embodiments of a compound of Formula (I) (including subformulae thereof, if applicable), or a pharmaceutically acceptable salt thereof, Ring A is 6-membered heteroaryl optionally substituted by halo, oxo, —CN, C$_3$-C$_6$ cycloalkyl, or C$_1$-C$_6$ alkyl optionally substituted by halo or OH. In some such embodiments, Ring A is

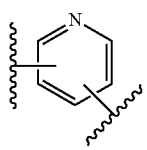

In some such embodiments, Ring A is

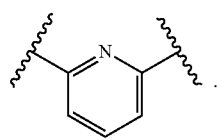 [SMILES: *c1cccc(*)n1]

In some embodiments, Ring A is a 9-membered heteroaryl. In some embodiments, Ring A is

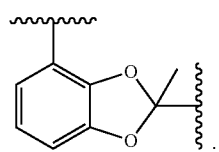 [SMILES: *c1cccc2c1OC(*)(C)O2]

In some embodiments of a compound of Formula (I) (including subformulae thereof, if applicable), or a pharmaceutically acceptable salt thereof, L is *—O—C$_1$-C$_6$ alkylene-**. In some embodiments, L is *—O—CH$_2$—**.

In some embodiments of a compound of Formula (I) (including subformulae thereof, if applicable), or a pharmaceutically acceptable salt thereof, Ring B is C$_6$ aryl, which is optionally substituted by one to three substituents independently selected from the group consisting of halo and CN. In some such embodiments Ring B is

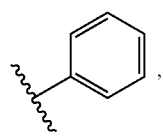 [SMILES: *c1ccccc1]

which is optionally substituted by one to three substituents independently selected from the group consisting of —F, —Cl, —Br, and —CN. In some such embodiments, Ring B is

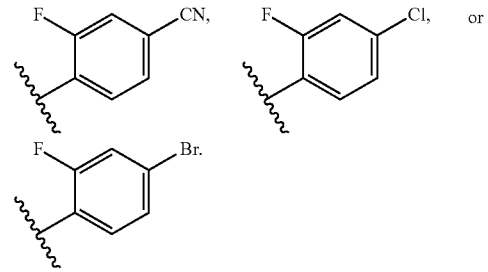

In some embodiments of a compound of Formula (I) (including subformulae thereof, if applicable), or a pharmaceutically acceptable salt thereof, $R^1$ is —C$_1$-C$_6$ alkylene-$R^5$. In some such embodiments, $R^1$ is —CH$_2$CH$_2$—$R^5$. In other such embodiments, $R^1$ is —CH$_2$—$R^5$.

In some embodiments of a compound of Formula (I) (including subformulae thereof, if applicable), or a pharmaceutically acceptable salt thereof, $R^5$ is —C$_{1-6}$ alkoxy. In some such embodiments, $R^5$ is —OCH$_3$. In other embodiments, $R^5$ is —C(O)C$_1$-C$_6$ alkyl optionally substituted by —CN. In some such embodiments, $R^5$ is —C(O)C$_2$ alkyl optionally substituted by —CN. In other embodiments, $R^5$ is 3- to 6-membered heterocyclyl which is optionally substituted by halo. C$_1$-C$_6$ alkyl, C$_1$-C$_6$ alkoxy, C$_1$-C$_6$ alkenyl, or. C$_1$-C$_6$ haloalkyl. In some such embodiments, $R^5$ is 3- to 6-membered heterocyclyl which is optionally substituted by —CH$_3$, —CH$_2$CH$_3$, —OCH$_3$, —CH═CH$_2$, or —Br. In other embodiments, $R^5$ is 5- to 6-membered heteroaryl which is optionally substituted by C$_1$-C$_6$ alkyl, C$_1$-C$_6$ alkoxy, C$_1$-C$_6$ alkenyl, or halo. In some such embodiments, $R^5$ is 5- to 6-membered heteroaryl which is optionally substituted by —CH$_3$, —CH$_2$CH$_3$, —OCH$_3$, —CH═CH$_2$, or —Br.

In some embodiments of a compound of Formula (I) (including subformulae thereof, if applicable), or a pharmaceutically acceptable salt thereof, $R^5$ is 4-membered heterocyclyl which is optionally substituted by halo, C$_1$-C$_6$ alkyl, C$_1$-C$_6$ alkoxy, C$_1$-C$_6$ alkenyl, or C$_1$-C$_6$ haloalkyl. In some such embodiments, $R^5$ is 4-membered heterocyclyl which is optionally substituted by —CH$_3$, —CH$_2$CH$_3$, —OCH$_3$, —CH═CH$_2$, or —Br. In other embodiments, $R^5$ is 5-membered heterocyclyl which is optionally substituted by C$_1$-C$_6$ alkyl, C$_1$-C$_6$ alkoxy, C$_1$-C$_6$ alkenyl, or halo. In some such embodiments, $R^5$ is 5-membered heterocyclyl which is optionally substituted by —CH$_3$, —CH$_2$CH$_3$, —OCH$_3$, —CH═CH$_2$, or —Br.

In some embodiments of a compound of Formula (I) (including subformulae thereof, if applicable), or a pharmaceutically acceptable salt thereof, $R^5$ is 4-membered heterocyclyl which is optionally substituted by halo, C$_1$-C$_6$ alkyl, C$_1$-C$_6$ alkoxy, C$_1$-C$_6$ alkenyl, or C$_1$-C$_6$ haloalkyl. In some such embodiments, $R^5$ is 4-membered heterocyclyl which is optionally substituted by —CH$_3$, —CH$_2$CH$_3$, —OCH$_3$, —CH═CH$_2$, or —Br. In other embodiments, $R^5$ is

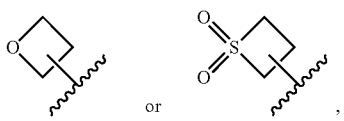 or 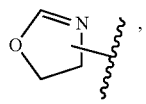, each of which is independently optionally substituted by $C_1$-$C_6$ alkyl, $C_1$-$C_6$ alkoxy, $C_1$-$C_6$ alkenyl, or halo. In some such embodiments, $R^5$ is

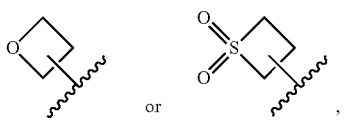 or 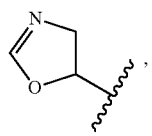, each of which is independently optionally substituted by —$CH_3$, —$CH_2CH_3$, —$OCH_3$, —$CH=CH_2$, or —Br. In other such embodiments, $R^5$ is

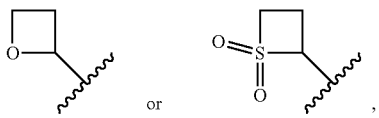 or 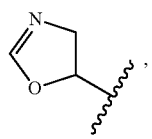, each of which is independently optionally substituted by $C_1$-$C_6$ alkyl, $C_1$-$C_6$ alkoxy, $C_1$-$C_6$ alkenyl, or halo. In some such embodiments, $R^5$ is

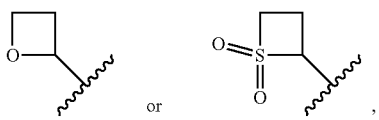 [SMILES: *C1CCO1 ; *C1CCS1(=O)=O] or 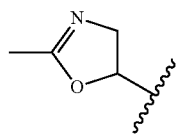, each of which is independently optionally substituted by —$CH_3$, —$CH_2CH_3$, —$OCH_3$, —$CH=CH_2$, or —Br. In some such embodiments, $R^5$ is

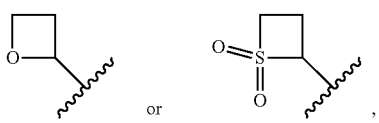 [SMILES: *C1CCO1 ; *C1CCS1(=O)=O] or

In some embodiments of a compound of Formula (I) (including subformulae thereof, if applicable), or a pharmaceutically acceptable salt thereof, $R^5$ is 5-membered heterocyclyl which is optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is 5-membered heterocyclyl which is optionally substituted by —$CH_3$, —$CH_2CH_3$, —$OCH_3$, —$CH=CH_2$, or —Br. In other such embodiments, $R^5$ is

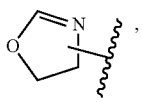, which is optionally substituted by $C_1$-$C_6$ alkyl, $C_1$-$C_6$ alkoxy, $C_1$-$C_6$ alkenyl, or halo. In some such embodiments, $R^5$ is

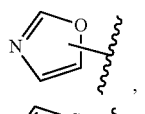, which is optionally substituted by —$CH_3$, —$CH_2CH_3$, —$OCH_3$, —$CH=CH_2$, or —Br. In other such embodiments, $R^5$ is

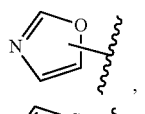, which is optionally substituted by $C_1$-$C_6$ alkyl, $C_1$-$C_6$ alkoxy, $C_1$-$C_6$ alkenyl, or halo. In some such embodiments, $R^5$ is

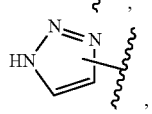, which is optionally substituted by —$CH_3$, —$CH_2CH_3$, —$OCH_3$, —$CH=CH_2$, or —Br. In some such embodiments, $R^5$ is

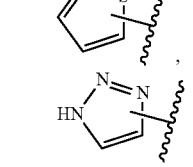.

In some embodiments of a compound of Formula (I) (including subformulae thereof, if applicable), or a pharmaceutically acceptable salt thereof, $R^5$ is 5-membered heteroaryl which is optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is 5-membered heteroaryl which is optionally substituted by —$CH_3$, —$CH_2CH_3$, —$OCH_3$, —$CH=CH_2$, or —Br. In other such embodiments, $R^5$ is

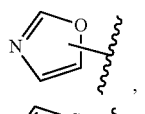, 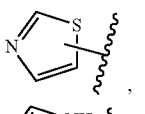, 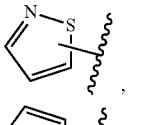,

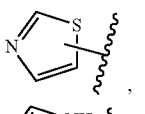, 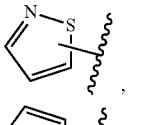, 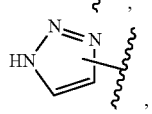, or

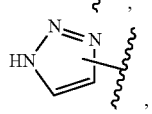, each of which is independently optionally substituted by $C_1$-$C_6$ alkyl, $C_1$-$C_6$ alkoxy, $C_1$-$C_6$ alkenyl, or halo. In some such embodiments, $R^5$ is

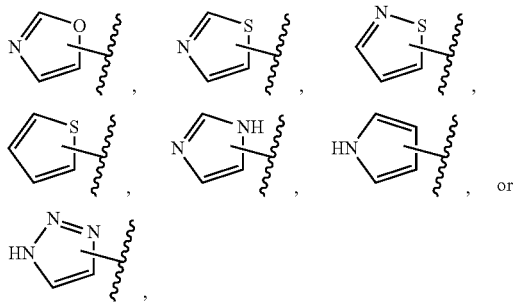

each of which is independently optionally substituted by —$CH_3$, —$CH_2CH_3$, —$OCH_3$, —$CH$=$CH_2$, or —Br. In other such embodiments, $R^5$ is

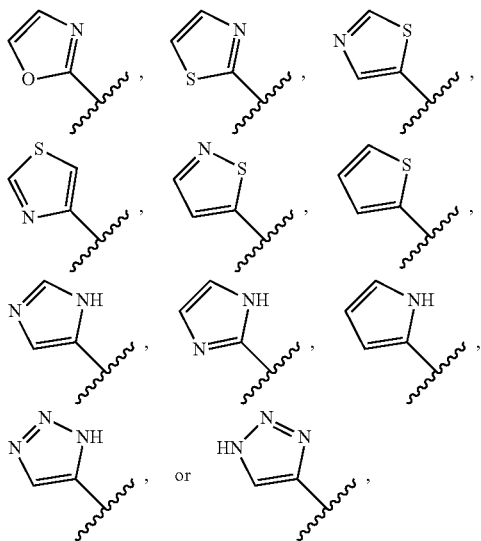

each of which is independently optionally substituted by $C_1$-$C_6$ alkyl, $C_1$-$C_6$ alkoxy, $C_1$-$C_6$ alkenyl, or halo. In some such embodiments, $R^5$ is

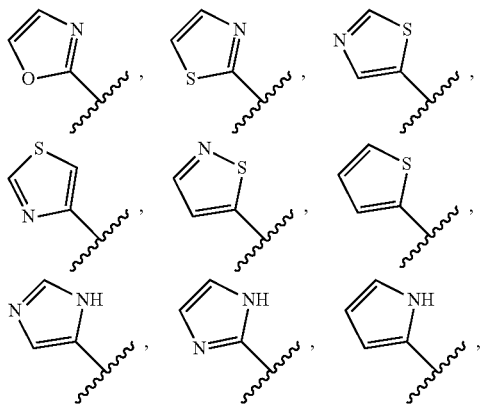

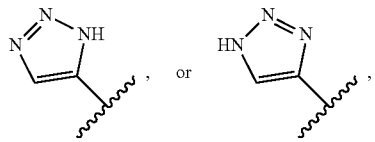

each of which is independently optionally substituted by —$CH_3$, —$CH_2CH_3$, —$OCH_3$, —$CH$=$CH_2$, or —Br. In some such embodiments, $R^5$ is

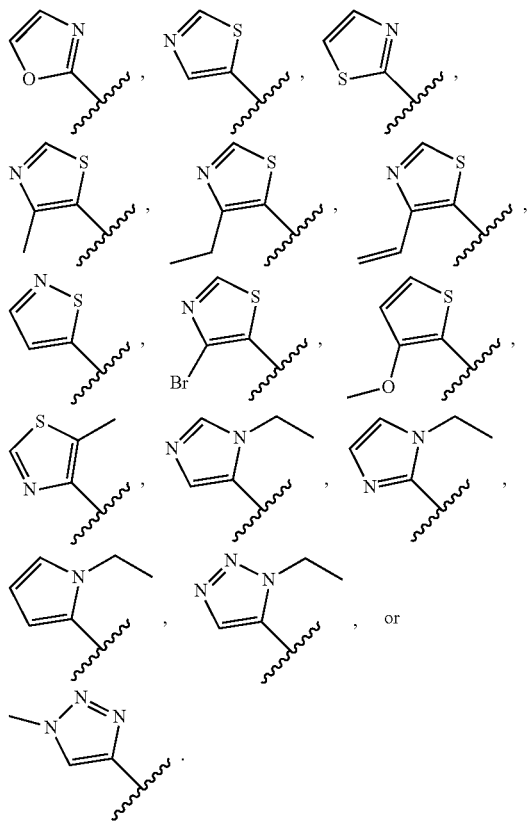

In some embodiments of a compound of Formula (I), or a pharmaceutically acceptable salt thereof, $R^5$ is 5-membered heteroaryl comprising 1, 2, or 3 heteroatoms independently selected from O, N, and S, wherein at least one heteroatom of $R^5$ is S, and further wherein $R^5$ is optionally substituted by halo, $C_1$-$C_6$ alkyl, $C_1$-$C_6$ alkoxy, $C_1$-$C_6$ alkenyl, or $C_1$-$C_6$ haloalkyl. In some such embodiments, $R^5$ is 5-membered heteroaryl comprising 1, 2, or 3 heteroatoms independently selected from O, N, and S, wherein at least one heteroatom of $R^5$ is S, and further wherein $R^5$ is optionally substituted by —$CH_3$, —$CH_2CH_3$, —$OCH_3$, —$CH$=$CH_2$, or —Br. In other such embodiments, $R^5$ is

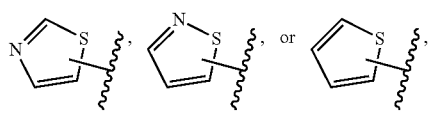

each of which is independently optionally substituted by $C_1$-$C_6$ alkyl, $C_1$-$C_6$ alkoxy, $C_1$-$C_6$ alkenyl, or halo. In some such embodiments, $R^5$ is

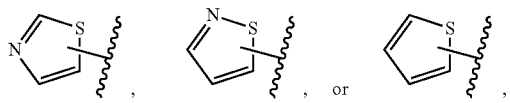

each of which is independently optionally substituted by —$CH_3$, —$CH_2CH_3$, —$OCH_3$, —$CH$=$CH_2$, or —Br. In other such embodiments, $R^5$ is

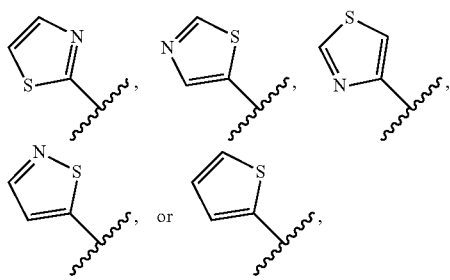

each of which is independently optionally substituted by $C_1$-$C_6$ alkyl, $C_1$-$C_6$ alkoxy, $C_1$-$C_6$ alkenyl, or halo. In some such embodiments, $R^5$ is

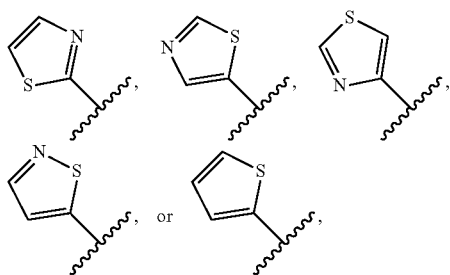

each of which is independently optionally substituted by —$CH_3$, —$CH_2CH_3$, —$OCH_3$, —$CH$=$CH_2$, or —Br. In some such embodiments, $R^5$ is

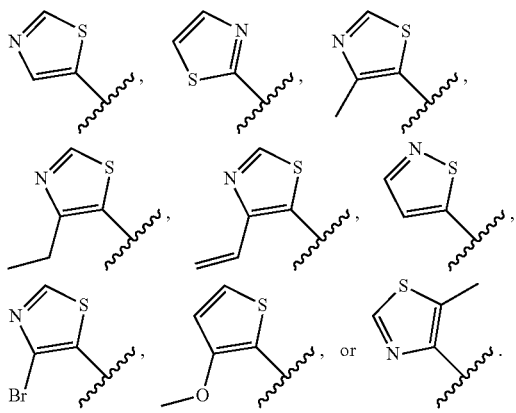

In some embodiments of a compound of Formula (I) (including subformulae thereof, if applicable) or a pharmaceutically acceptable salt thereof, X is N. In other embodiments, X is CH.

In some embodiments of a compound of Formula (I) (including subformulae thereof, if applicable) or a pharmaceutically acceptable salt thereof, n is 0. In other embodiments, n is 1.

In some embodiments of a compound of Formula (I) (including subformulae thereof, if applicable) or a pharmaceutically acceptable salt thereof, Y is N. In other embodiments, Y is $CR^4$. In some such embodiments, $R^3$ and $R^4$ are taken together with the carbon atoms to which they are attached to form a $C_3$-$C_6$ cycloalkyl. In some such embodiments, $R^3$ and $R^4$ are taken together with the carbon atoms to which they are attached to form cyclopropyl.

In some embodiments of a compound of Formula (I) (including subformulae thereof, if applicable) or a pharmaceutically acceptable salt thereof, $R^7$ is —C(O)NH—$R^8$. In some such embodiments, $R^8$ is hydrogen. In other such embodiments, $R^8$ is —OH. In other such embodiments, $R^8$ is —$S(O)_2$—$C_1$-$C_6$ alkyl. In other such embodiments, $R^8$ is —$C_1$-$C_6$ alkyl optionally substituted by halo. In some such embodiments, $R^8$ is $C_2$ alkyl or $C_1$ alkyl, each of which is independently optionally substituted by halo. In some such embodiments, $R^8$ is —$CH_2CF_3$. In other such embodiments, $R^8$ is —$CH_3$.

In some embodiments of a compound of Formula (I) (including subformulae thereof, if applicable) or a pharmaceutically acceptable salt thereof, $R^7$ is 5- to 12-membered heterocyclyl or 5- to 12-membered heteroaryl, each of which is independently optionally substituted by oxo.

In some embodiments of a compound of Formula (I) (including subformulae thereof, if applicable) or a pharmaceutically acceptable salt thereof, $R^7$ is 5-membered heterocyclyl or 5-membered heteroaryl, each of which is independently optionally substituted by oxo. In some such embodiments, $R^7$ is

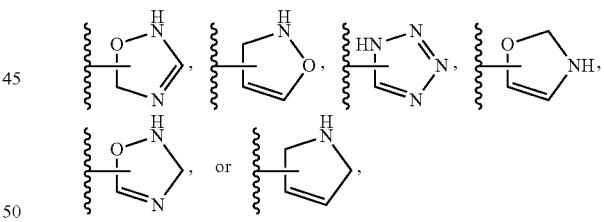

each of which is independently optionally substituted by oxo. In some such embodiments, $R^7$ is

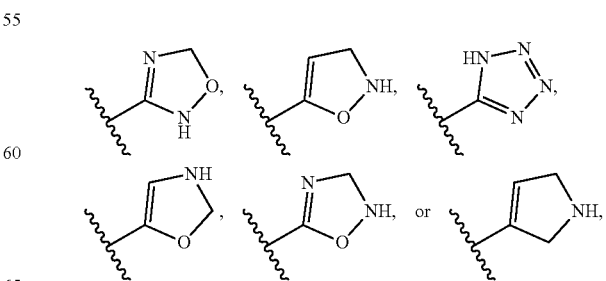

each of which is independently optionally substituted by oxo. In some such embodiments, R⁷ is

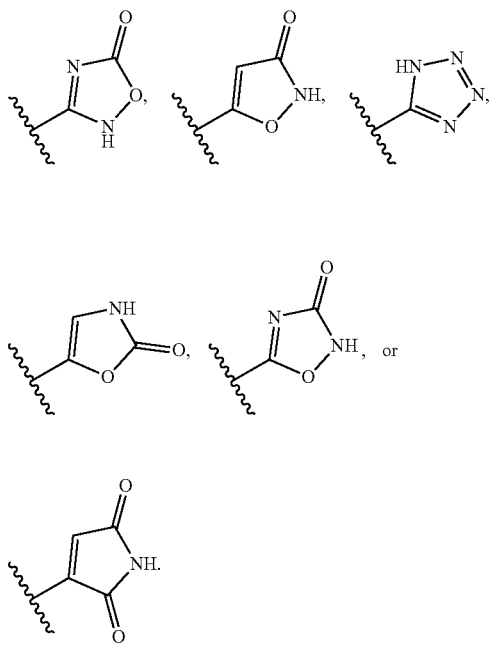

In some embodiments of a compound of Formula (I) (including subformulae thereof, if applicable) or a pharmaceutically acceptable salt thereof, R⁷ is 6-membered heteroaryl optionally substituted by oxo. In some such embodiments, R⁷ is

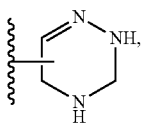

which is optionally substituted by oxo. In some such embodiments, R⁷ is

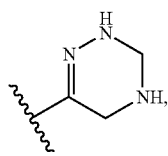 [SMILES: *C1=NNCNC1]

which is optionally substituted by oxo. In some such embodiments, R⁷ is

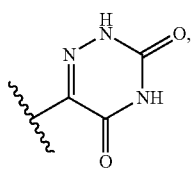 [SMILES: *c1n[nH]c(=O)[nH]c1=O]

In some embodiments of a compound of Formula (I) (including subformulae thereof, if applicable) or a pharmaceutically acceptable salt thereof, Ring A is 5- to 12-membered heterocyclyl, which is optionally substituted by halo, oxo, —CN, $C_3$-$C_6$ cycloalkyl, or $C_1$-$C_6$ alkyl optionally substituted by halo or OH. In some such embodiments, Ring A is 5- to 12-membered heterocyclyl, which is optionally substituted by —Cl, —F, oxo, —CN, cyclopropyl, or $C_1$-$C_3$ alkyl optionally substituted by halo or OH. In other embodiments, Ring A is 5- to 12-membered heteroaryl, which is optionally substituted by halo, oxo, —CN, $C_3$-$C_6$ cycloalkyl, or $C_1$-$C_6$ alkyl optionally substituted by halo or OH. In some such embodiments, Ring A is 5- to 12-membered heteroaryl, which is optionally substituted by —Cl, —F, oxo, —CN, cyclopropyl, or $C_1$-$C_3$ alkyl optionally substituted by halo or OH. In other embodiments, Ring A is $C_6$-$C_{14}$ aryl, which is optionally substituted by halo, oxo, —CN, $C_3$-$C_6$ cycloalkyl, or $C_1$-$C_6$ alkyl optionally substituted by halo or OH. In some such embodiments, Ring A is $C_6$-$C_{14}$ aryl, which is optionally substituted by —Cl, —F, oxo, —CN, cyclopropyl, or $C_1$-$C_3$ alkyl optionally substituted by halo or OH.

In some embodiments of a compound of Formula (I) (including subformulae thereof, if applicable) or a pharmaceutically acceptable salt thereof, Ring A is 9-membered heterocyclyl, which is optionally substituted by halo, oxo, —CN, $C_3$-$C_6$ cycloalkyl, or $C_1$-$C_6$ alkyl optionally substituted by halo or OH. In some such embodiments, Ring A is 9-membered heterocyclyl, which is optionally substituted by —Cl, —F, oxo, —CN, cyclopropyl, or $C_1$-$C_3$ alkyl optionally substituted by halo or OH. In other such embodiments, Ring A is

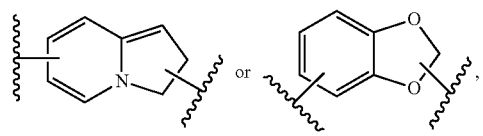

each of which is independently optionally substituted by halo, oxo, —CN, $C_3$-$C_6$ cycloalkyl, or $C_1$-$C_6$ alkyl optionally substituted by halo or OH. In some such embodiments, Ring A is

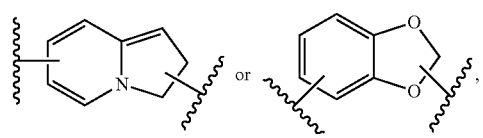

each of which is independently optionally substituted by —Cl, —F, oxo, —CN, cyclopropyl, or $C_1$-$C_3$ alkyl optionally substituted by halo or OH. In other such embodiments, Ring A is

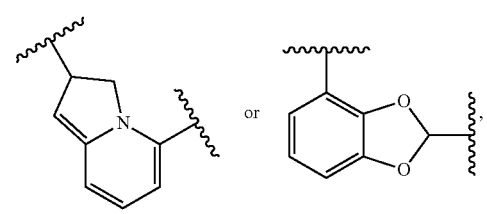 [SMILES: *C1=CC=CC2=CC(*)CN12 ; *c1cccc2c1OC(*)O2]

each of which is independently optionally substituted by halo, oxo, —CN, $C_3$-$C_6$ cycloalkyl, or $C_1$-$C_6$ alkyl optionally substituted by halo or OH. In some such embodiments, Ring A is

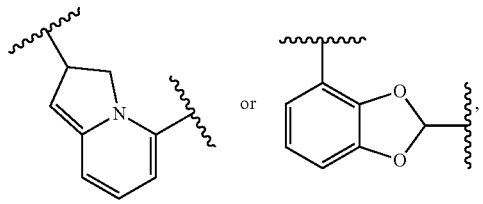 [SMILES: *C1=CC=CC2=CC(*)CN12 ; *c1cccc2c1OC(*)O2]

each of which is independently optionally substituted by —Cl, —F, oxo, —CN, cyclopropyl, or $C_1$-$C_3$ alkyl optionally substituted by halo or OH. In some such embodiments, Ring A is

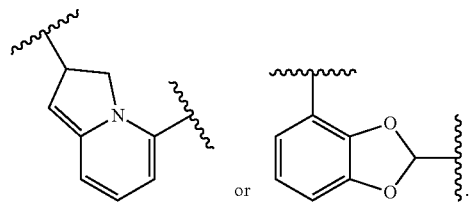 [SMILES: *C1=CC=CC2=CC(*)CN12 ; *c1cccc2c1OC(*)O2]

In some embodiments of a compound of Formula (I) (including subformulae thereof, if applicable) or a pharmaceutically acceptable salt thereof, Ring A is 10-membered heterocyclyl, which is optionally substituted by halo, oxo, —CN, $C_3$-$C_6$ cycloalkyl, or $C_1$-$C_6$ alkyl optionally substituted by halo or OH. In some embodiments, Ring A is 10-membered heterocyclyl, which is optionally substituted by —Cl, —F, oxo, —CN, cyclopropyl, or $C_1$-$C_3$ alkyl optionally substituted by halo or OH. In other such embodiments, Ring A is

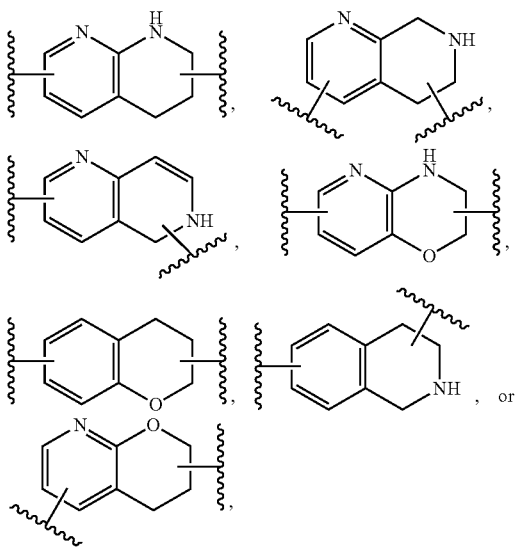

each of which is independently optionally substituted by halo, oxo, —CN, $C_3$-$C_6$ cycloalkyl, or $C_1$-$C_6$ alkyl optionally substituted by halo or OH. In some such embodiments, Ring A is

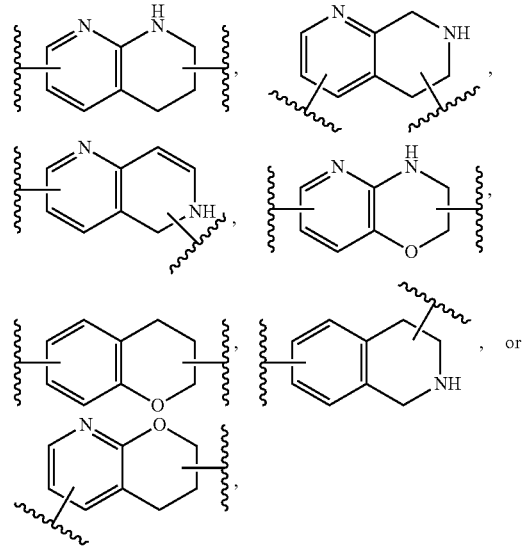

each of which is independently optionally substituted by —Cl, —F, oxo, —CN, cyclopropyl, or $C_1$-$C_3$ alkyl optionally substituted by halo or OH. In other such embodiments, Ring A is

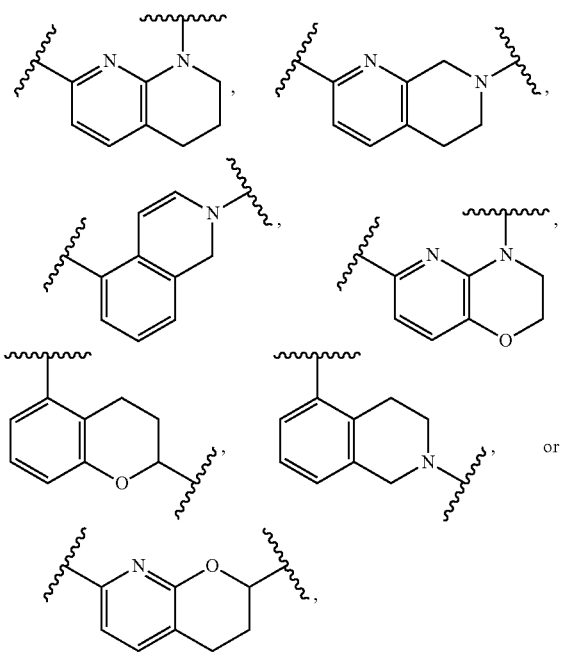

each of which is independently optionally substituted by halo, oxo, —CN, $C_3$-$C_6$ cycloalkyl, or $C_1$-$C_6$ alkyl optionally substituted by halo or OH. In some such embodiments, Ring A is

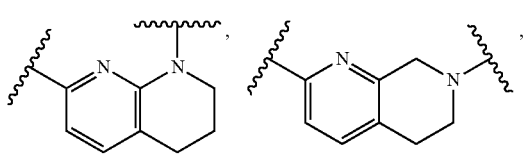

-continued

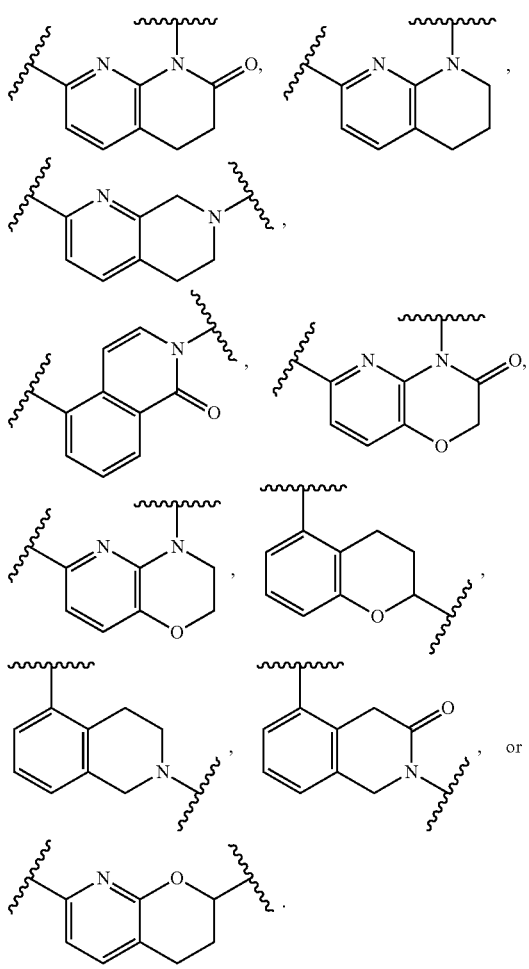

each of which is independently optionally substituted by —Cl, —F, oxo, —CN, cyclopropyl, or $C_1$-$C_3$ alkyl optionally substituted by halo or OH. In some embodiments, Ring A is In some embodiments of a compound of Formula (I) (including subformulae thereof, if applicable) or a pharmaceutically acceptable salt thereof, Ring A is 5-membered heteroaryl, which is optionally substituted by halo, oxo, —CN, $C_3$-$C_6$ cycloalkyl, or $C_1$-$C_6$ alkyl optionally substituted by halo or OH. In some such embodiments, Ring A is 5-membered heteroaryl, which is optionally substituted by —Cl, —F, oxo, —CN, cyclopropyl, or $C_1$-$C_3$ alkyl optionally substituted by halo or OH. In other such embodiments, Ring A is

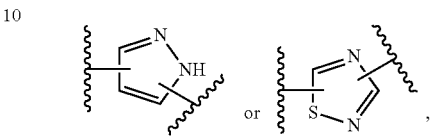

each of which is independently optionally substituted by halo, oxo, —CN, $C_3$-$C_6$ cycloalkyl, or $C_1$-$C_6$ alkyl optionally substituted by halo or OH. In some such embodiments, Ring A is

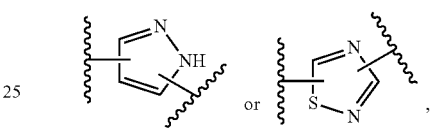

each of which is independently optionally substituted by —Cl, —F, oxo, —CN, cyclopropyl, or $C_1$-$C_3$ alkyl optionally substituted by halo or OH. In other such embodiments, Ring A is

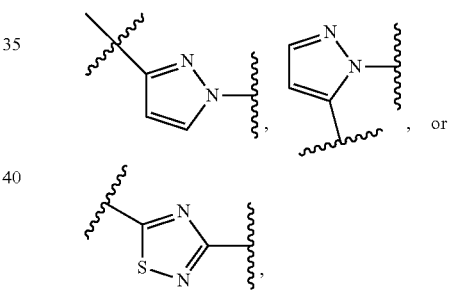

each of which is independently optionally substituted by halo, oxo, —CN, $C_3$-$C_6$ cycloalkyl, or $C_1$-$C_6$ alkyl optionally substituted by halo or OH. In some such embodiments, Ring A is

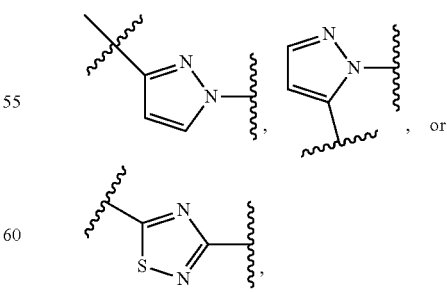

each of which is independently optionally substituted by —Cl, —F, oxo, —CN, cyclopropyl, or $C_1$-$C_3$ alkyl optionally substituted by halo or OH. In some such embodiments, Ring A is

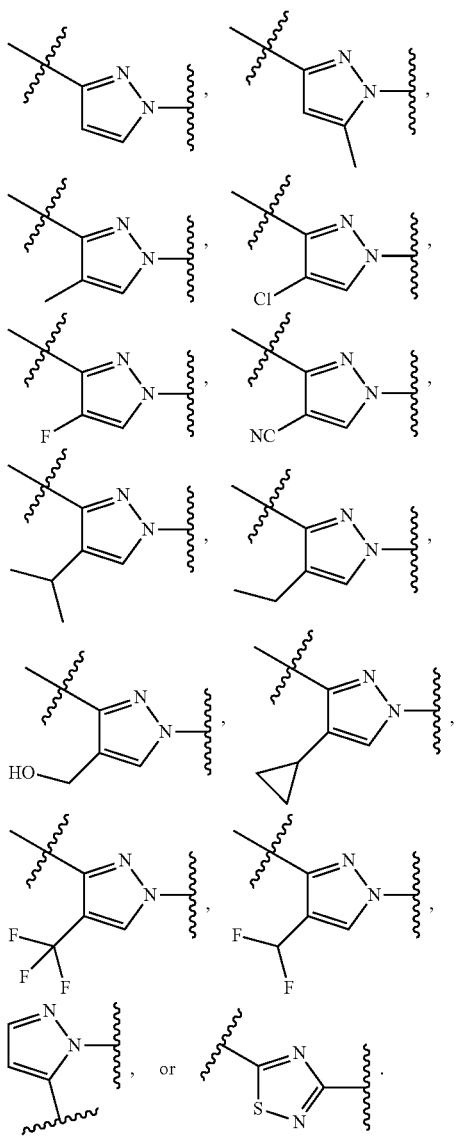

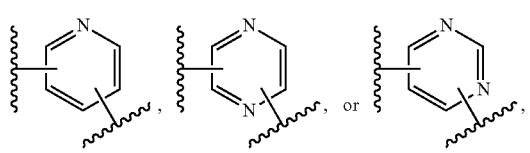

In some embodiments of a compound of Formula (I) (including subformulae thereof, if applicable) or a pharmaceutically acceptable salt thereof, Ring A is 6-membered heteroaryl, which is optionally substituted by halo, oxo, —CN, $C_3$-$C_6$ cycloalkyl, or $C_1$-$C_6$ alkyl optionally substituted by halo or OH. In some embodiments, Ring A is 6-membered heteroaryl, which is optionally substituted by —Cl, —F, oxo, —CN, cyclopropyl, or $C_1$-$C_3$ alkyl optionally substituted by halo or OH. In other such embodiments Ring A is

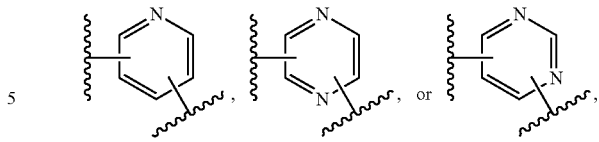

each of which is independently optionally substituted by halo, oxo, —CN, $C_3$-$C_6$ cycloalkyl, or $C_1$-$C_6$ alkyl optionally substituted by halo or OH. In some such embodiments, Ring A is

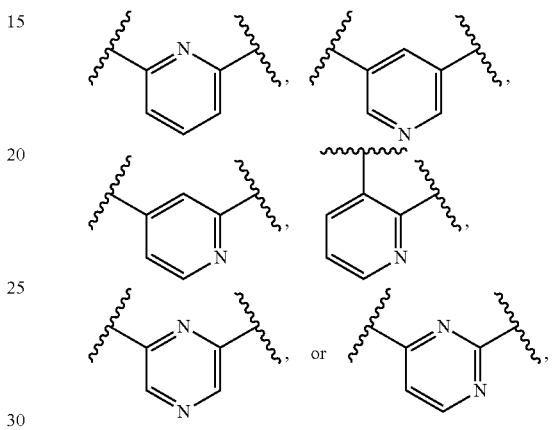

each of which is independently optionally substituted by —Cl, —F, oxo, —CN, cyclopropyl, or $C_1$-$C_3$ alkyl optionally substituted by halo or OH. In other such embodiments, Ring A is

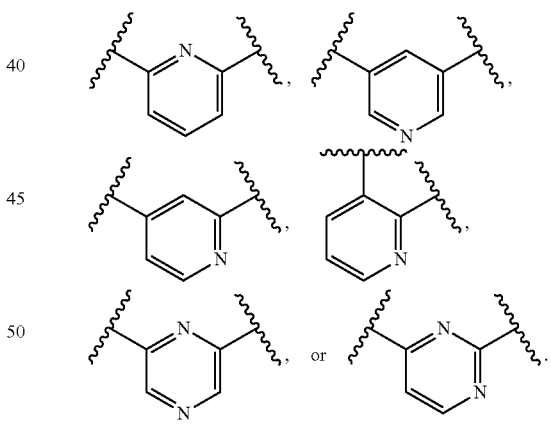

each of which is independently optionally substituted by halo, oxo, —CN, $C_3$-$C_6$ cycloalkyl, or $C_1$-$C_6$ alkyl optionally substituted by halo or OH. In some such embodiments, Ring A is

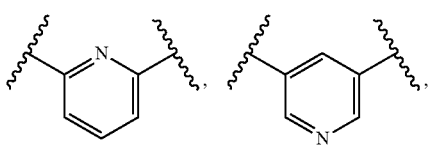

each of which is independently optionally substituted by —Cl, —F, oxo, —CN, cyclopropyl, or $C_1$-$C_3$ alkyl optionally substituted by halo or OH. In some embodiments, Ring A is -continued

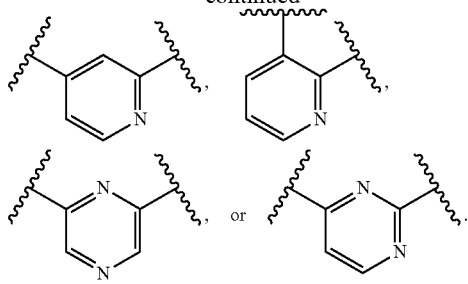

In some embodiments of a compound of Formula (I) (including subformulae thereof, if applicable) or a pharmaceutically acceptable salt thereof, Ring A is 9-membered heteroaryl, which is optionally substituted by halo, oxo, —CN, $C_3$-$C_6$ cycloalkyl, or $C_1$-$C_6$ alkyl optionally substituted by halo or OH. In some such embodiments, Ring A is 9-membered heteroaryl, which is optionally substituted by —Cl, —F, oxo, —CN, cyclopropyl, or $C_1$-$C_3$ alkyl optionally substituted by halo or OH. In other such embodiments, Ring A is

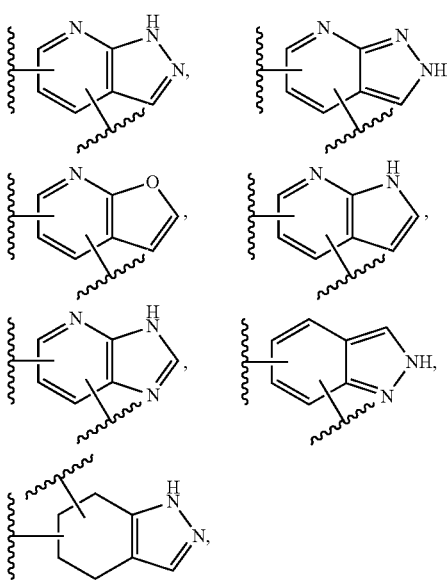

each of which is independently optionally substituted by halo, oxo, —CN, $C_3$-$C_6$ cycloalkyl, or $C_1$-$C_6$ alkyl optionally substituted by halo or OH. In some such embodiments, Ring A is

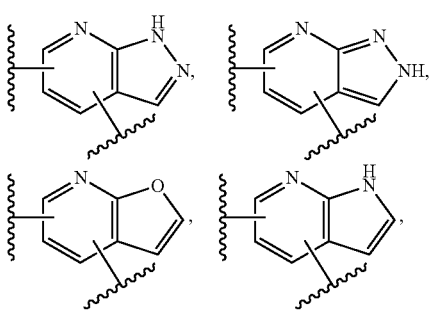

-continued

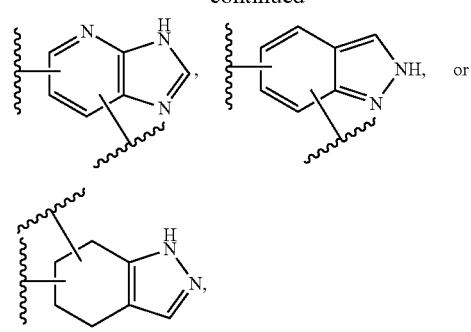

each of which is independently optionally substituted by —Cl, —F, oxo, —CN, cyclopropyl, or $C_1$-$C_3$ alkyl optionally substituted by halo or OH. In other such embodiments, Ring A is

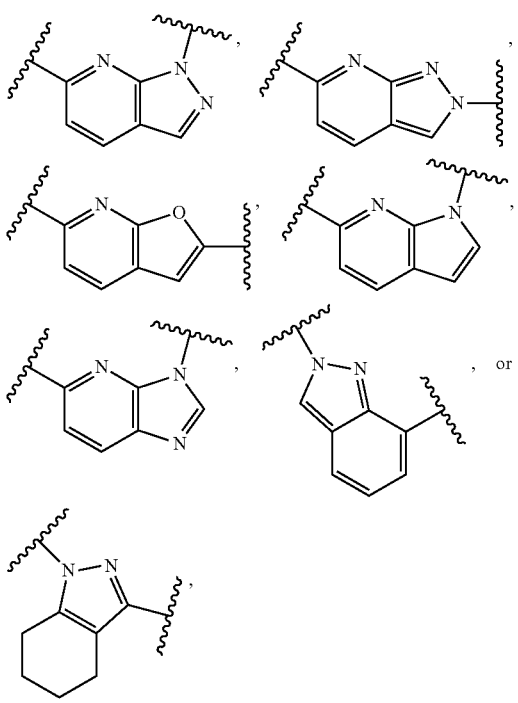

each of which is independently optionally substituted by halo, oxo, —CN, $C_3$-$C_6$ cycloalkyl, or $C_1$-$C_6$ alkyl optionally substituted by halo or OH. In some such embodiments, Ring A is

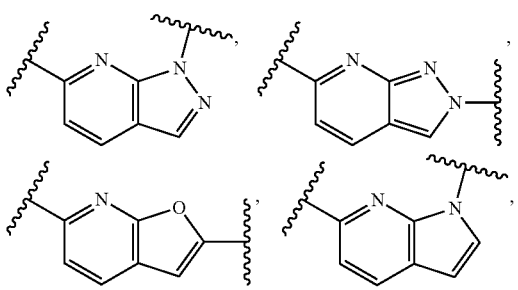

-continued

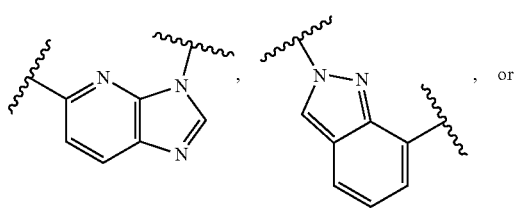

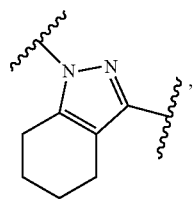

each of which is independently optionally substituted by —Cl, —F, oxo, —CN, cyclopropyl, or $C_1$-$C_3$ alkyl optionally substituted by halo or OH. In some such embodiments, Ring A is

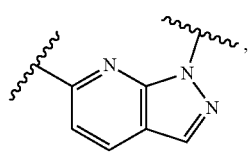

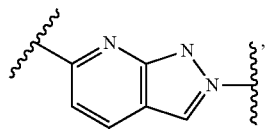

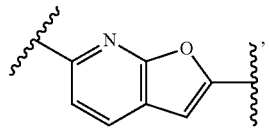

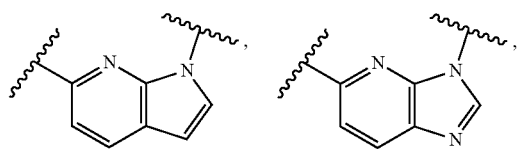

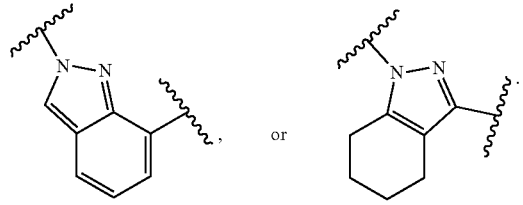

In some embodiments of a compound of Formula (I) (including subformulae thereof, if applicable) or a pharmaceutically acceptable salt thereof, Ring A is 10-membered heteroaryl, which is optionally substituted by halo, oxo, —CN, $C_3$-$C_6$ cycloalkyl, or $C_1$-$C_6$ alkyl optionally substituted by halo or OH. In some such embodiments, Ring A is 10-membered heteroaryl, which is optionally substituted by —Cl, —F, oxo, —CN, cyclopropyl, or $C_1$-$C_3$ alkyl optionally substituted by halo or OH. In other such embodiments, Ring A is

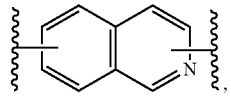

which is optionally substituted by halo, oxo, —CN, $C_3$-$C_6$ cycloalkyl, or $C_1$-$C_6$ alkyl optionally substituted by halo or OH. In some such embodiments, Ring A is

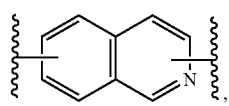

which is optionally substituted by —Cl, —F, oxo, —CN, cyclopropyl, or $C_1$-$C_3$ alkyl optionally substituted by halo or OH. In other such embodiments Ring A is

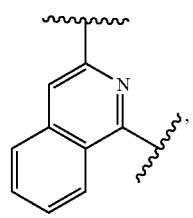 [SMILES: *c1cc2ccccc2c(*)n1]

which is optionally substituted by halo, oxo, —CN, $C_3$-$C_6$ cycloalkyl, or $C_1$-$C_6$ alkyl optionally substituted by halo or OH. In some such embodiments Ring A is

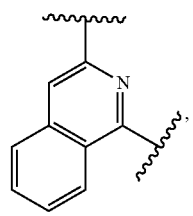 [SMILES: *c1cc2ccccc2c(*)n1]

which is optionally substituted by —Cl, —F, oxo, —CN, cyclopropyl, or $C_1$-$C_3$ alkyl optionally substituted by halo or OH. In some such embodiments, Ring A is

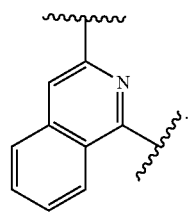 [SMILES: *c1cc2ccccc2c(*)n1]

In some embodiments of a compound of Formula (I) (including subformulae thereof, if applicable) or a pharmaceutically acceptable salt thereof, Ring A is phenylene, which is optionally substituted by halo, oxo, —CN, $C_3$-$C_6$ cycloalkyl, or $C_1$-$C_6$ alkyl optionally substituted by halo or OH. In some such embodiments, Ring A is phenylene, which is optionally substituted by —Cl, —F, oxo, —CN, cyclopropyl, or $C_1$-$C_3$ alkyl optionally substituted by halo or OH. In other such embodiments, Ring A is

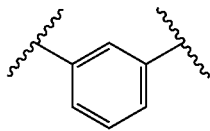 [SMILES: *c1cccc(*)c1]

which is optionally substituted by halo, oxo, —CN, $C_3$-$C_6$ cycloalkyl, or $C_1$-$C_6$ alkyl optionally substituted by halo or OH. In some such embodiments, Ring A is

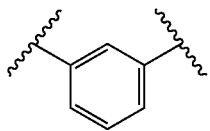 [SMILES: *c1cccc(*)c1]

which is optionally substituted by —Cl, —F, oxo, —CN, cyclopropyl, or $C_1$-$C_3$ alkyl optionally substituted by halo or OH. In some such embodiments, Ring A is

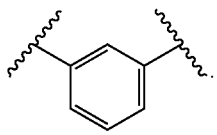 [SMILES: *c1cccc(*)c1].

In some embodiments of a compound of Formula (I) (including subformulae thereof, if applicable) or a pharmaceutically acceptable salt thereof, L is a bond. In other embodiments, L is —O—. In other embodiments, L is $C_1$-$C_6$ alkylene. In some such embodiments, L is —$CH_2$— or —$CH_2CH_2$—. In other embodiments, L is *—O—$C_1$-$C_6$ alkylene-**, wherein * represents the point of attachment to ring A and ** represents the point of attachment to ring B. In some such embodiments, L is *—O—$CH_2$—**, *—O—CH($CH_3$)—**, or *—O—$CH_2CH_2$—**. In other embodiments, L is *—$C_1$-$C_6$ alkylene-O—**. In some such embodiments, L is *—$CH_2$—O—**. In other embodiments, L is *—$NR^6$—$C_1$-$C_6$ alkylene-**. In some such embodiments, L is *—N($CH_3$)—$CH_2$—**.

In some embodiments of a compound of Formula (I) (including subformulae thereof, if applicable) or a pharmaceutically acceptable salt thereof, Ring B is $C_3$-$C_{10}$ cycloalkyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In some such embodiments, Ring B is $C_3$-$C_{10}$ cycloalkyl, which is optionally substituted by —Br, —Cl, —F, —CN, oxo, $C_1$ alkyl optionally substituted by halo, cyclopropyl, —C(O)$CH_3$, —C(O)$NH_2$, —S(O)$_2CH_3$, or phenyl. In other embodiments, Ring B is $C_6$-$C_{14}$ aryl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In some such embodiments, Ring B is $C_6$-$C_{14}$ aryl, which is optionally substituted by —Br, —Cl, —F, —CN, oxo, $C_1$ alkyl optionally substituted by halo, cyclopropyl, —C(O)$CH_3$, —C(O)$NH_2$, —S(O)$_2CH_3$, or phenyl. In other embodiments, Ring B is 4- to 12-membered heterocyclyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In some such embodiments, Ring B is 4- to 12-membered heterocyclyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In other embodiments, Ring B is 5- to 12-membered heteroaryl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In some such embodiments, Ring B is 5- to 12-membered heteroaryl, which is optionally substituted by —Br, —Cl, —F, —CN, oxo, $C_1$ alkyl optionally substituted by halo, cyclopropyl, —C(O)$CH_3$, —C(O)$NH_2$, —S(O)$_2CH_3$, or phenyl.

In some embodiments of a compound of Formula (I) (including subformulae thereof, if applicable) or a pharmaceutically acceptable salt thereof, Ring B is $C_4$ cycloalkyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In some such embodiments, Ring B is $C_4$ cycloalkyl, which is optionally substituted by —Br, —Cl, —F, —CN, oxo, $C_1$ alkyl optionally substituted by halo, cyclopropyl, —C(O)$CH_3$, —C(O)$NH_2$, —S(O)$_2CH_3$, or phenyl. In other such embodiments, Ring B is

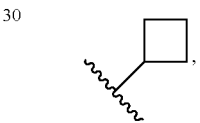, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2C_1$-$C_6$ alkyl, or phenyl. In some such embodiments, Ring B is

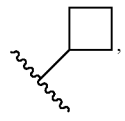, which is optionally substituted by —Br, —Cl, —F, —CN, oxo, $C_1$ alkyl optionally substituted by halo, cyclopropyl, —C(O)$CH_3$, —C(O)$NH_2$, —S(O)$_2CH_3$, or phenyl. In some such embodiments, Ring B is

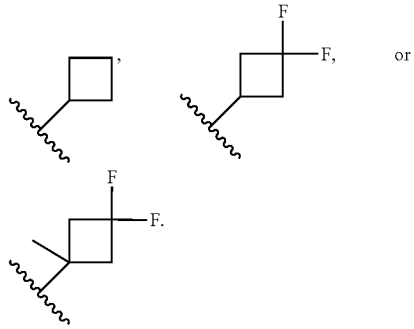

In some embodiments of a compound of Formula (I) (including subformulae thereof, if applicable) or a pharmaceutically acceptable salt thereof, Ring B is C6 cycloalkyl, which is optionally substituted by halo, —CN, oxo, $C_1$-$C_6$ alkyl optionally substituted by halo, $C_3$-$C_{10}$ cycloalkyl, —C(O)C1-C6 alkyl, —C(O)NH$_2$, —S(O)$_2$C$_1$-C$_6$ alkyl, or phenyl. In some such embodiments, Ring B is C$_6$ cycloalkyl, which is optionally substituted by —Br, —Cl, —F, —CN, oxo, C$_1$ alkyl optionally substituted by halo, cyclopropyl, —C(O)CH$_3$, —C(O)NH$_2$, —S(O)$_2$CH$_3$, or phenyl. In other such embodiments, Ring B is

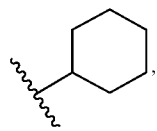 [SMILES: *C1CCCCC1]

which is optionally substituted by halo, —CN, oxo, $C_1$-$C_6$ alkyl optionally substituted by halo, $C_3$-$C_{10}$ cycloalkyl, —C(O)C$_1$-C$_6$ alkyl, —C(O)NH$_2$, —S(O)$_2$C$_1$-C$_6$ alkyl, or phenyl. In some such embodiments, Ring B is

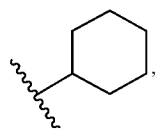 [SMILES: *C1CCCCC1]

which is optionally substituted by —Br, —Cl, —F, —CN, oxo, C$_1$ alkyl optionally substituted by halo, cyclopropyl, —C(O)CH$_3$, —C(O)NH$_2$, —S(O)$_2$CH$_3$, or phenyl. In some such embodiments, Ring B is

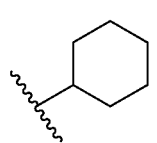 or 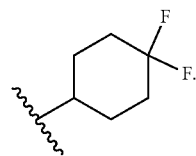

In some embodiments of a compound of Formula (I) (including subformulae thereof, if applicable) or a pharmaceutically acceptable salt thereof, Ring B is C$_9$ cycloalkyl, which is optionally substituted by halo, —CN, oxo, $C_1$-$C_6$ alkyl optionally substituted by halo, $C_3$-$C_{10}$ cycloalkyl, —C(O)C$_1$-C$_6$ alkyl, —C(O)NH$_2$, —S(O)$_2$C$_1$-C$_6$ alkyl, or phenyl. In some such embodiments, Ring B is C$_9$ cycloalkyl, which is optionally substituted by —Br, —Cl, —F, —CN, oxo, C$_1$ alkyl optionally substituted by halo, cyclopropyl, —C(O)CH$_3$, —C(O)NH$_2$, —S(O)$_2$CH$_3$, or phenyl. In other such embodiments, Ring B is

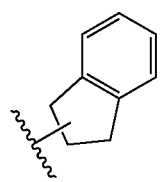 or 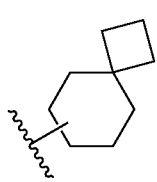, each of which is independently optionally substituted by halo, —CN, oxo, $C_1$-$C_6$ alkyl optionally substituted by halo, $C_3$-$C_{10}$ cycloalkyl, —C(O)C$_1$-C$_6$ alkyl, —C(O)NH$_2$, —S(O)$_2$C$_1$-C$_6$ alkyl, or phenyl. In some such embodiments, Ring B is

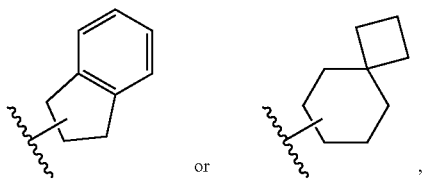

each of which is independently optionally substituted by —Br, —Cl, —F, —CN, oxo, C$_1$ alkyl optionally substituted by halo, cyclopropyl, —C(O)CH$_3$, —C(O)NH$_2$, —S(O)$_2$CH$_3$, or phenyl. In other such embodiments, Ring B is

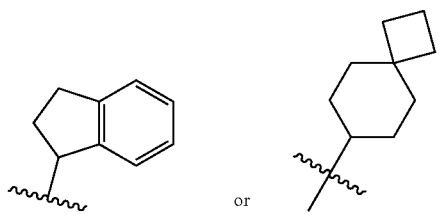

each of which is independently optionally substituted by halo, —CN, oxo, $C_1$-$C_6$ alkyl optionally substituted by halo, $C_3$-$C_{10}$ cycloalkyl, —C(O)C$_1$-C$_6$ alkyl, —C(O)NH$_2$, —S(O)$_2$C$_1$-C$_6$ alkyl, or phenyl. In some such embodiments, Ring B is

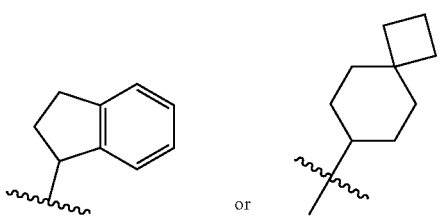

each of which is independently optionally substituted by —Br, —Cl, —F, —CN, oxo, C$_1$ alkyl optionally substituted by halo, cyclopropyl, —C(O)CH$_3$, —C(O)NH$_2$, —S(O)$_2$CH$_3$, or phenyl. In some such embodiments, Ring B is

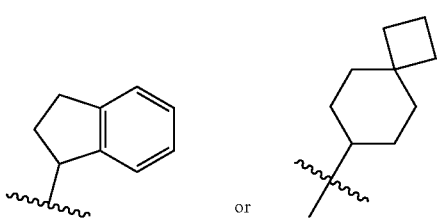

In some embodiments of a compound of Formula (I) (including subformulae thereof, if applicable) or a pharmaceutically acceptable salt thereof, Ring B is C$_{10}$ cycloalkyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is $C_{10}$ cycloalkyl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

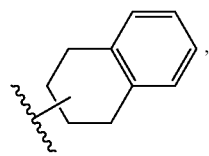, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

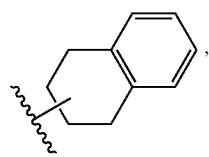, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

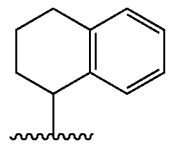 or 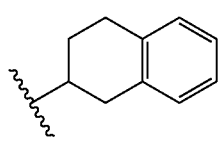, each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

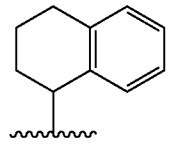 or 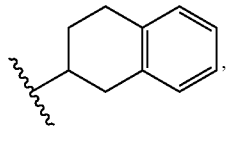, each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

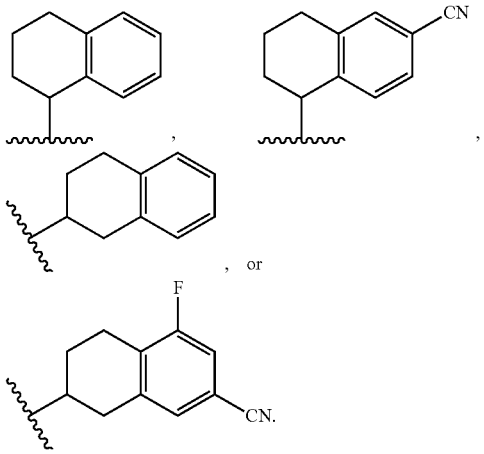

In some embodiments of a compound of Formula (I) (including subformulae thereof, if applicable) or a pharmaceutically acceptable salt thereof, Ring B is

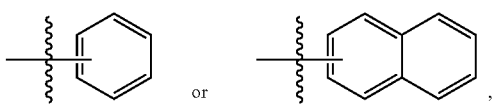

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

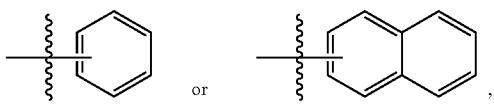

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

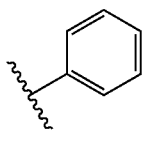 or 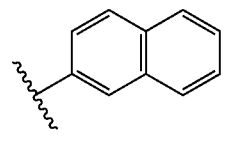, each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

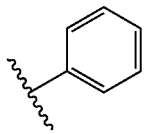 or 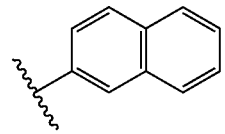, each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

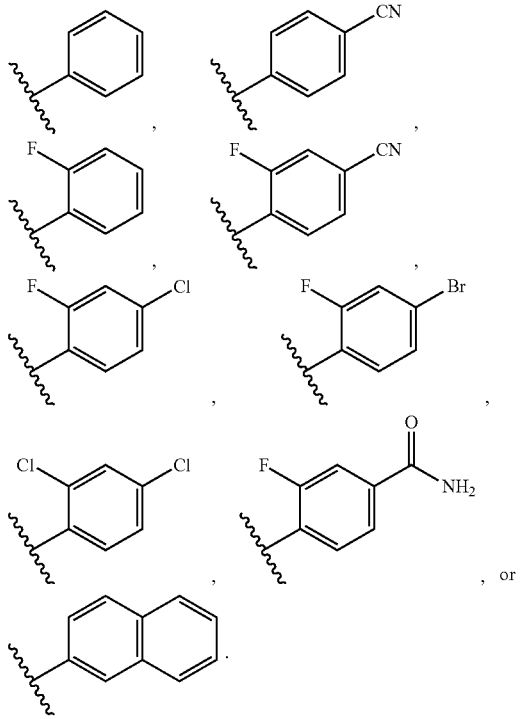

In some embodiments of a compound of Formula (I) (including subformulae thereof, if applicable) or a pharmaceutically acceptable salt thereof, Ring B is 4-membered heterocyclyl, which is optionally substituted by halo, —CN, oxo, $C_1$-$C_6$ alkyl optionally substituted by halo, $C_3$-$C_{10}$ cycloalkyl, —C(O)C$_1$-$C_6$ alkyl, —C(O)NH$_2$, —S(O)$_2$C$_1$-$C_6$ alkyl, or phenyl. In some such embodiments, Ring B is 4-membered heterocyclyl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

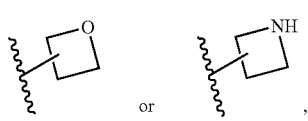

each of which is independently optionally substituted by halo, —CN, oxo, $C_1$-$C_6$ alkyl optionally substituted by halo, $C_3$-$C_{10}$ cycloalkyl, —C(O)C$_1$-$C_6$ alkyl, —C(O)NH$_2$, —S(O)$_2$C$_1$-$C_6$ alkyl, or phenyl. In some such embodiments, Ring B is

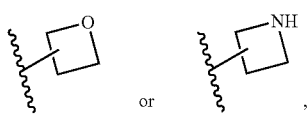

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

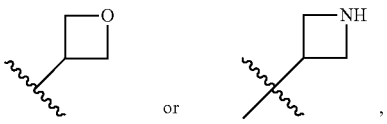 [SMILES: *C1COC1 ; *C1CNC1]

each of which is independently optionally substituted by halo, —CN, oxo, $C_1$-$C_6$ alkyl optionally substituted by halo, $C_3$-$C_{10}$ cycloalkyl, —C(O)C$_1$-$C_6$ alkyl, —C(O)NH$_2$, —S(O)$_2$C$_1$-$C_6$ alkyl, or phenyl. In some such embodiments, Ring B is

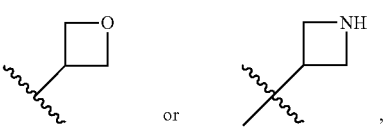 [SMILES: *C1COC1 ; *C1CNC1]

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

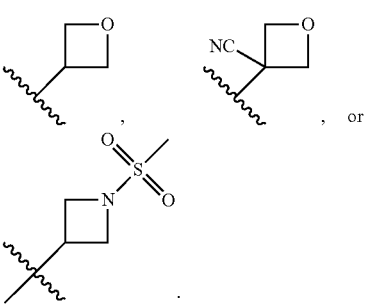

In some embodiments of a compound of Formula (I) (including subformulae thereof, if applicable) or a pharmaceutically acceptable salt thereof, Ring B is 6-membered heterocyclyl, which is optionally substituted by halo, —CN, oxo, $C_1$-$C_6$ alkyl optionally substituted by halo, $C_3$-$C_{10}$ cycloalkyl, —C(O)C$_1$-$C_6$ alkyl, —C(O)NH$_2$, —S(O)$_2$C$_1$-$C_6$ alkyl, or phenyl. In some such embodiments, Ring B is 6-membered heterocyclyl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

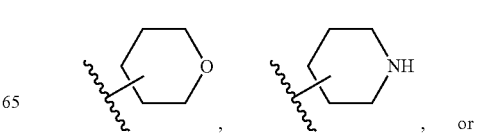

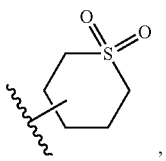

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

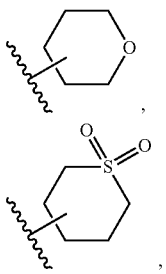

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

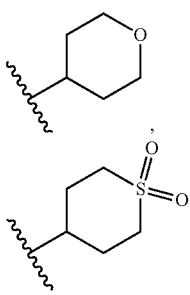

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

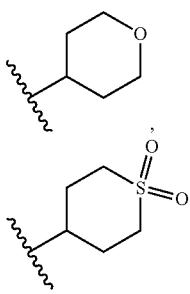

each of which is independently optionally substituted by halo, —CN, oxo, $C_1$-$C_6$ alkyl optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

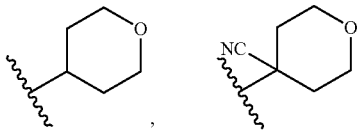

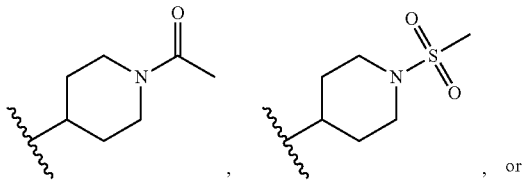, or

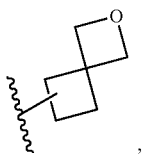

In some embodiments of a compound of Formula (I) (including subformulae thereof, if applicable) or a pharmaceutically acceptable salt thereof, Ring B is 7-membered heterocyclyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is 7-membered heterocyclyl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

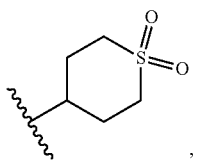

which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

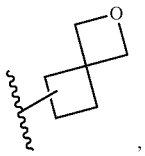

which is optionally substituted by halo, —CN, oxo, $C_1$-$C_6$ alkyl optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

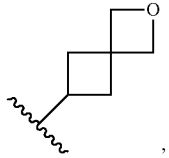 [SMILES: *C1CC2(COC2)C1]

, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

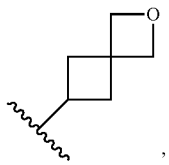 [SMILES: *C1CC2(COC2)C1]

, which is optionally substituted by halo, —CN, oxo, $C_1$-$C_6$ alkyl optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

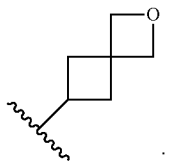 [SMILES: *C1CC2(COC2)C1]

.

In some embodiments of a compound of Formula (I) (including subformulae thereof, if applicable) or a pharmaceutically acceptable salt thereof, Ring B is 9-membered heterocyclyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is 9-membered heterocyclyl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

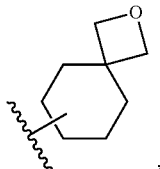

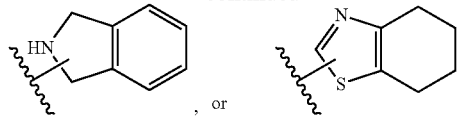

, or

.

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

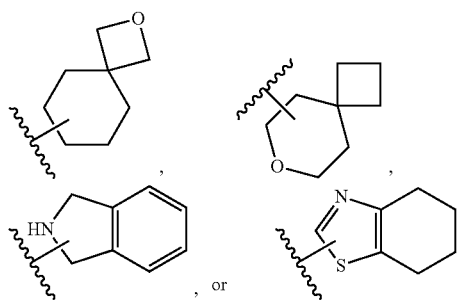

, or

, each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

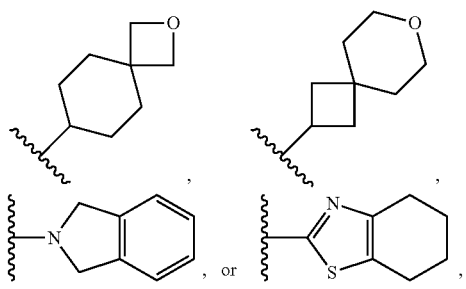

, or

, each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

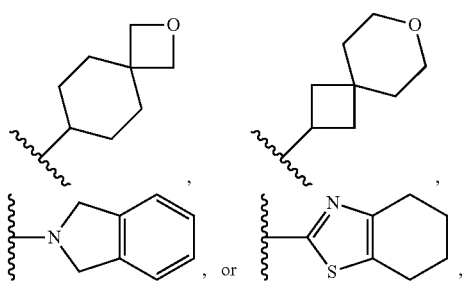

, or

, each of which is independently optionally substituted by —Br, —Cl, —F, —CN, oxo, $C_1$ alkyl optionally substituted by halo, cyclopropyl, —C(O)CH₃, —C(O)NH₂, —S(O)₂CH₃, or phenyl. In some such embodiments, Ring B is

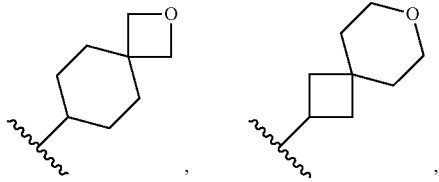

In some embodiments of a compound of Formula (I) (including subformulae thereof, if applicable) or a pharmaceutically acceptable salt thereof, Ring B is 10-membered heterocyclyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH₂, —S(O)₂$C_1$-$C_6$ alkyl, or phenyl. In some such embodiments, Ring B is 10-membered heterocyclyl, which is optionally substituted by —Br, —Cl, —F, —CN, oxo, $C_1$ alkyl optionally substituted by halo, cyclopropyl, —C(O)CH₃, —C(O)NH₂, —S(O)₂CH₃, or phenyl. In other such embodiments, Ring B is

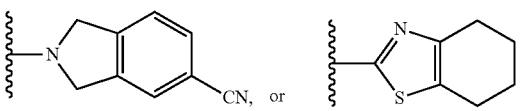

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH₂, —S(O)₂$C_1$-$C_6$ alkyl, or phenyl. In some such embodiments, Ring B is

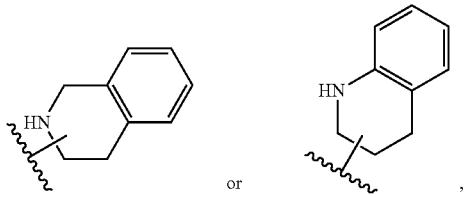

each of which is independently optionally substituted by —Br, —Cl, —F, —CN, oxo, $C_1$ alkyl optionally substituted by halo, cyclopropyl, —C(O)CH₃, —C(O)NH₂, —S(O)₂CH₃, or phenyl. In other such embodiments, Ring B is

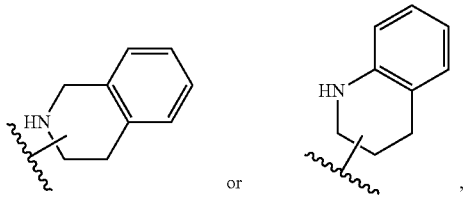

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH₂, —S(O)₂$C_1$-$C_6$ alkyl, or phenyl. In some such embodiments, Ring B is

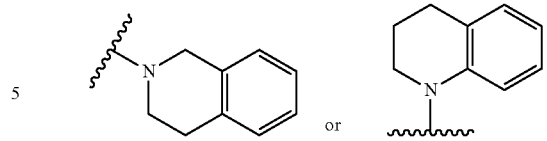

each of which is independently optionally substituted by —Br, —Cl, —F, —CN, oxo, $C_1$ alkyl optionally substituted by halo, cyclopropyl, —C(O)CH₃, —C(O)NH₂, —S(O)₂CH₃, or phenyl. In some such embodiments, Ring B is

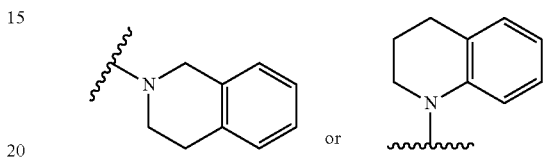

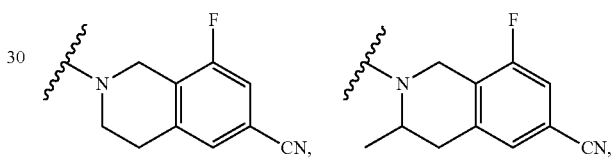

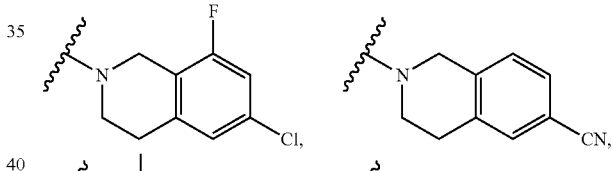

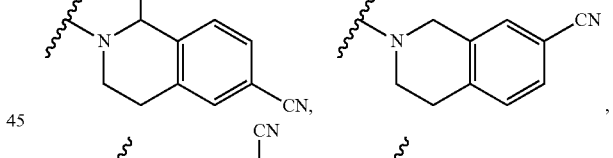

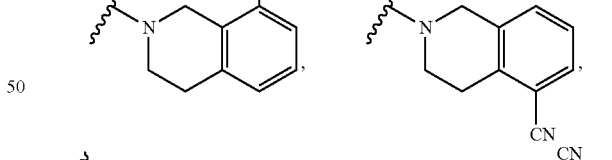

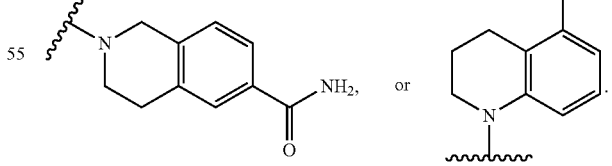

In some embodiments of a compound of Formula (I) (including subformulae thereof, if applicable) or a pharmaceutically acceptable salt thereof, Ring B is 11-membered heterocyclyl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH₂, —S(O)₂$C_1$-$C_6$ alkyl, or phenyl. In some such embodiments, Ring B is 11-membered heterocyclyl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

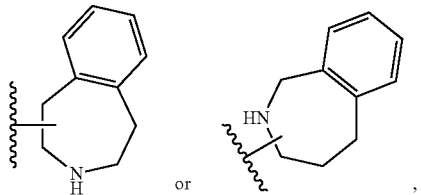

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$C$_1$-$C_6$ alkyl, or phenyl. In some such embodiments, Ring B is

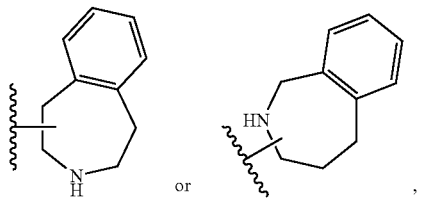

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

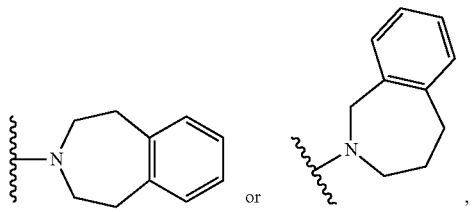 [SMILES: *N1CCc2ccccc2CC1 ; *N1CCCc2ccccc2C1]

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$C$_1$-$C_6$ alkyl, or phenyl. In some such embodiments, Ring B is

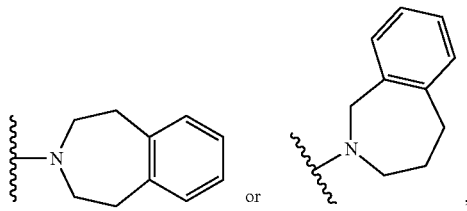 [SMILES: *N1CCc2ccccc2CC1 ; *N1CCCc2ccccc2C1]

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

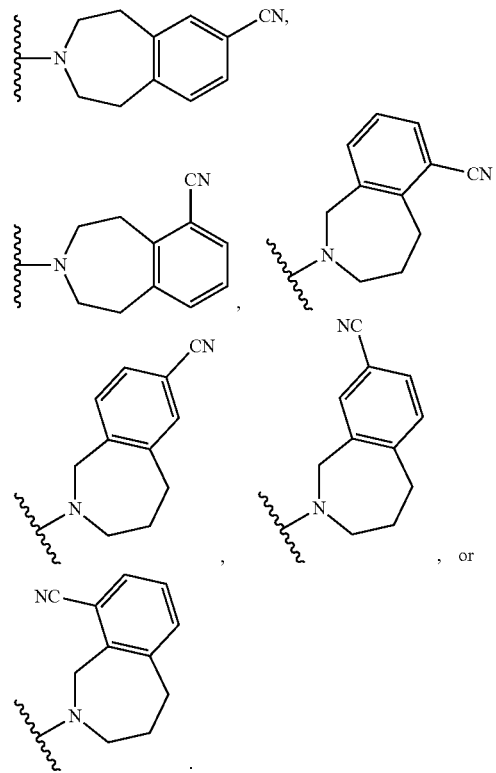

In some embodiments of a compound of Formula (I) (including subformulae thereof, if applicable) or a pharmaceutically acceptable salt thereof, Ring B is 5-membered heteroaryl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$C$_1$-$C_6$ alkyl, or phenyl. In some such embodiments, Ring B is 5-membered heteroaryl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

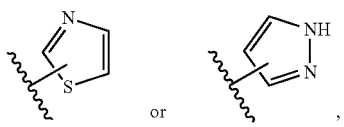

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$C$_1$-$C_6$ alkyl, or phenyl. In some such embodiments, Ring B is

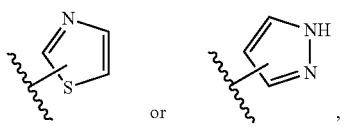

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

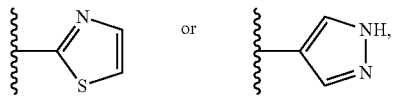 [SMILES: *c1nccs1 ; "or" ; *c1cn[nH]c1]

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

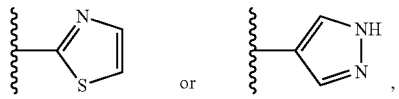 [SMILES: *c1nccs1 ; *c1cn[nH]c1]

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

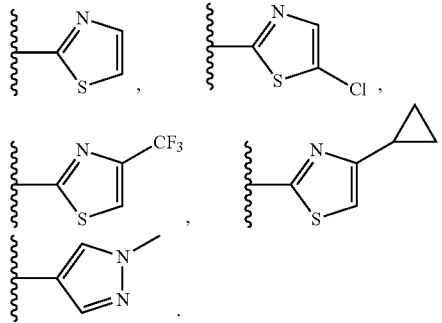

In some embodiments of a compound of Formula (I) (including subformulae thereof, if applicable) or a pharmaceutically acceptable salt thereof, Ring B is 6-membered heteroaryl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is 6-membered heteroaryl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

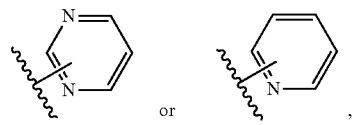

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

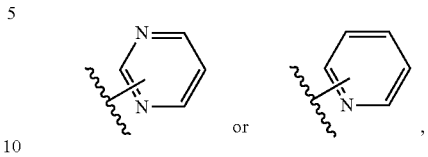

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

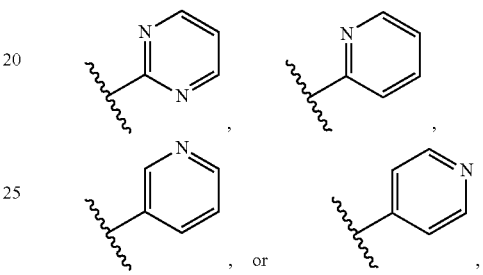

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

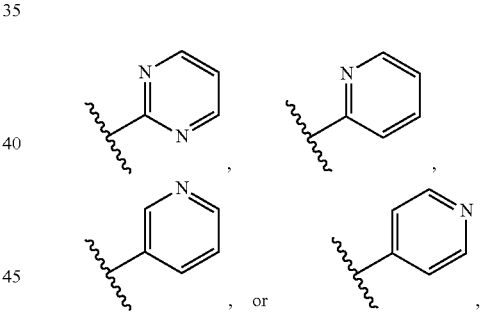

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

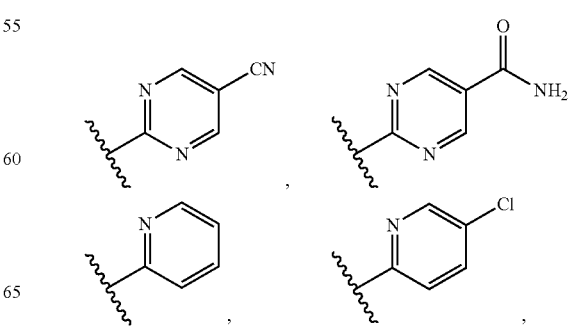

-continued

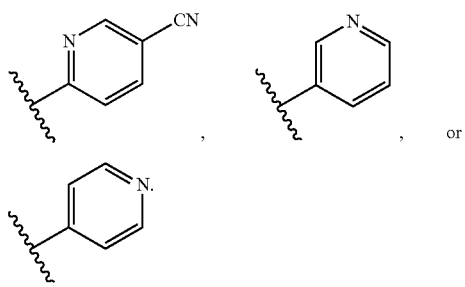

In some embodiments of a compound of Formula (I) (including subformulae thereof, if applicable) or a pharmaceutically acceptable salt thereof, Ring B is 9-membered heteroaryl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is 9-membered heteroaryl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

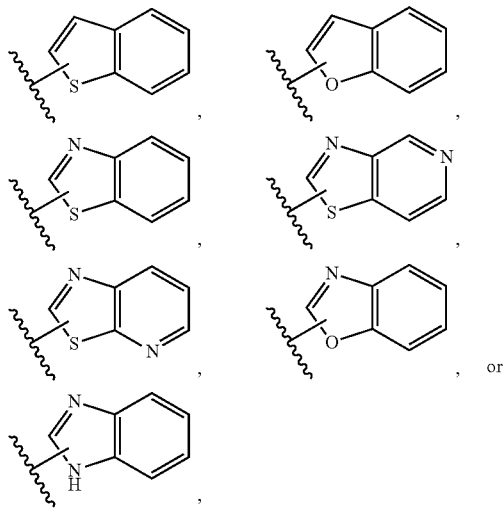

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

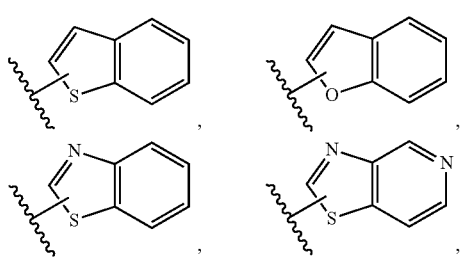

-continued

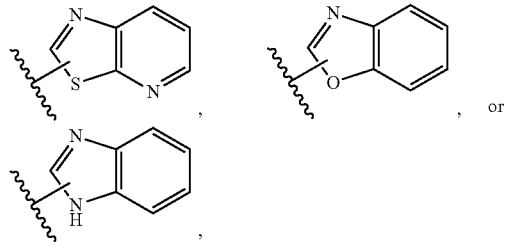

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

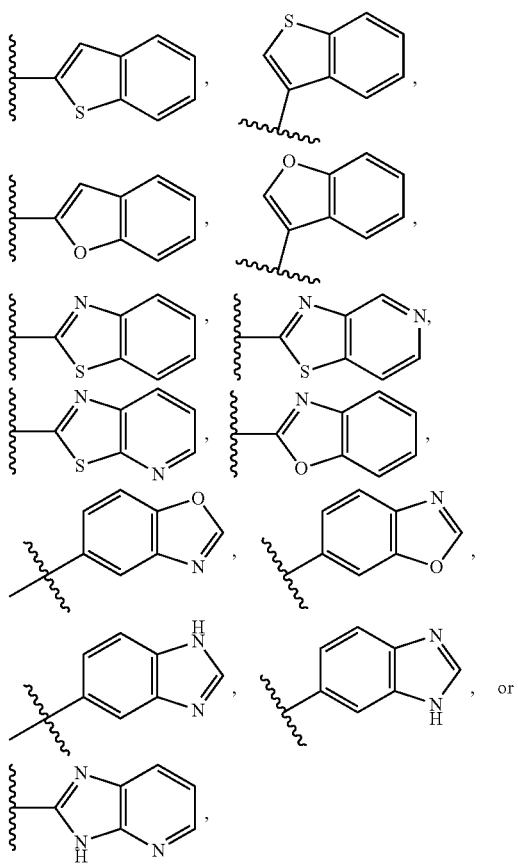

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

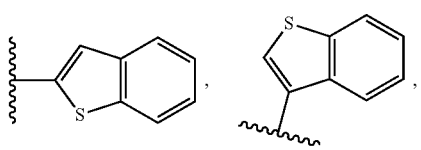

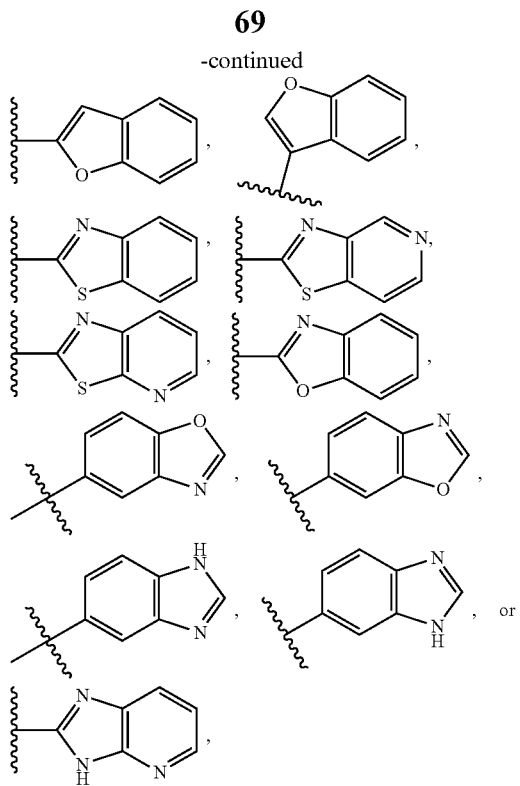

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

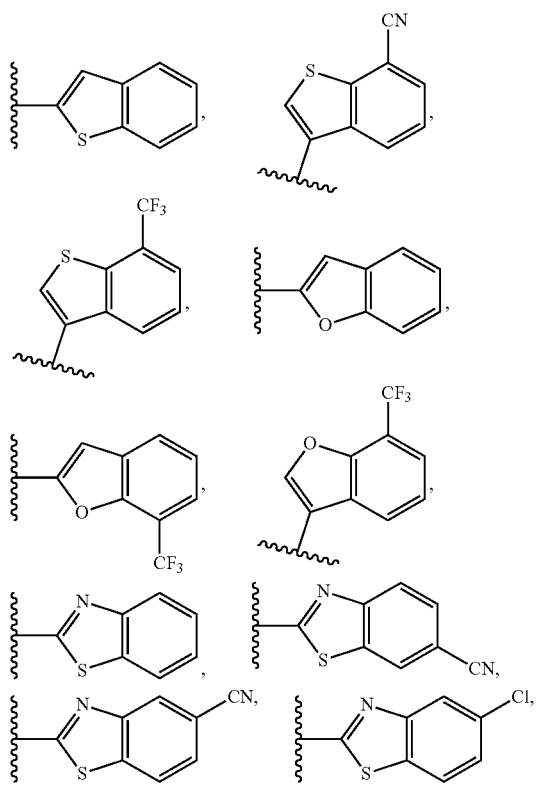

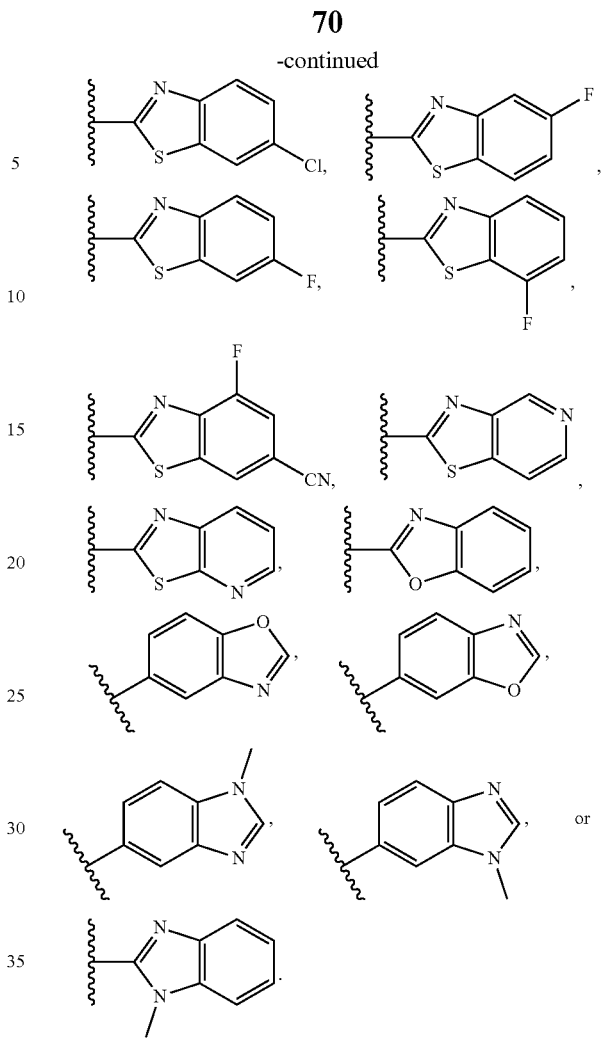

In some embodiments of a compound of Formula (I) (including subformulae thereof, if applicable) or a pharmaceutically acceptable salt thereof, Ring B is 10-membered heteroaryl, which is optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is 10-membered heteroaryl, which is optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

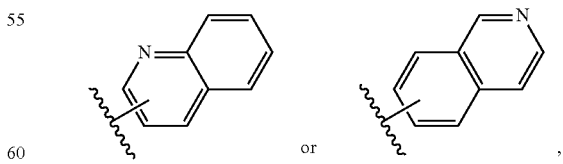

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl —C(O)NH$_2$, —S(O)$_2$$C_1$-$C_6$ alkyl, or phenyl. In some such embodiments, Ring B is

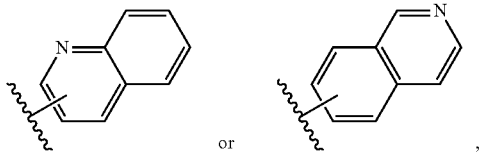

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In other such embodiments, Ring B is

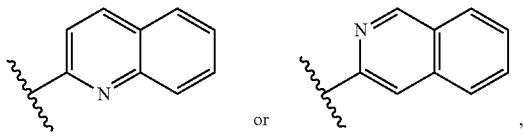 [SMILES: *c1ccc2ccccc2n1 ; *c1cc2ccccc2cn1]

each of which is independently optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, Ring B is

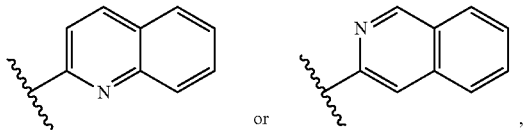 [SMILES: *c1ccc2ccccc2n1 ; *c1cc2ccccc2cn1]

each of which is independently optionally substituted by —Br, —Cl, —F, —CN, oxo, $C_1$ alkyl optionally substituted by halo, cyclopropyl, —C(O)CH$_3$, —C(O)NH$_2$, —S(O)$_2$CH$_3$, or phenyl. In some such embodiments, Ring B is

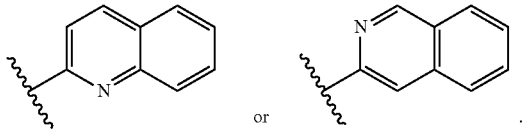 [SMILES: *c1ccc2ccccc2n1 ; *c1cc2ccccc2cn1]

In some embodiments of Formula (I) (including subformulae thereof, if applicable), Ring A is 5- to 12-membered heterocyclyl optionally substituted by halo, oxo, —CN, $C_3$-$C_6$ cycloalkyl, or $C_1$-$C_6$ alkyl optionally substituted by halo or OH; and Ring B is $C_3$-$C_{10}$ cycloalkyl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—NR$^6$—$C_1$-$C_6$ alkylene-**.

In some embodiments of Formula (I) (including subformulae thereof, if applicable), Ring A is 5- to 12-membered heterocyclyl optionally substituted by halo, oxo, —CN, $C_3$-$C_6$ cycloalkyl, or $C_1$-$C_6$ alkyl optionally substituted by halo or OH; and Ring B is $C_6$-$C_{14}$ aryl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—NR$^6$—$C_1$-$C_6$ alkylene-**.

In some embodiments of Formula (I) (including subformulae thereof, if applicable), Ring A is 5- to 12-membered heterocyclyl optionally substituted by halo, oxo, —CN, $C_3$-$C_6$ cycloalkyl, or $C_1$-$C_6$ alkyl optionally substituted by halo or OH; and Ring B is 4- to 12-membered heterocyclyl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—NR$^6$—$C_1$-$C_6$ alkylene-**.

In some embodiments of Formula (I) (including subformulae thereof, if applicable), Ring A is 5- to 12-membered heterocyclyl optionally substituted by halo, oxo, —CN, $C_3$-$C_6$ cycloalkyl, or $C_1$-$C_6$ alkyl optionally substituted by halo or OH; and Ring B is 5- to 12-membered heteroaryl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—NR$^6$—$C_1$-$C_6$ alkylene-**.

In some embodiments of Formula (I) (including subformulae thereof, if applicable), Ring A is 5- to 12-membered heteroaryl optionally substituted by halo, oxo, —CN, $C_3$-$C_6$ cycloalkyl, or $C_1$-$C_6$ alkyl optionally substituted by halo or OH; and Ring B is $C_3$-$C_{10}$ cycloalkyl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)NH$_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments of Formula (I) (including subformulae thereof, if applicable), Ring A is 5- to 12-membered heteroaryl optionally substituted by halo, oxo, —CN, $C_3$-$C_6$ cycloalkyl, or $C_1$-$C_6$ alkyl optionally substituted by halo or OH; and Ring B is $C_6$-$C_{14}$ aryl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments of Formula (I) (including subformulae thereof, if applicable), Ring A is 5- to 12-membered heteroaryl optionally substituted by halo, oxo, —CN, $C_3$-$C_6$ cycloalkyl, or $C_1$-$C_6$ alkyl optionally substituted by halo or OH; and Ring B is 4- to 12-membered heterocyclyl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments of Formula (I) (including subformulae thereof, if applicable), Ring A is 5- to 12-membered heteroaryl optionally substituted by halo, oxo, —CN, C3-C6 cycloalkyl, or C1-C6 alkyl optionally substituted by halo or OH; and Ring B is 5- to 12-membered heteroaryl optionally substituted by halo, —CN, oxo, C1-C6 alkyl optionally substituted by halo, C3-C10 cycloalkyl, —C(O)C1-C6 alkyl, —C(O)$NH_2$, —S(O)2C1-C6 alkyl, or phenyl. In some such embodiments, L is a bond. In other such embodiments, L is —O—. In other such embodiments, L is C1-C6 alkylene. In other such embodiments, L is *—O—C1-C6 alkylene-**, wherein * represents the point of attachment to ring A and ** represents the point of attachment to ring B. In other such embodiments, L is *—C1-C6 alkylene-O—**. In other such embodiments, L is *—$NR^6$—C1-C6 alkylene-**.

In some embodiments of Formula (I) (including subformulae thereof, if applicable), Ring A is $C_6$-$C_{14}$ aryl optionally substituted by halo, oxo, —CN, $C_3$-$C_6$ cycloalkyl, or $C_1$-$C_6$ alkyl optionally substituted by halo or OH; and Ring B is $C_3$-$C_{10}$ cycloalkyl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments of Formula (I) (including subformulae thereof, if applicable), Ring A is $C_6$-$C_{14}$ aryl optionally substituted by halo, oxo, —CN, $C_3$-$C_6$ cycloalkyl, or $C_1$-$C_6$ alkyl optionally substituted by halo or OH; and Ring B is $C_6$-$C_{14}$ aryl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments of Formula (I) (including subformulae thereof, if applicable), Ring A is $C_6$-$C_{14}$ aryl optionally substituted by halo, oxo, —CN, $C_3$-$C_6$ cycloalkyl, or $C_1$-$C_6$ alkyl optionally substituted by halo or OH; and Ring B is 4- to 12-membered heterocyclyl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments of Formula (I) (including subformulae thereof, if applicable), Ring A is $C_6$-$C_{14}$ aryl optionally substituted by halo, oxo, —CN, $C_3$-$C_6$ cycloalkyl, or $C_1$-$C_6$ alkyl optionally substituted by halo or OH; and Ring B is 5- to 12-membered heteroaryl optionally substituted by halo, —CN, oxo, $C_1$-$C_6$ alkyl optionally substituted by halo, $C_3$-$C_{10}$ cycloalkyl, —C(O)$C_1$-$C_6$ alkyl, —C(O)$NH_2$, —S(O)$_2$$C_1$-$C_6$ alkyl, or phenyl. In some such embodiments, L is a bond. In other such embodiments, L is —O—. In other such embodiments, L is $C_1$-$C_6$ alkylene. In other such embodiments, L is *—O—$C_1$-$C_6$ alkylene-**, wherein * represents the point of attachment to ring A and ** represents the point of attachment to ring B. In other such embodiments, L is *—$C_1$-$C_6$ alkylene-O—**. In other such embodiments, L is *—$NR^6$—$C_1$-$C_6$ alkylene-**.

In some embodiments, provided is a compound, or a pharmaceutically acceptable salt thereof, which is selected from Compound Nos. 1-18 in Table 1, below.

TABLE 1

| Cmpd No. | Structure | Name |
|---|---|---|
| 1 | 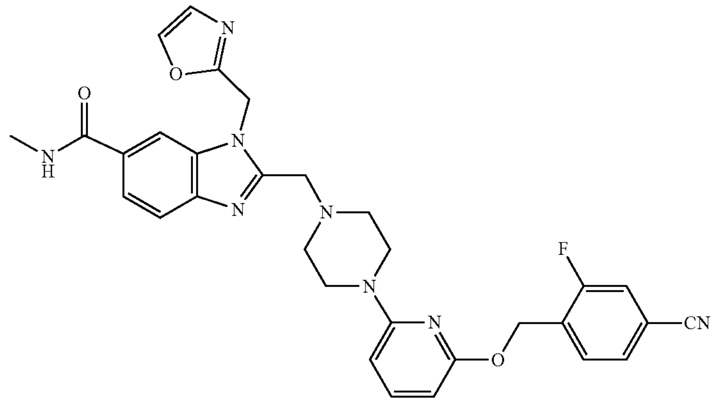 [SMILES: CNC(=O)c1ccc2nc(CN3CCN(c4cccc(OCc5ccc(C#N)cc5F)n4)CC3)n(Cc3ncco3)c2c1] | 2-((4-(6-((4-cyano-2-fluorobenzyl)oxy)pyridin-2-yl)piperazin-1-yl)methyl)-N-methyl-1-(oxazol-2-ylmethyl)-1H-benzo[d]imidazole-6-carboxamide |
| 2 | 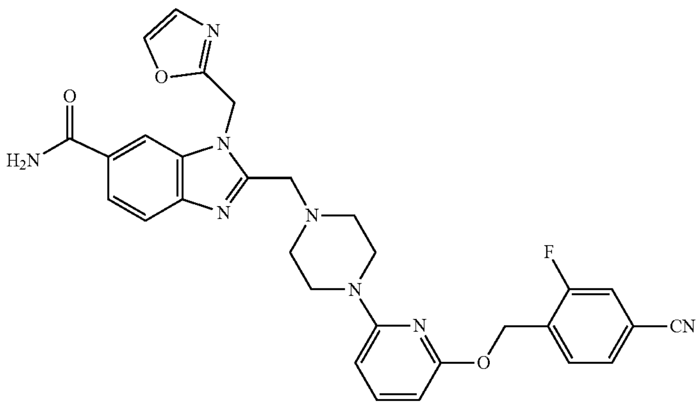 [SMILES: N#Cc1ccc(COc2cccc(N3CCN(Cc4nc5ccc(C(N)=O)cc5n4Cc4ncco4)CC3)n2)c(F)c1] | 2-((4-(6-((4-cyano-2-fluorobenzyl)oxy)pyridin-2-yl)piperazin-1-yl)methyl)-1-(oxazol-2-ylmethyl)-1H-benzo[d]imidazole-6-carboxamide |
| 3 | 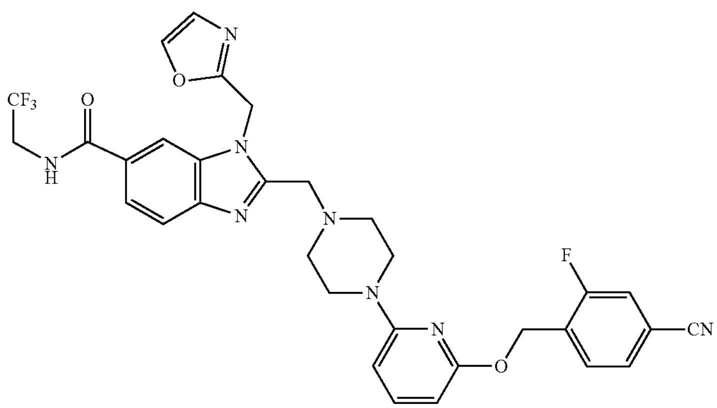 [SMILES: N#Cc1ccc(COc2cccc(N3CCN(Cc4nc5ccc(C(=O)NCC(F)(F)F)cc5n4Cc4ncco4)CC3)n2)c(F)c1] | 2-((4-(6-((4-cyano-2-fluorobenzyl)oxy)pyridin-2-yl)piperazin-1-yl)methyl)-1-(oxazol-2-ylmethyl)-N-(2,2,2-trifluoroethyl)-1H-benzo[d]imidazole-6-carboxamide |
| 4 | 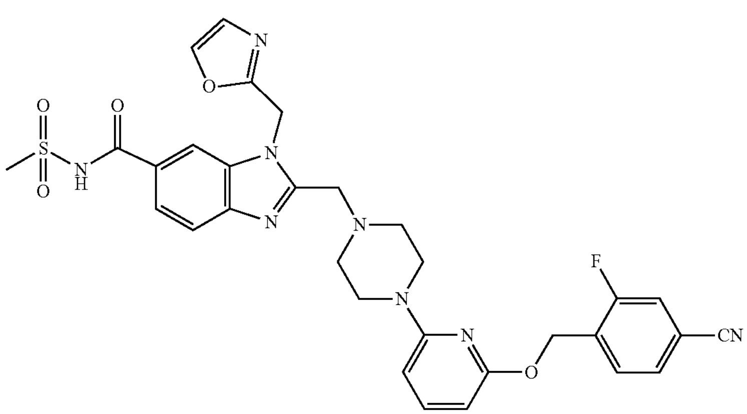 [SMILES: CS(=O)(=O)NC(=O)c1ccc2nc(CN3CCN(c4cccc(OCc5ccc(C#N)cc5F)n4)CC3)n(Cc3ncco3)c2c1] | 2-((4-(6-((4-cyano-2-fluorobenzyl)oxy)pyridin-2-yl)piperazin-1-yl)methyl)-N-(dioxo-l5-sulfanyl)-1-(oxazol-2-ylmethyl)-1H-benzo[d]imidazole-6-carboxamide |

TABLE 1-continued

| Cmpd No. | Structure | Name |
|---|---|---|
| 5 | 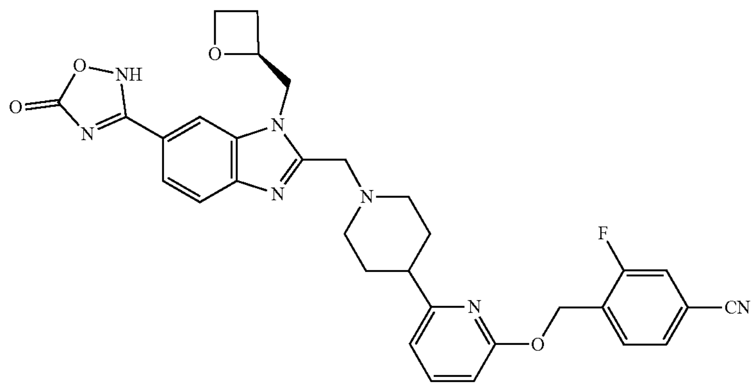 [SMILES: N#Cc1ccc(COc2cccc(C3CCN(Cc4nc5ccc(-c6nc(=O)o[nH]6)cc5n4C[C@@H]4CCO4)CC3)n2)c(F)c1] | (S)-3-fluoro-4-(((6-(1-((1-(oxetan-2-ylmethyl)-6-(5-oxo-2,5-dihydro-1,2,4-oxadiazol-3-yl)-1H-benzo[d]imidazol-2-yl)methyl)piperidin-4-yl)pyridin-2-yl)oxy)methyl)benzonitrile |
| 6 | 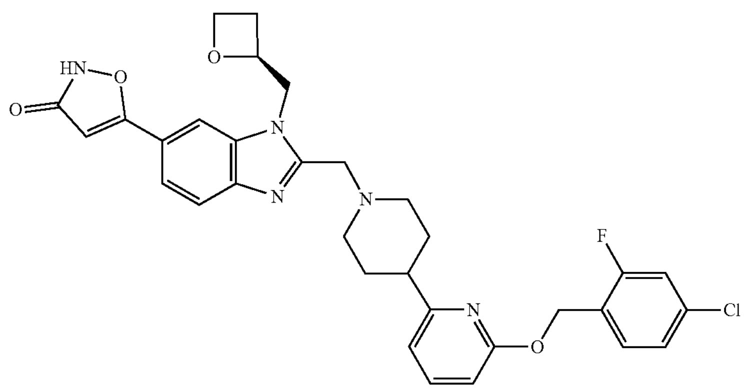 [SMILES: O=c1cc(-c2ccc3nc(CN4CCC(c5cccc(OCc6ccc(Cl)cc6F)n5)CC4)n(C[C@@H]4CCO4)c3c2)o[nH]1] | (S)-5-(2-((4-(6-((4-chloro-2-fluorobenzyl)oxy)pyridin-2-yl)piperidin-1-yl)methyl)-1-(oxetan-2-ylmethyl)-1H-benzo[d]imidazol-6-yl)isoxazol-3(2H)-one |
| 7 | 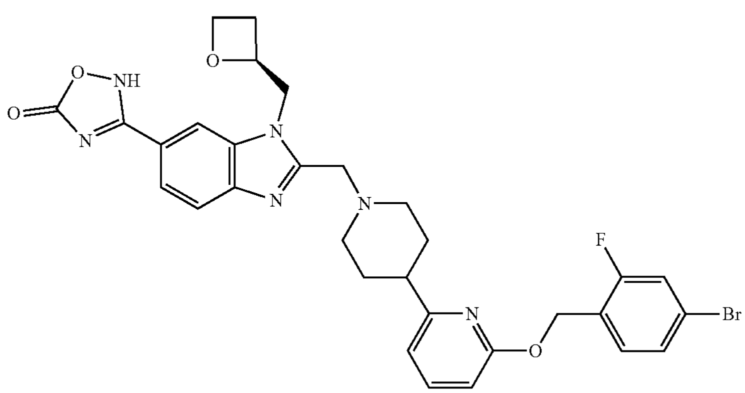 [SMILES: O=c1nc(-c2ccc3nc(CN4CCC(c5cccc(OCc6ccc(Br)cc6F)n5)CC4)n(C[C@@H]4CCO4)c3c2)[nH]o1] | (S)-3-(2-((4-(6-((4-bromo-2-fluorobenzyl)oxy)pyridin-2-yl)piperazin-1-yl)methyl)-1-(oxetan-2-ylmethyl)-1H-benzo[d]imidazol-6-yl)-1,2,4-oxadiazol-5(2H)-one |
| 8 | 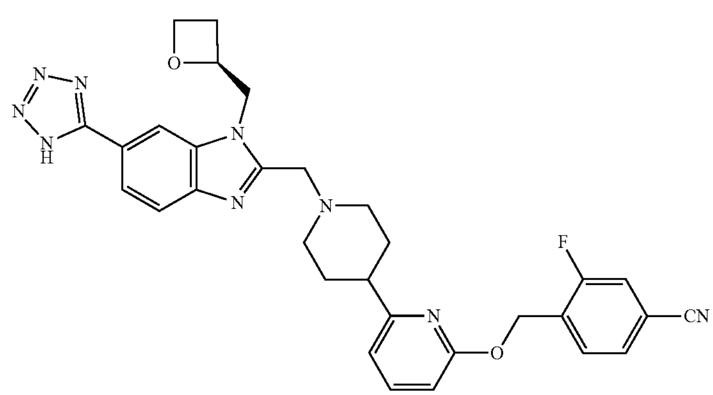 [SMILES: N#Cc1ccc(COc2cccc(C3CCN(Cc4nc5ccc(-c6nnn[nH]6)cc5n4C[C@@H]4CCO4)CC3)n2)c(F)c1] | (S)-3-fluoro-4-(((6-(1-((1-(oxetan-2-ylmethyl)-6-(1H-tetrazol-5-yl)-1H-benzo[d]imidazol-2-yl)methyl)piperidin-4-yl)pyridin-2-yl)oxy)methyl)benzonitrile |

TABLE 1-continued

| Cmpd No. | Structure | Name |
|---|---|---|
| 9 | 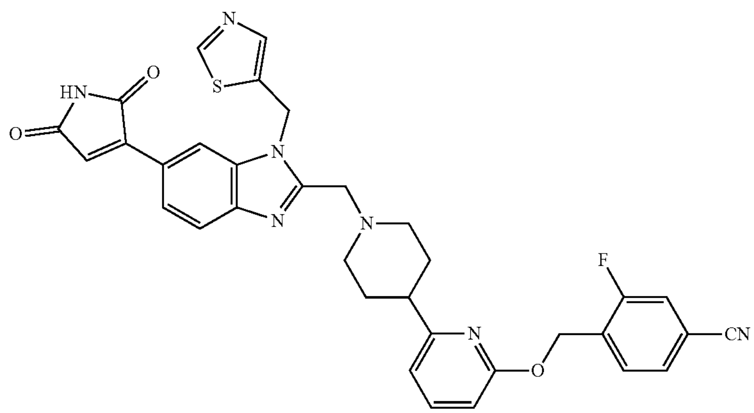 [SMILES: N#Cc1ccc(COc2cccc(C3CCN(Cc4nc5ccc(C6=CC(=O)NC6=O)cc5n4Cc4cncs4)CC3)n2)c(F)c1] | 4-(((6-(1-((6-(2,5-dioxo-2,5-dihydro-1H-pyrrol-3-yl)-1-(thiazol-5-ylmethyl)-1H-benzo[d]imidazol-2-yl)methyl)piperidin-4-yl)pyridin-2-yl)oxy)methyl)-3-fluorobenzonitrile |
| 10 | 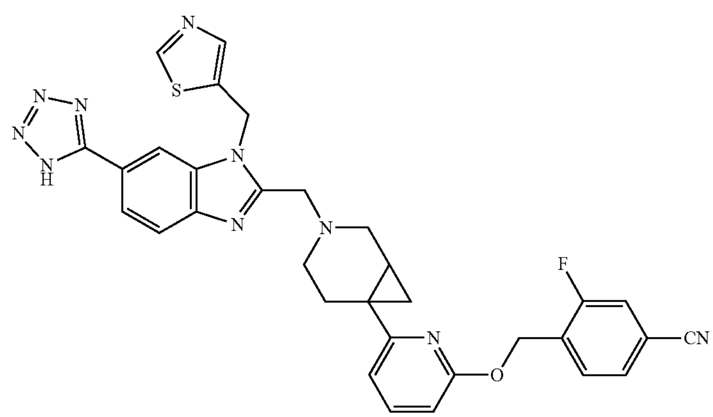 [SMILES: N#Cc1ccc(COc2cccc(C34CCN(Cc5nc6ccc(-c7nnn[nH]7)cc6n5Cc5cncs5)CC3C4)n2)c(F)c1] | 4-(((6-(3-((6-(1H-tetrazol-5-yl)-1-(thiazol-5-ylmethyl)-1H-benzo[d]imidazol-2-yl)methyl)-3-azabicyclo[4.1.0]heptan-6-yl)pyridin-2-yl)oxy)methyl)-3-fluorobenzonitrile |
| 11 | 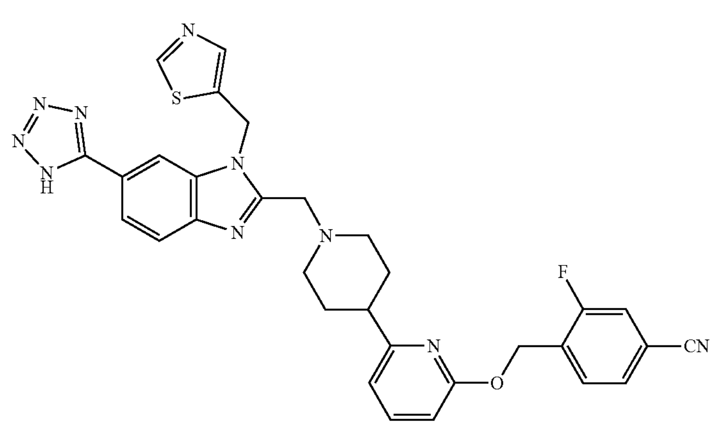 [SMILES: N#Cc1ccc(COc2cccc(C3CCN(Cc4nc5ccc(-c6nnn[nH]6)cc5n4Cc4cncs4)CC3)n2)c(F)c1] | 4-(((6-(1-((6-(1H-tetrazol-5-yl)-1-(thiazol-5-ylmethyl)-1H-benzo[d]imidazol-2-yl)methyl)piperidin-4-yl)pyridin-2-yl)oxy)methyl)-3-fluorobenzonitrile |

TABLE 1-continued

| Cmpd No. | Structure | Name |
|---|---|---|
| 12 | 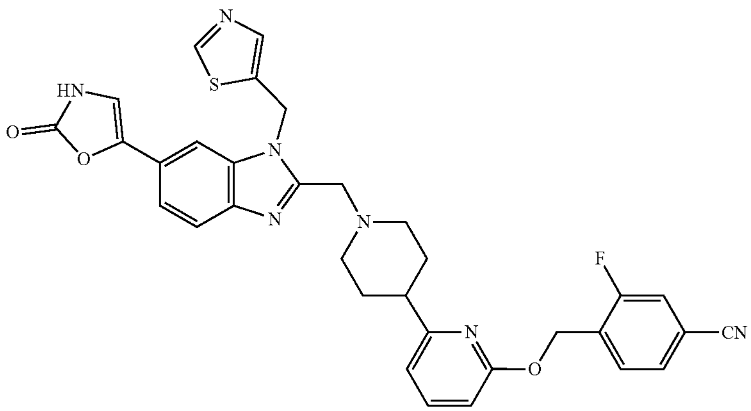 [SMILES: N#Cc1ccc(COc2cccc(C3CCN(Cc4nc5ccc(-c6c[nH]c(=O)o6)cc5n4Cc4cncs4)CC3)n2)c(F)c1] | 3-fluoro-4-(((6-(1-((6-(2-oxo-2,3-dihydrooxazol-5-yl)-1-(thiazol-5-ylmethyl)-1H-benzo[d]imidazol-2-yl)methyl)piperidin-4-yl)pyridin-2-yl)oxy)methyl)benzonitrile |
| 13 | 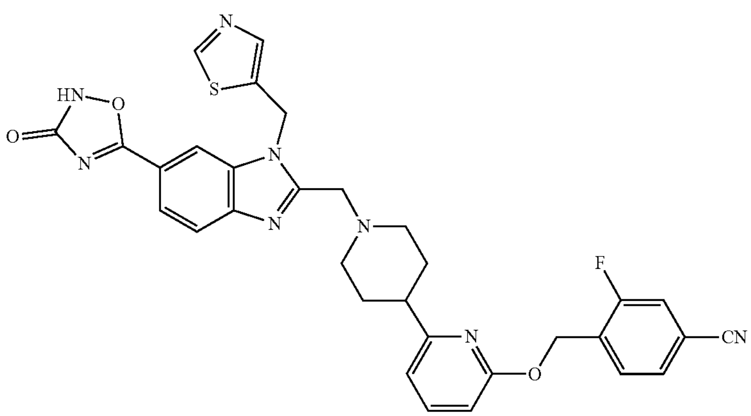 [SMILES: N#Cc1ccc(COc2cccc(C3CCN(Cc4nc5ccc(-c6nc(=O)[nH]o6)cc5n4Cc4cncs4)CC3)n2)c(F)c1] | 3-fluoro-4-(((6-(1-((6-(3-oxo-2,3-dihydro-1,2,4-oxadiazol-5-yl)-1-(thiazol-5-ylmethyl)-1H-benzo[d]imidazol-2-yl)methyl)piperidin-4-yl)pyridin-2-yl)oxy)methyl)benzonitrile |
| 14 | 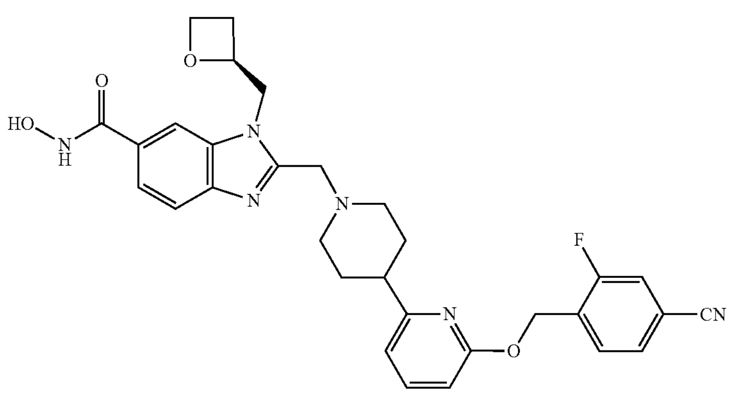 [SMILES: N#Cc1ccc(COc2cccc(C3CCN(Cc4nc5ccc(C(=O)NO)cc5n4C[C@@H]4CCO4)CC3)n2)c(F)c1] | (S)-2-((4-(6-((4-cyano-2-fluorobenzyl)oxy)pyridin-2-yl)piperidin-1-yl)methyl)-N-hydroxy-1-(oxetan-2-ylmethyl)-1H-benzo[d]imidazole-6-carboxamide |

TABLE 1-continued

| Cmpd No. | Structure | Name |
|---|---|---|
| 15 | 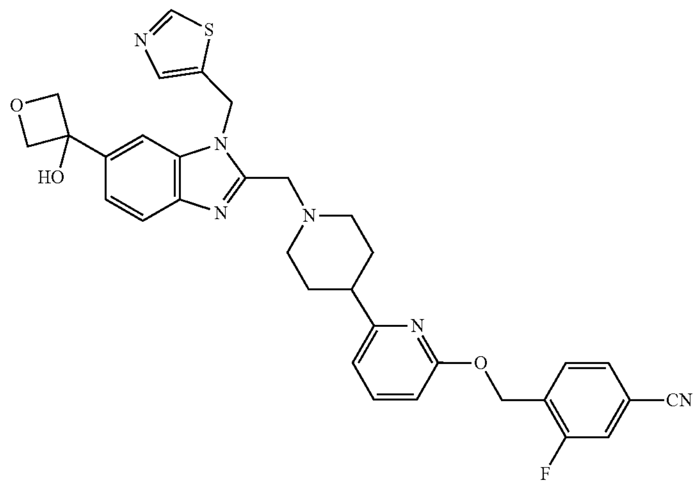 [SMILES: N#Cc1ccc(COc2cccc(C3CCN(Cc4nc5ccc(C6(O)COC6)cc5n4Cc4cncs4)CC3)n2)c(F)c1] | 3-fluoro-4-(((6-(1-((6-(3-hydroxyoxetan-3-yl)-1-(thiazol-5-ylmethyl)-1H-benzo[d]imidazol-2-yl)methyl)piperidin-4-yl)pyridin-2-yl)oxy)methyl)benzonitrile |
| 16 | 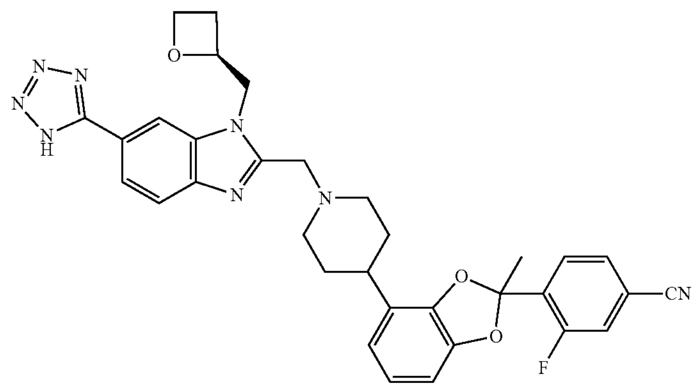 [SMILES: CC1(c2ccc(C#N)cc2F)Oc2cccc(C3CCN(Cc4nc5ccc(-c6nnn[nH]6)cc5n4C[C@@H]4CCO4)CC3)c2O1] | 3-fluoro-4-(2-methyl-4-(1-((1-(((S)-oxetan-2-yl)methyl)-6-(1H-tetrazol-5-yl)-1H-benzo[d]imidazol-2-yl)methyl)piperidin-4-yl)benzo[d][1,3]dioxol-2-yl)benzonitrile |

In another aspect, provided is a method of making a compound of Formula (I) (including subformulae thereof) or selected from the group consisting of a compound listed in Table 1, and pharmaceutically acceptable salts thereof. Compounds described herein may be prepared according to general schemes, as exemplified by the general procedures and examples. Minor variations in temperatures, concentrations, reaction times, and other parameters can be made when following the general procedures, which do not substantially affect the results of the procedures.

Also provided are compound intermediates useful in synthesis of a compound of Formula (I) (including subformulae thereof) or selected from the group consisting of a compound listed in Table 1, and pharmaceutically acceptable salts thereof. Synthesis of representative compounds and intermediates are shown in the examples below.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. Compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio, unless a specific stereochemistry is otherwise indicated. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is the enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^3H$ and $^{14}C$) are useful in compound or substrate tissue distribution study. Incorporation of heavier isotopes such as deuterium ($^2H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Pharmaceutically Acceptable Compositions and Formulations

Pharmaceutically acceptable compositions or simply "pharmaceutical compositions" of any of the compounds detailed herein are embraced by this invention. Thus, the invention includes pharmaceutical compositions comprising a compound of Formula (I) (including subformulae thereof), or a pharmaceutically acceptable salt thereof, and a pharmaceutically acceptable carrier or excipient.

In some embodiments, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compounds may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

Compounds described herein can be used in the preparation of a formulation, such as a pharmaceutical formulation, by combining the compounds as active ingredients with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington: The Science and Practice of Pharmacy, Lippincott Williams & Wilkins, 21st ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Compositions comprising two compounds utilized herein are described. Any of the compounds described herein can be formulated in a tablet in any dosage form described herein. In some embodiments, the composition comprises a compound of Formula (I) (including subformulae thereof), or a pharmaceutically acceptable salt thereof, as described herein. In some embodiments, provided herein is a dosage form comprises a therapeutically effective amount of a compound of Formula (I) (including subformulae thereof), or a pharmaceutically acceptable salt thereof. In some embodiments, the compound or a pharmaceutically acceptable salt thereof is selected from Compound Nos. 1-18 in Table 1.

Methods of Use and Uses

Compounds and compositions described herein may in some aspects be used in treatment of diseases and/or conditions described herein, for example, diseases and/or conditions mediated by GLP-1R. In some embodiments, the method of treating a disease or condition in a subject in need thereof comprises administering to the subject a therapeutically effective amount of a compound of Formula (I) (including subformulae thereof, if applicable), or a pharmaceutically acceptable salt thereof. In some embodiments, the method of treating a disease or condition in a subject in need thereof comprises administering to the subject a therapeutically effective amount of a compound selected from Compound Nos. 1-14 in Table 1, or a pharmaceutically acceptable salt thereof.

In accordance with the present application, a disease or condition to be treated and/or prevented is selected from the group consisting of cardiometabolic and associated diseases including diabetes (T1 D and/or T2DM, including pre-diabetes), idiopathic T1 D (Type 1 b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, liver diseases such as NAFLD, steatosis, NASH, fibrosis, cirrhosis, and hepatocellular carcinoma, cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, postprandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, Polycystic Ovary Syndrome and addiction (e.g., alcohol and/or drug abuse), prevention or treatment of Polycystic Ovary Syndrome and treatment of addiction (e.g., alcohol and/or drug abuse).

In some embodiments, provided herein is a method of treating a cardiometabolic disease in a subject (e.g., a human patient) in need thereof, comprising administering to the subject a therapeutically effective amount of a compound described herein, or a pharmaceutically acceptable salt thereof.

In some embodiments, provided herein is a method of treating diabetes in a subject (e.g., a human patient) in need thereof, comprising administering to the subject a therapeutically effective amount of a compound described herein, or a pharmaceutically acceptable salt thereof. Exemplary diabetes include, but are not limited to, T1 D, T2DM, pre-diabetes, idiopathic T1 D, LADA, EOD, YOAD, MODY, malnutrition-related diabetes, and gestational diabetes.

In some embodiments, provided herein is a method of treating a liver disorder in a subject (e.g., a human patient) in need thereof, comprising administering to the subject a therapeutically effective amount of a compound described herein, or a pharmaceutically acceptable salt thereof. Exemplary liver disorders include, without limitation, liver inflammation, fibrosis, and steatohepatitis. In some embodiments, the liver disorder is selected from the list consisting of primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, and oti-antitrypsin deficiency. In some embodiments, the liver disorder is selected from the list consisting of liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH). In some embodiments, the liver disorder is selected from the group consisting of liver fibrosis, alcohol induced fibrosis, steatosis, alcoholic steatosis, NAFLD, and NASH. In one embodiment, the liver disorder is NASH. In another embodiment, the liver disorder is liver inflammation. In another embodiment, the liver disorder is liver fibrosis. In another embodiment, the liver disorder is alcohol induced fibrosis. In another embodiment, the liver disorder is steatosis. In another embodiment, the liver disorder is alcoholic steatosis. In another embodiment, the liver disorder is NAFLD. In one embodiment, the treatment methods provided herein impedes or slows the progression of NAFLD to NASH. In one embodiment, the treatment methods provided herein impedes or slows the progression of NASH. NASH can progress, e.g., to one or more of liver cirrhosis, hepatic cancer, etc. In some embodiments, the liver disorder is NASH. In some embodiments, the patient has had a liver biopsy. In some embodiments, the method further comprising obtaining the results of a liver biopsy.

In accordance with the present application, a compound described herein, or a pharmaceutically acceptable salt thereof, can be administered by any suitable route in the form of a pharmaceutical composition adapted to such a route, and in a dose effective for the treatment intended. In some embodiments, it is a compound of any embodiment of Formula (I) or selected from the compounds of Table 1, or a pharmaceutically acceptable salt thereof. The compounds and/or compositions described herein may be administered orally, rectally, vaginally, parenterally, or topically.

In some embodiments, the compounds and/or compositions may be administered orally. Oral administration may involve swallowing, so that the compound enters the gastrointestinal tract, or buccal or sublingual administration may be employed by which the compound enters the bloodstream directly from the mouth.

In some embodiments, the compounds and/or compositions may be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In some embodiments, the compounds and/or compositions may be administered topically to the skin or mucosa, that is, dermally or transdermally. In some embodiments, the compounds and/or compositions may be administered intranasally or by inhalation. In some embodiments, the compounds and/or compositions may be administered rectally or vaginally. In some embodiments, the compounds and/or compositions may be administered directly to the eye or ear.

The dosage regimen for the compounds and/or compositions described herein is based on a variety of factors, including the type, age, weight, sex and medical condition of the patient; the severity of the condition; the route of administration; and the activity of the particular compound employed. Thus, the dosage regimen may vary widely. In some embodiments, the total daily dose of the compounds of the present application is typically from about 0.001 to about 100 mg/kg (i.e., mg compound per kg body weight) for the treatment of the indicated conditions discussed herein. In one embodiment, total daily dose of the compounds of the present application is from about 0.01 to about 30 mg/kg, and in another embodiment, from about 0.03 to about 10 mg/kg, and in yet another embodiment, from about 0.1 to about 3. It is not uncommon that the administration of the compounds of the present application will be repeated a plurality of times in a day (typically no greater than 4 times). Multiple doses per day typically may be used to increase the total daily dose, if desired.

For oral administration, the compounds and/or compositions described herein may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

The compounds and/or compositions described herein can be used alone, or in combination with other therapeutic agents. The administration of two or more agents "in combination" means that all of the agents are administered closely enough in time that each may generate a biological effect in the same time frame. The presence of one agent may alter the biological effects of the other agent(s). The two or more agents may be administered simultaneously, concurrently or sequentially. Additionally, simultaneous administration may be carried out by mixing the agents prior to administration or by administering the compounds at the same point in time but as separate dosage forms at the same or different site of administration.

The present application provides any of the uses, methods or compositions as defined herein wherein a compound of any embodiment of Formula (I) or selected from the compounds of Table 1 as described herein, or a pharmaceutically acceptable salt thereof, is used in combination with one or more other therapeutic agent. This would include a pharmaceutical composition comprising a compound of any embodiment of Formula (I) or selected from the compounds of Table 1, or a pharmaceutically acceptable salt thereof, as defined in any of the embodiments described herein, in admixture with at least one pharmaceutically acceptable excipient and one or more other therapeutic agent.

In some embodiments, the one or more other therapeutic agent is an anti-diabetic agent including but not limited to a biguanide (e.g., metformin), a sulfonylurea (e.g., tolbutamide, glibenclamide, gliclazide, chlorpropamide, tolazamide, acetohexamide. glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In some embodiments, the one or more other therapeutic agent is an antiobesity agent including but not limited to peptide YY or an analogue thereof, a neuropeptide Y receptor type 2 (NPYR2) agonist, a NPYR1 or NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues therof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In some embodiments, the one or more other therapeutic agent is an agent to treat NASH including but not limited to PF-05221304, an FXR agonist (e.g., obeticholic acid), a PPAR a/d agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1 R antibody, or an apoptosis signal-regulating kinase 1 (ASK1) inhibitor, including the pharmaceutically acceptable salts of the specifically named agents and the pharmaceutically acceptable solvates of said agents and salts.

Articles of Manufacture and Kits

The present disclosure further provides articles of manufacture comprising a compound, or a pharmaceutically acceptable salt thereof in accordance with the present application, a composition described herein, or one or more unit dosages described herein in suitable packaging. In certain embodiments, the article of manufacture is for use in any of the methods described herein. Suitable packaging (e.g., containers) is known in the art and includes, for example, vials, vessels, ampules, bottles, jars, flexible packaging and the like. An article of manufacture may further be sterilized and/or sealed.

The kits may be in unit dosage forms, bulk packages (e.g., multi-dose packages) or sub-unit doses. For example, kits may be provided that contain sufficient dosages of a compound, or a pharmaceutically acceptable salt thereof in accordance with the present application, a composition described herein, and/or one or more other therapeutic agent useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds/compositions described herein and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesised by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

In some embodiments, the reaction of the compounds is carried out in the presence of a suitable solvent, which is preferably inert under the respective reaction conditions.

Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about $-100°$ C. and $300°$ C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Schemes 1-10 herein.

Scheme 1
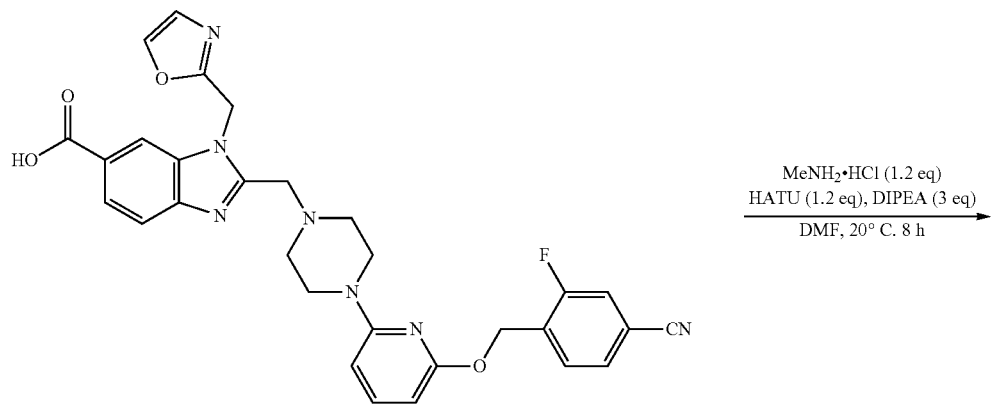
MeNH$_2$·HCl (1.2 eq)
HATU (1.2 eq), DIPEA (3 eq)
―――――――――――――――――
DMF, 20° C. 8 h
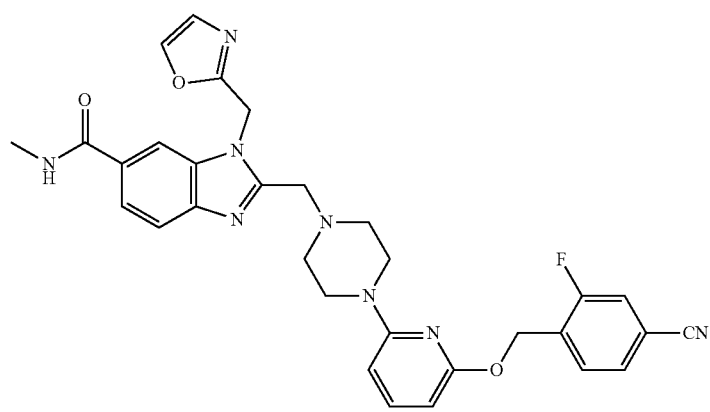
Scheme 2
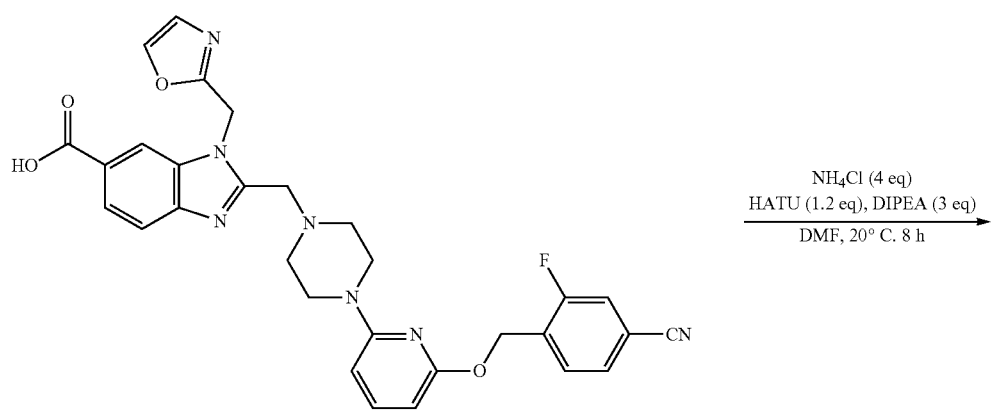
NH$_4$Cl (4 eq)
HATU (1.2 eq), DIPEA (3 eq)
―――――――――――――――――
DMF, 20° C. 8 h

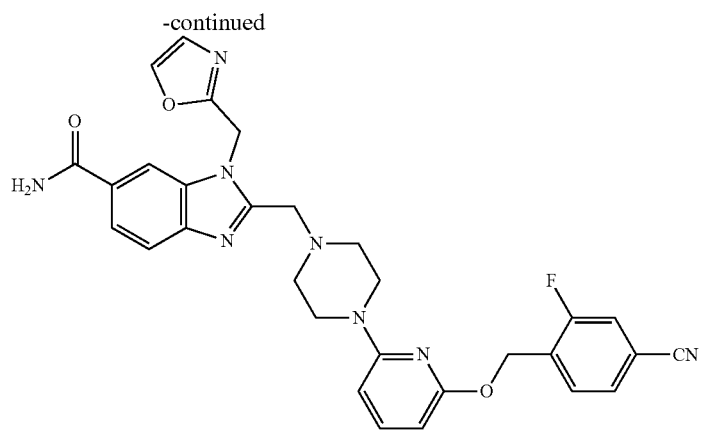
Scheme 3
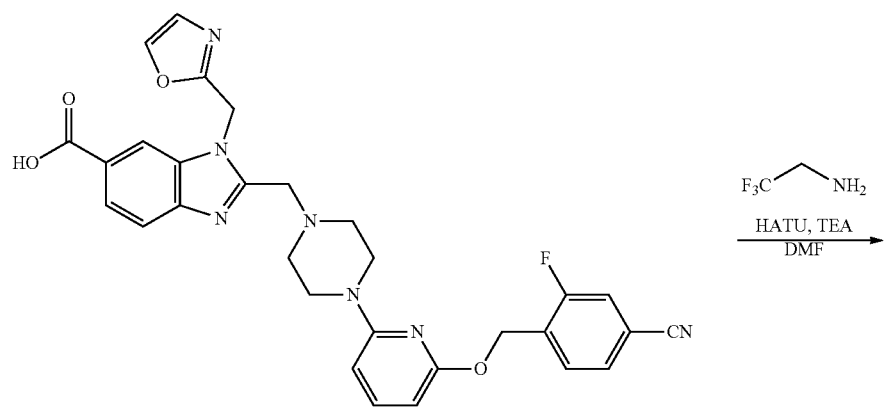
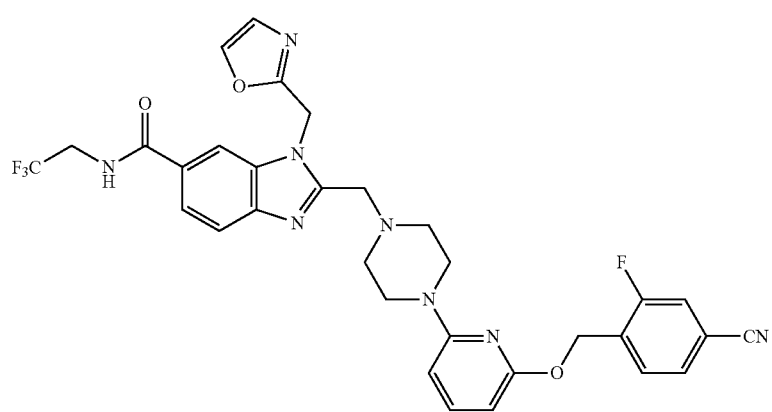

Scheme 4
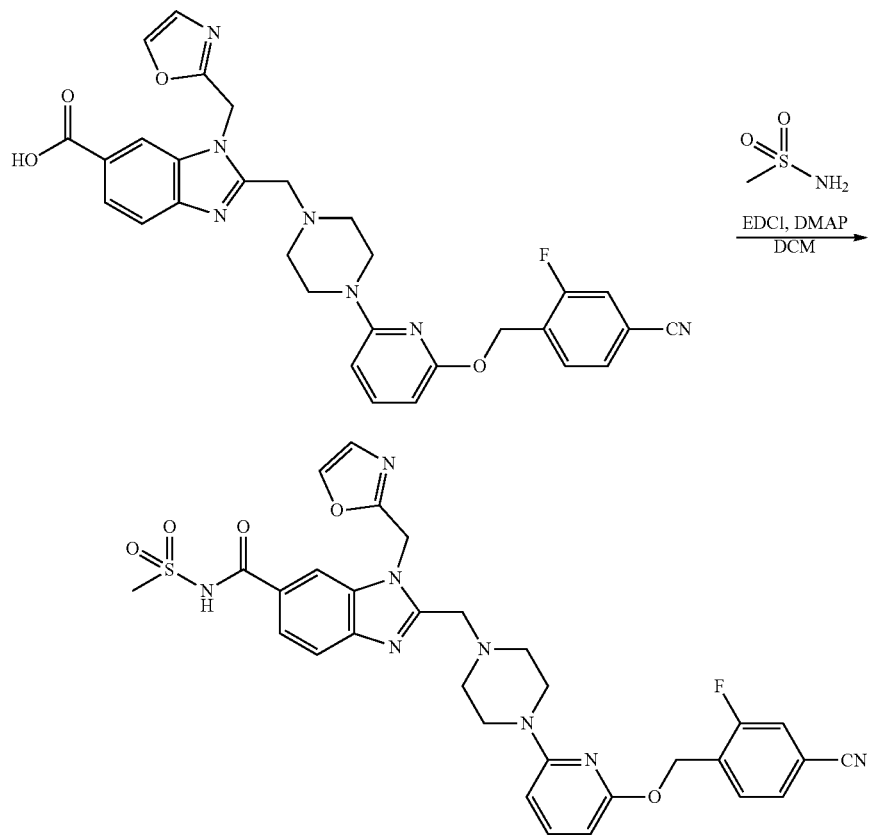
Scheme 5
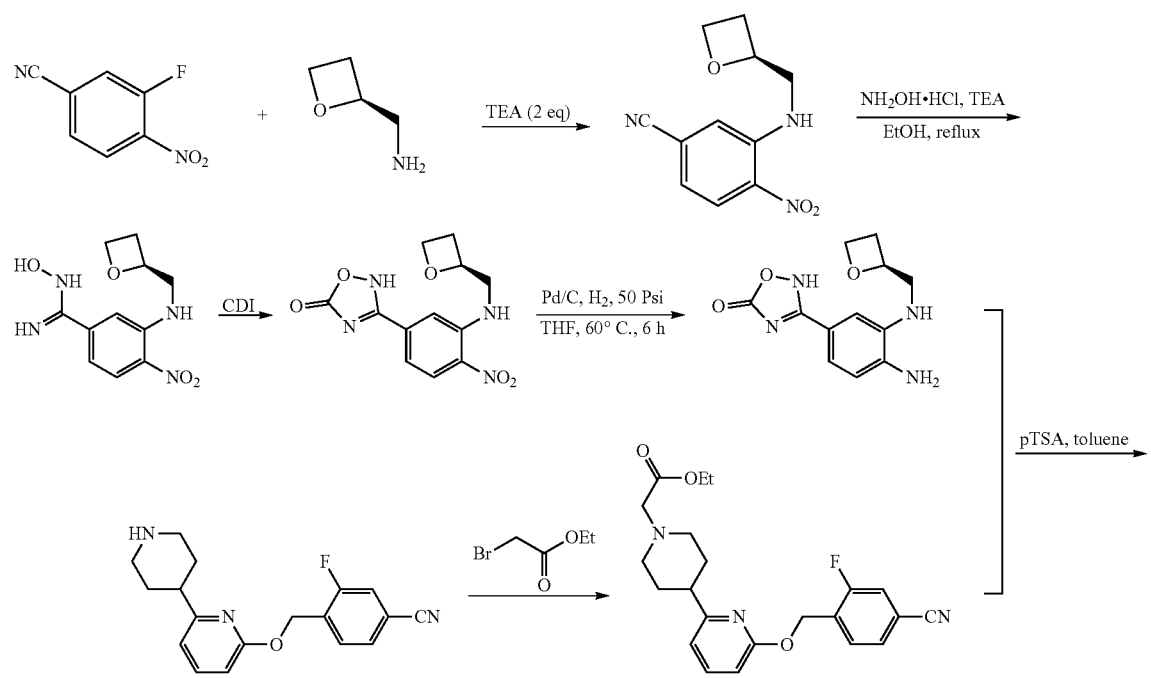

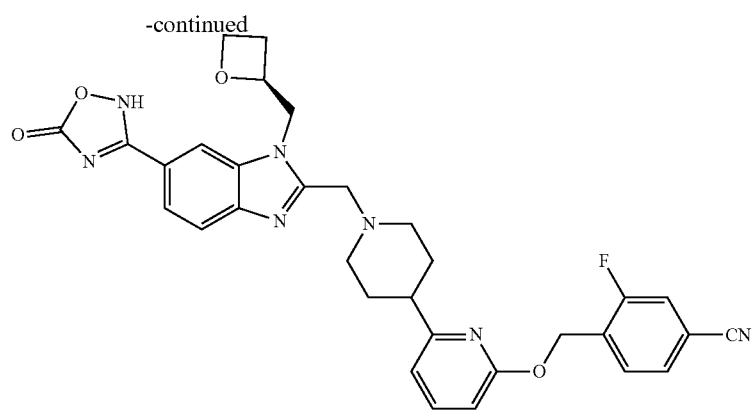
Scheme 6
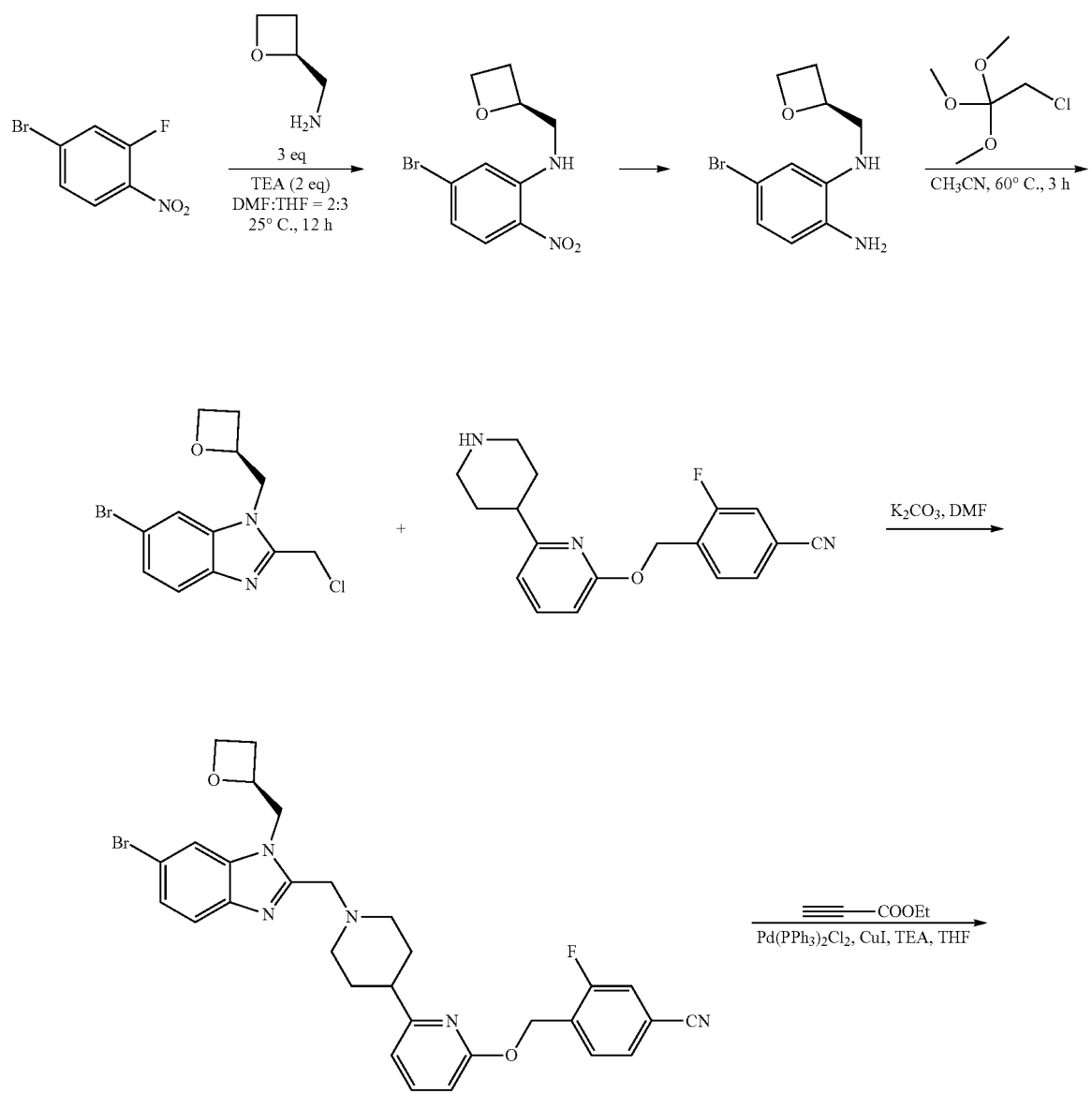

103 104
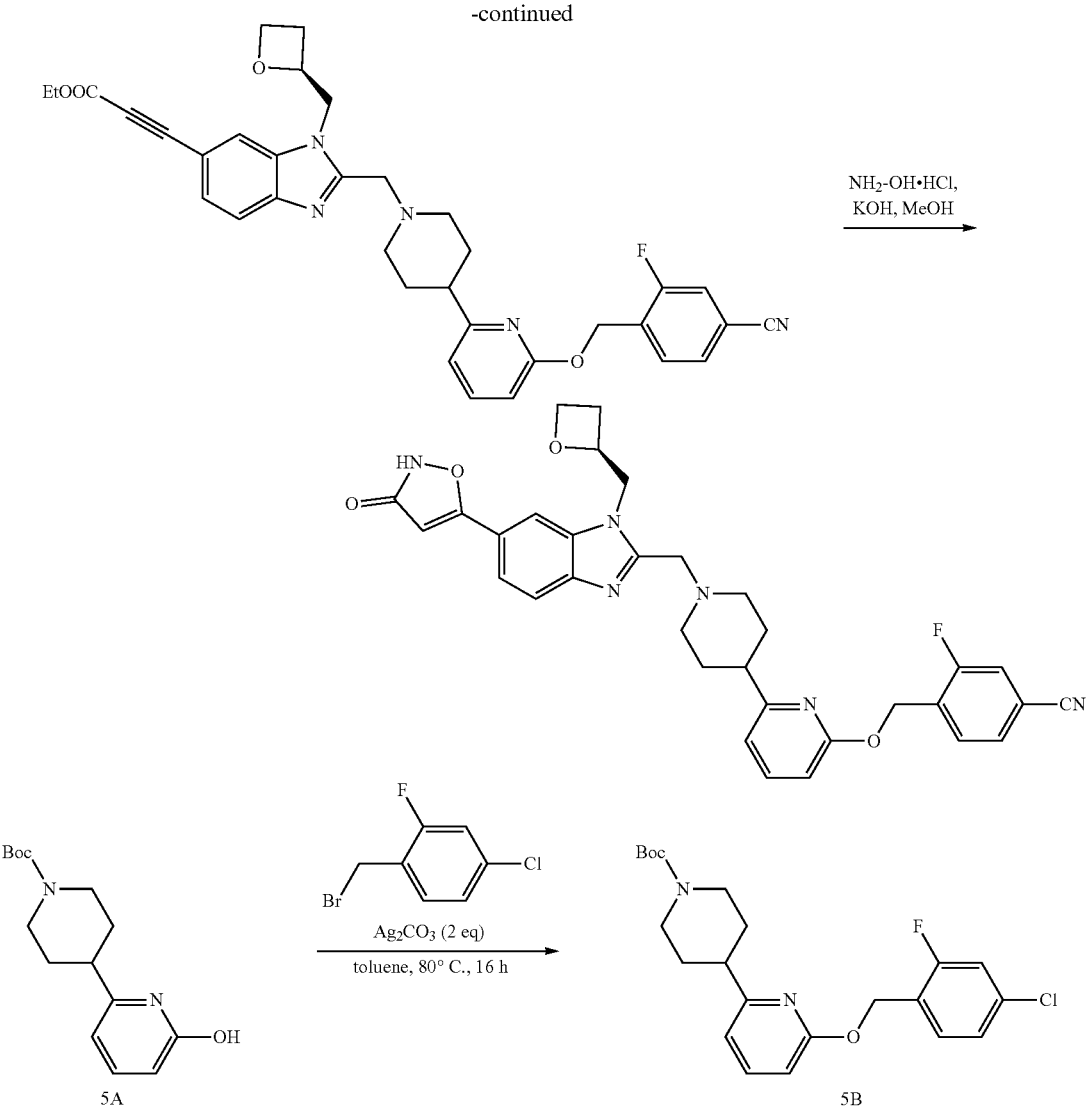
Scheme 7
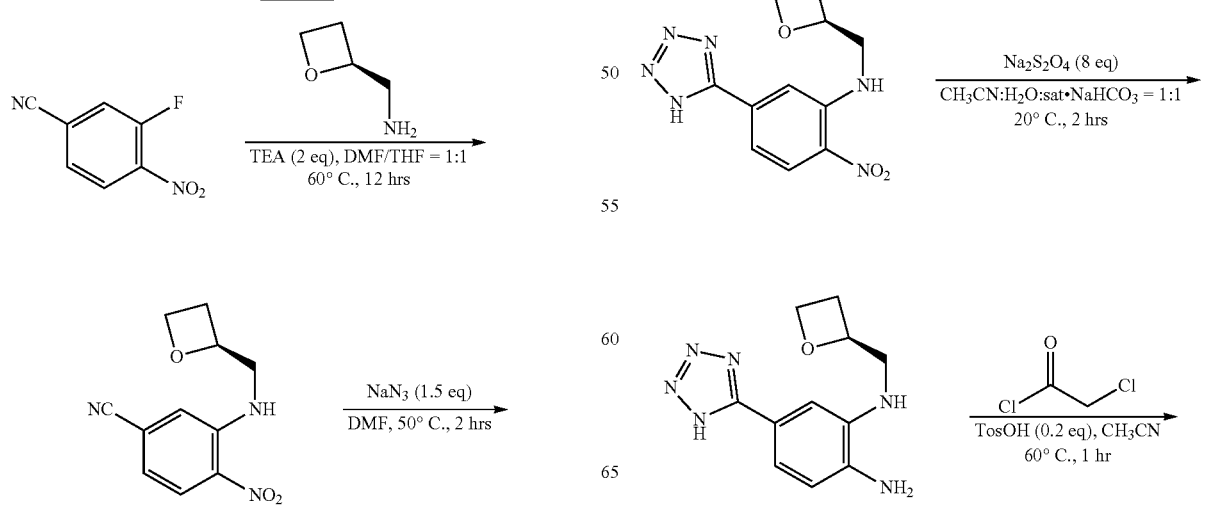

-continued
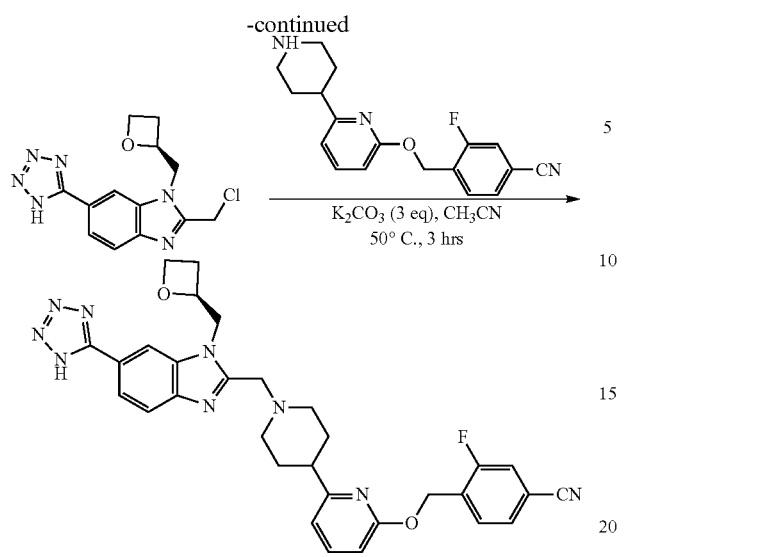
Scheme 8
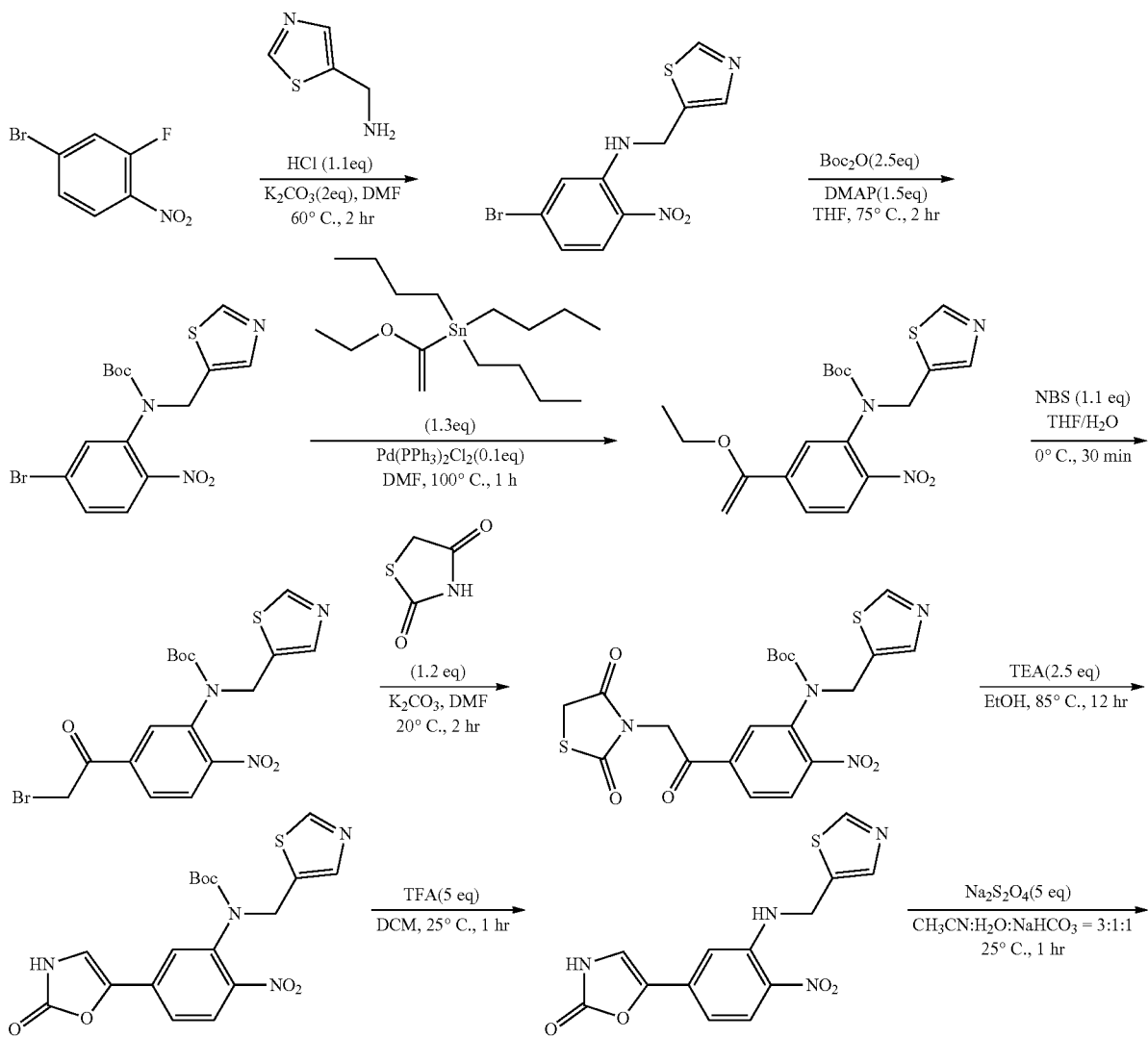

-continued
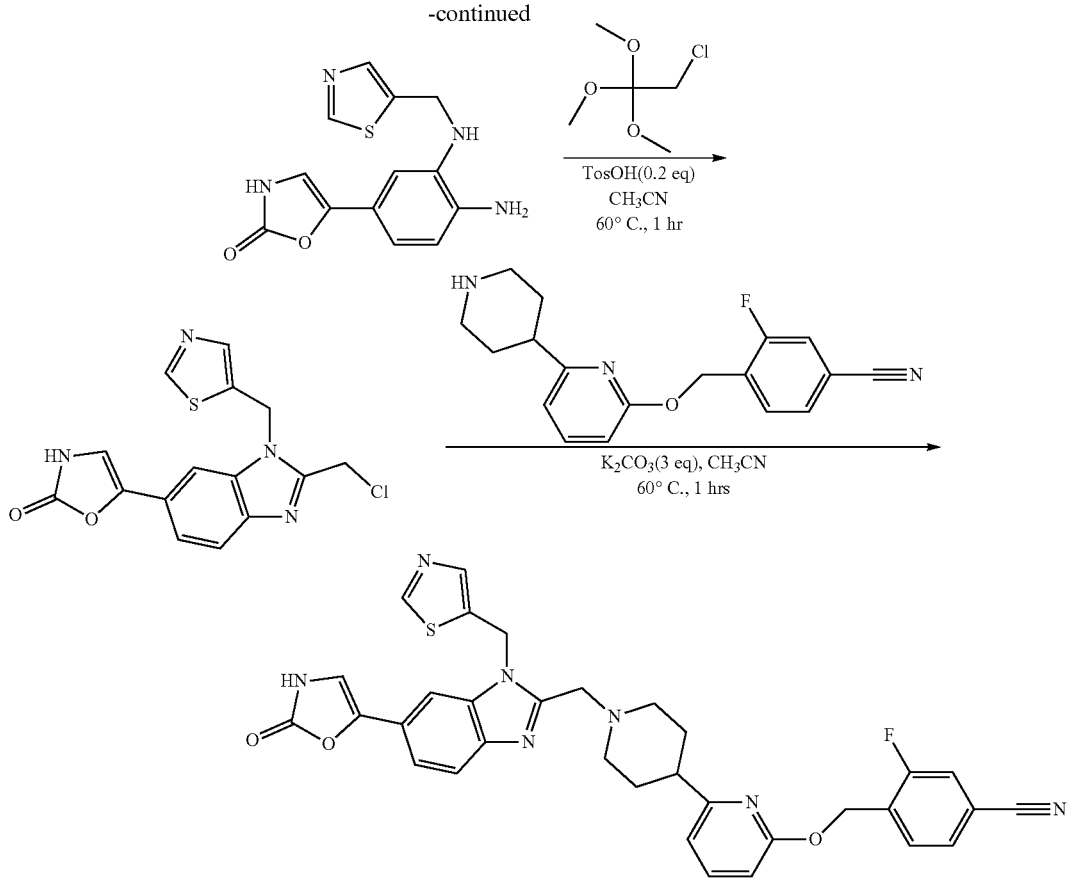
Scheme 9
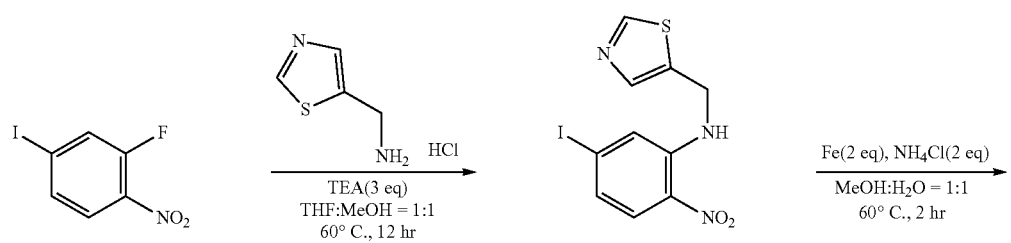
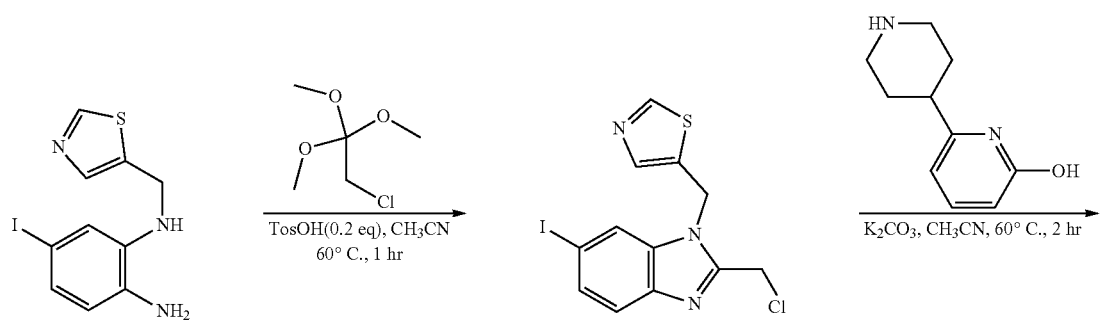

-continued
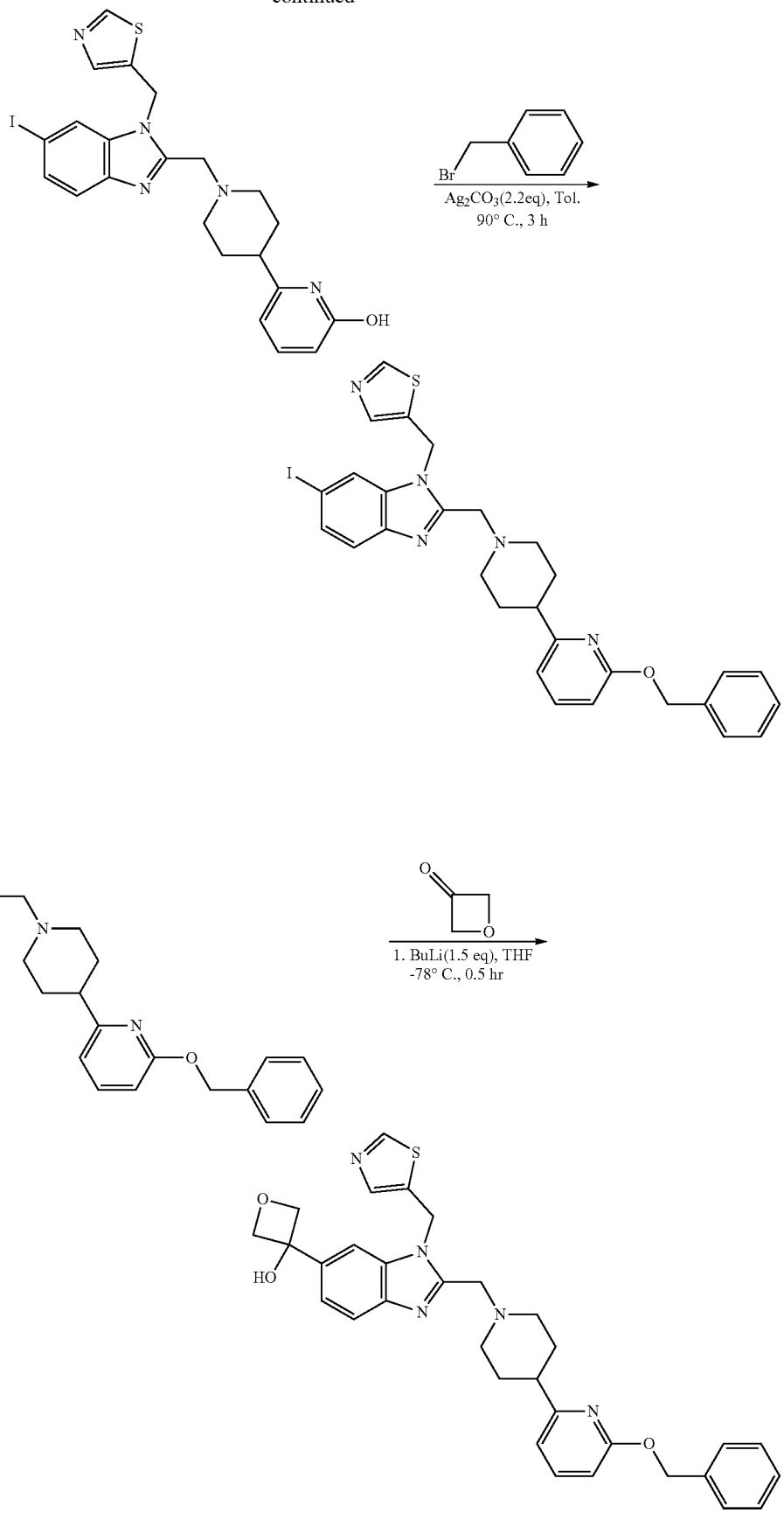

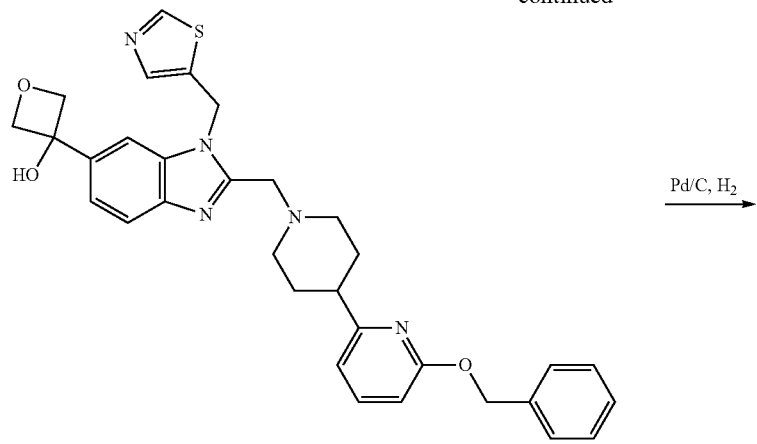
Pd/C, H₂ →
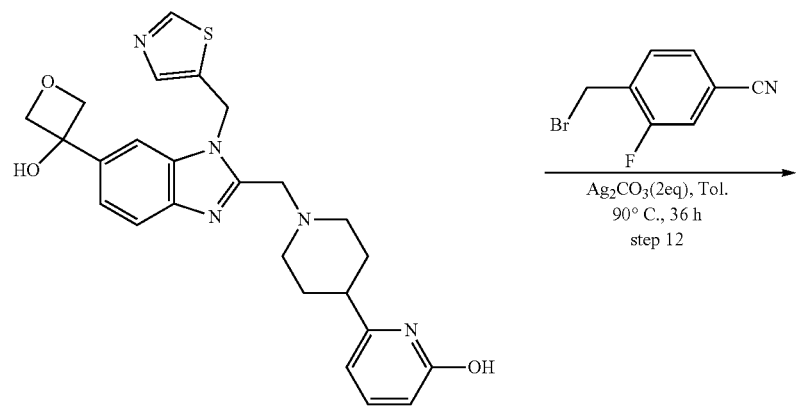
step 12
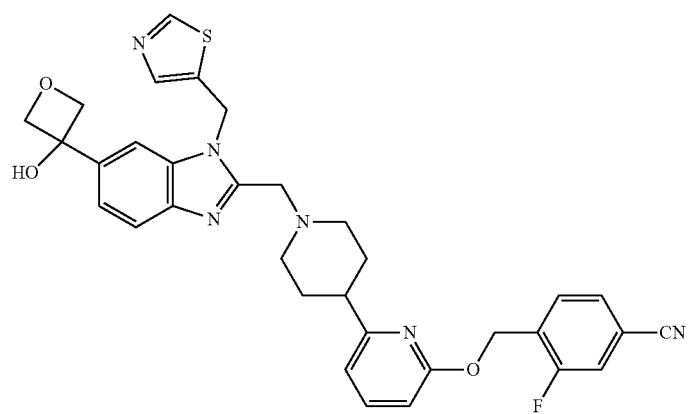

Scheme 10

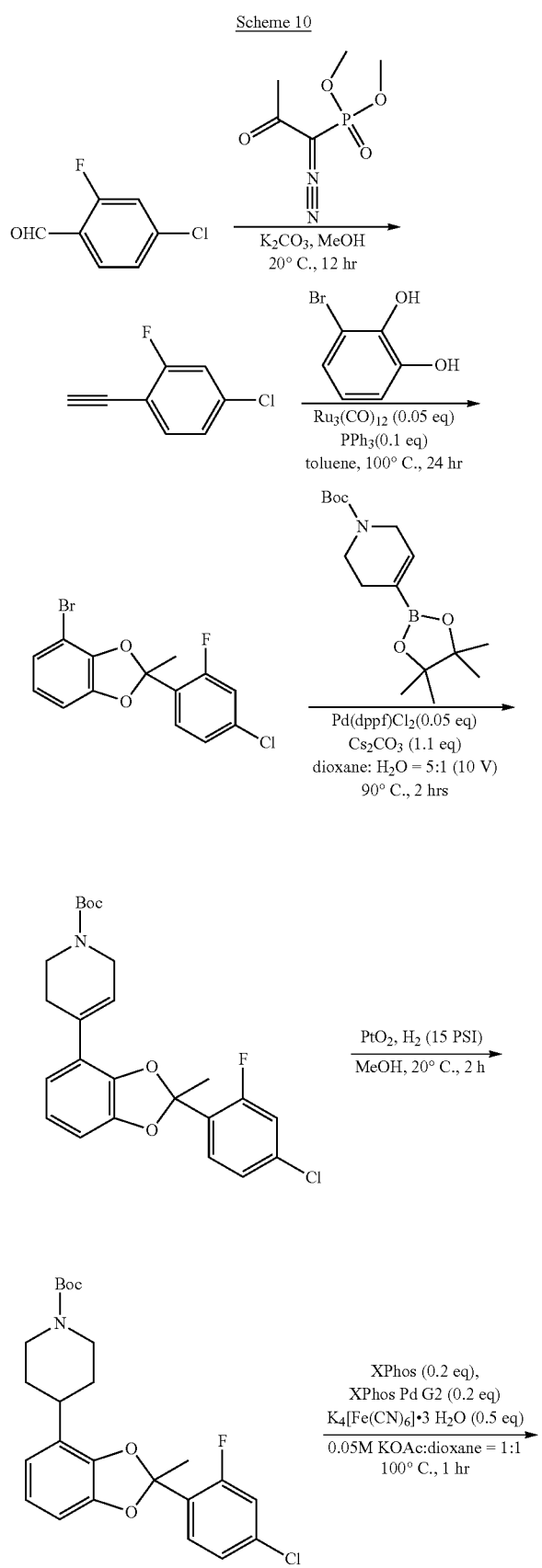

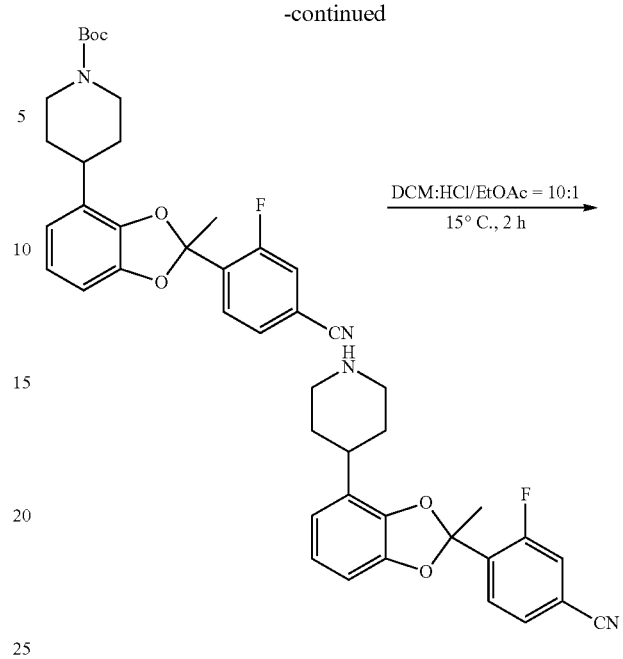

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assay is described in the Examples herein.

GLP-1R Cell Assay

Stable cell lines expressing high and low GLP-1R surface expression were generated in CHO-K1 cells transfected (Fugene 6) with a puromycin selectable DNA plasmid encoding human GLP-1R receptor (accession number: NM_002062.5) under control of an EF1A promoter. Transfected cells were seeded into 24-well plates (9,000 cells/well) containing complete medium and incubated in a humidified incubator at 37° C. with 5% carbon dioxide. After overnight incubation, medium was replaced with complete medium supplemented with puromycin (6 µg/mL) and refreshed every 2-3 days to select for stably transfected cells. Individual pools of selected cells were expanded prior to analysis for responsiveness to GLP-1 control peptide using a TR-FRET assay to detect cAMP (LANCE Ultra cAMP Assay, Perkin Elmer). Briefly, cells were collected in Versene solution, plated in 384-well plates (1,000 cells/well) and combined with serially diluted GLP-1R control peptide (10 nL) using an acoustic dispenser (ECHO). Plates were incubated for 30 minutes at 25° C. prior to the addition of EU-cAMP tracer (5 µL) and Ulight-anti-cAMP (5 µL) reagents to each well, followed by 15 minutes incubation at 25° C. TR-FRET signal was detected using an EnVision Multimode Plate Reader (excitation=320 nm; emission=615 and 655 nm). Dose-response curves were used to generate $EC_{50}$ values as a measure of responsiveness to the GLP-1R control peptide. Selected cell lines were monitored for responsiveness over multiple passages to ensure stability. CHO-K1_hGLP-1Rhigh_clone16 and CHO-K1_hGLP-1Rlow_clone10 showed consistently high and low responsiveness to GLP-1R control peptide, respectively, and were chosen for further analysis to determine relative levels of GLP-1R surface expression. Briefly, GLP-1R expression was analyzed by flow cytometry using a fluorescein-labeled Exendin-4 peptide fluorescent probe (FLEX). Cells were harvested in Versene solution and washed 3-times with PBS+0.5% BSA before incubation with FLEX reagent (10 µM) for 2 hours at room temperature. After incubation, cells were washed 3-times in PBS+0.5% BSA before final resuspension in PBS prior to analysis by flow cytometry to measure FLEX mean fluorescence intensity (MFI) as a measure of GLP-1R expression on the cell surface. Both cell lines showed higher MFI values relative to control CHO-K1 cells, confirming GLP-1R surface expression; CHO-K1_hGLP-1Rhigh_clone16 cells showed significantly higher MFI levels relative to CHO-K1-hGLP-1low_clone10 cells.

For compound testing in the CHO-K1_hGLP-1Rlow_clone10 cell line, cells were seeded in 384-well plates (1,000 cells/well). Test compounds were serially diluted in DMSO (10-point, 3-fold dilution), added to wells using an ECHO dispenser (10 nL/well) and plates were centrifuged for 1 min and agitated for 2 min at room temperature prior to 30-minute incubation at 25° C. After incubation, Eu-cAMP (5 µL) and Ulight-anti-cAMP (5 µL) reagents were added to each well, followed by centrifugation for 1 minute, agitation for 2 minutes at room temperature, and final incubation of the plates at 25° C. for 15 minutes. Plates were read using an EnVision microplate reader (excitation=320 nm; emission=615 and 655 nm). Dose-response curves were generated from duplicate wells based on percent activation calculated relative to a control GLP-1 peptide agonist that was run in parallel. $EC_{50}$ values were determined by fitting percent activation as a function of compound concentration using the Hill equation (XLfit).

Hepatic Clearance

Hepatic clearance, or the ability of the liver to extract and metabolize a drug as it passes through the liver, is controlled by hepatic blood flow (Q), protein binding (fu) and the intrinsic ability of the liver enzymes to metabolize a drug (CLint). CLint is a measure of theoretical unrestricted maximum clearance of unbound drug by an eliminating organ, in absence of blood flow or plasma protein binding limitations. This term relates to the functional reserve of the organ. The CLint may be determined in vitro using enzyme kinetics. An in vitro hepatocyte stability assay can be conducted to determine the unrestricted maximum liver clearance of unbound test agents as compared to clearance of reference standard.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which GLP-1R activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardization of in vitro and in vivo test systems for the evaluation of the effects of modulators of GLP-1R activity in laboratory animals such as dogs, rabbits, monkeys, mini-pigs, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

For exemplary purpose, neutral compounds of Formula (I) are synthesized and tested in the examples. It is understood that the neutral compounds of Formula (I) may be converted to the corresponding pharmaceutically acceptable salts of the compounds using techniques in the art (e.g., by saponification of an ester to the carboxylic acid salt, or by hydrolyzing an amide to form a corresponding carboxylic acid and then converting the carboxylic acid to a carboxylic acid salt).

Abbreviations

ACN Acetonitrile
AIBN Azobisisobutyronitrile
BOC tert-butyl carbamate
BOP (benzotriazol-1-yloxy)tris(dimethylamino)phosphonium hexafluorophosphate
BTC bis(trichloromethyl) carbonate
CDI carbonyl diimidazole
DAD diode array detector
DCM Dichloromethane
DIEA/DIPE A N,N-diisopropylethylamine
DMF N,N-dimethylformamide
DMSO Dimethylsulfoxide
EA ethyl acetate
EDCI 1-ethyl-3-(3-dimethylaminopropyl) carbodiimide
ELSD evaporative light scattering detector
ES/ESI electrospray ionisation 1-[Bis(dimethylamino)methylene]-1H-1,2,3-triazolo[4,5-b]pyridinium 3-oxid
HATU hexafluorophosphate
HOAT 1-hydroxy-7-azabenzotriazole
HOBT hydroxy benzotriazole
HPLC high-performance liquid chromatography
IPA Isopropylalcohol
LC liquid chromatography
LiHMDS lithium hexamethyl disilazide
MS mass spectrometry
NMR nuclear magnetic resonance
Py Pyridine
RT retention time
SFC supercritical fluid chromatography
TBAI tetrabutyl ammonium iodide
TEA Triethylamine
TFA trifluoroacetic acid
TFAA trifluoroacetic anhydride
THF Tetrahydrofuran
TLC thin layer chromatography
TMS tetramethyl silane
UV Ultraviolet Example 1

Preparation of Compound 1

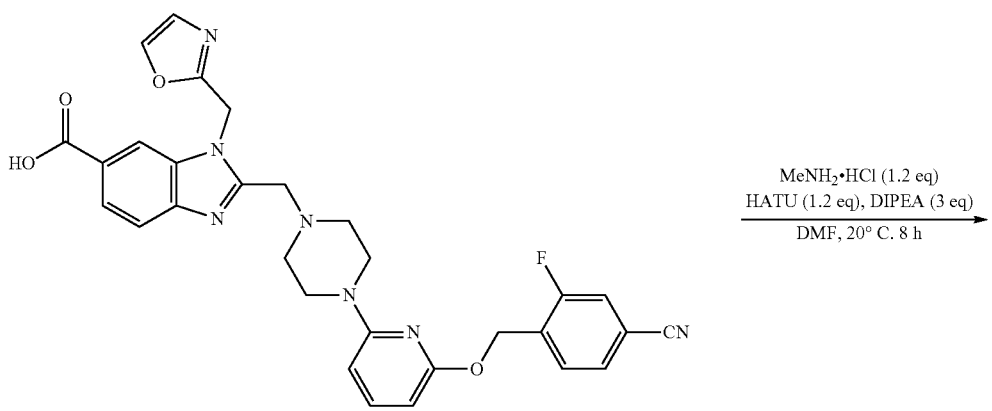

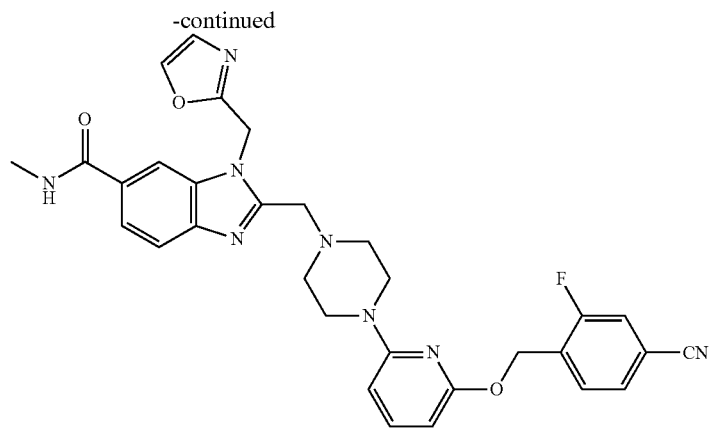

To a solution of the indicated precursor (50 mg, 88.09 umol, 1 eq) in DMF (5 mL) was added HATU (40.20 mg, 105.71 umol, 1.2 eq) and DIPEA (34.16 mg, 264.28 umol, 46.03 uL, 3 eq) at 20° C. After the mixture was stirred at 20° C. for 0.5 h, methylamine (7.14 mg, 105.71 umol, 1.2 eq, HCl) was added to the mixture at 20° C. and the reaction was stirred at 20° C. for 7.5 h. TLC (Petroleum ether:Ethyl acetate=1:2, product Rf=0.25) showed the starting material was disappeared and a new main spot was detected. LCMS (MS m/z 581.3 (M+H)) showed the desired product MS. The mixture was poured into water (15 mL) and extracted with ethyl acetate (10 mL*3). The combined ethyl acetate was washed with brine (15 mL), dried over $Na_2SO_4$, filtered and concentrated. The residue was purified by prep-TLC (Ethyl acetate:Petroleum ether=2:1). Compound 1 (24.40 mg, 39.17 umol, 44.46% yield, 93.2% purity) was obtained as white solid. LCMS (Rt=3.004 min, MS m/z 581.2 (M+H)). $^1$H NMR (400 MHz, METHANOL-$d_4$) δ ppm 8.07 (s, 1H), 7.87 (s, 1H), 7.81-7.76 (m, 1H), 7.75-7.68 (m, 1H), 7.65-7.51 (m, 3H), 7.43 (t, J=8.0 Hz, 1H), 7.11 (s, 1H), 6.23 (d, J=8.0 Hz, 1H), 6.13 (d, J=7.6 Hz, 1H), 5.89 (s, 2H), 5.41 (s, 2H), 3.94 (s, 2H), 3.29 (m, 4H), 2.95 (s, 3H), 2.50 (t, J=4.8 Hz, 4H).

Example 2

Preparation of Compound 2

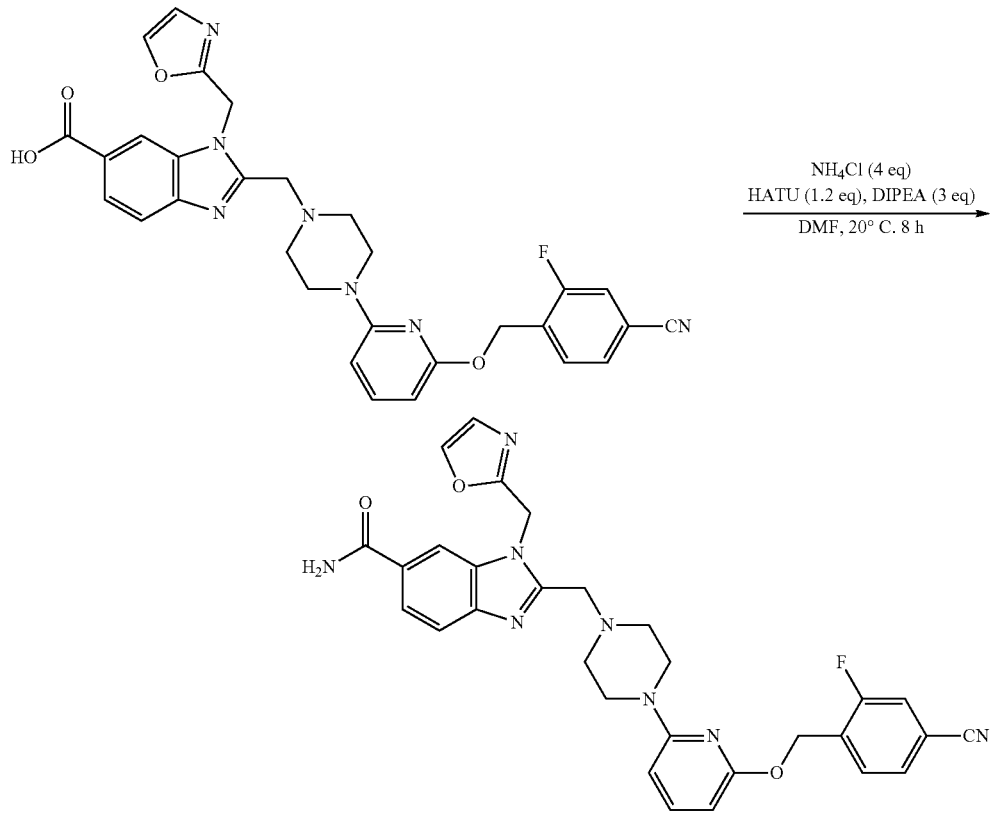

To a solution of the indicated precursor (40 mg, 70.48 umol, 1 eq) in DMF (1 mL) was added HATU (32.16 mg, 84.57 umol, 1.2 eq) and DIPEA (27.32 mg, 211.43 umol, 36.83 uL, 3 eq) at 20° C. After the mixture was stirred at 20° C. for 0.5 h, NH$_4$Cl (15.08 mg, 281.90 umol, 4 eq) was added to the mixture at 20° C. and the reaction was stirred at 20° C. for 7.5 h. TLC (Ethyl acetate:Methanol=10:1, product Rf=0.33) showed starting material disappeared and a new main spot was detected. The mixture was poured into water (15 mL) and extracted with ethyl acetate (10 mL*3). The combined ethyl acetate was washed with brine (15 mL), dried over Na$_2$SO$_4$, filtered and concentrated. The residue was purified by prep-TLC (Ethyl acetate:Methanol=10:1). Compound 2 (28.05 mg, 46.69 umol, 66.25% yield, 96.65% purity) was obtained as white solid and checked by HPLC. $^1$H NMR (400 MHz, DMSO-d$_6$) δ ppm 8.17 (s, 1H), 8.04 (s, 1H), 7.92 (br s, 1H), 7.88-7.86 (d, J=10.0 Hz, 1H), 7.79 (d, J=8.4 Hz, 1H), 7.72-7.60 (m, 3H), 7.44 (t, J=8.0 Hz, 1H), 7.32 (br s, 1H), 7.13 (s, 1H), 6.28 (d, J=8.0 Hz, 1H), 6.10 (d, J=8.0 Hz, 1H), 5.84 (s, 2H), 5.37 (s, 2H), 3.86 (s, 2H), 3.19 (m, 4H), 2.40 (m, 4H). LCMS: RT=2.270 min, MS cal.: 566.5, [M+H]$^+$=567.2

Example 3

Preparation of Compound 3

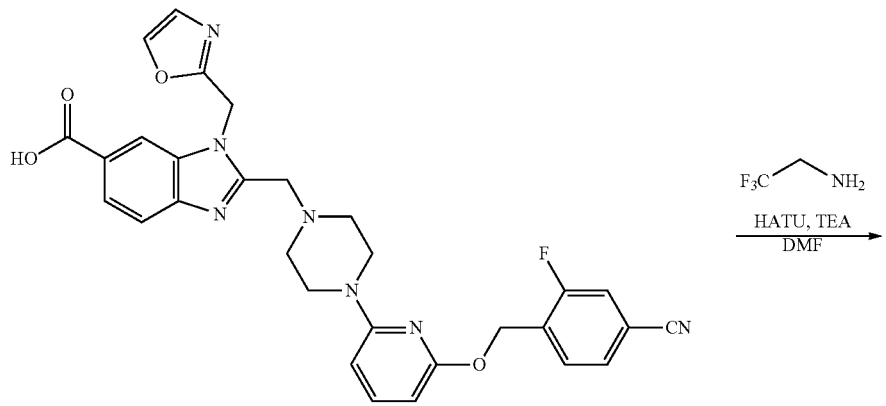

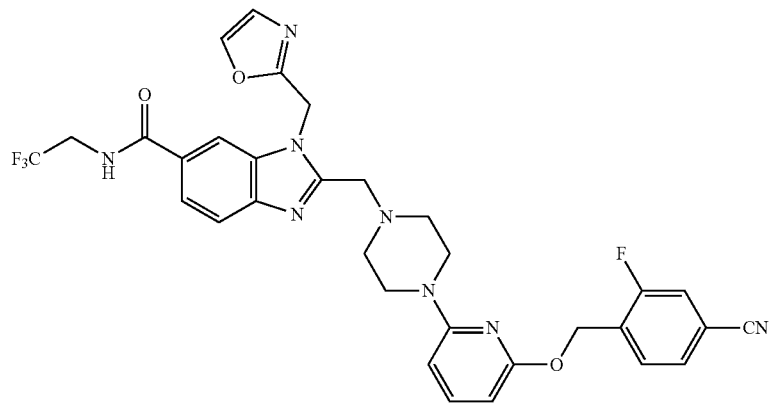

To a solution of the indicated precursor (50 mg, 88.09 umol, 1 eq) in DMF (3 mL) was added HATU (40.20 mg, 105.71 umol, 1.2 eq) and DIPEA (34.16 mg, 264.28 umol, 46.03 uL, 3 eq) at 20° C. After the mixture was stirred at 20° C. for 0.5 h, 2,2,2-trifluoroethanamine (43.63 mg, 440.47 umol, 34.63 uL, 5 eq) was added to the mixture at 20° C. and the reaction was stirred at 20° C. for 7.5 h. The mixture was poured into water (15 mL) and extracted with ethyl acetate (20 mL*3). The combined ethyl acetate was washed with brine (15 mL), dried over $Na_2SO_4$, filtered and concentrated. The residue was purified by prep-TLC (Ethyl acetate:Methanol=10:1). Compound 3 was obtained as white solid. LCMS (MS m/z 649.3 (M+H)). $^1$H NMR (400 MHz, METHANOL-$d_4$) δ ppm 8.14 (s, 1H), 7.87 (s, 2H), 7.85-7.83 (d, J=7.6 Hz, 1H), 7.75-7.73 (d, J=7.6 Hz, 1H), 7.52-7.62 (m, 3H), 7.43 (t, J=8.0 Hz, 1H), 7.12 (s, 1H), 6.23 (d, J=8.07 Hz, 1H), 6.13 (d, J=7.82 Hz, 1H), 5.91 (s, 2H), 5.41 (s, 2H), 4.12 (q, J=9.2 Hz, 2H), 3.95 (s, 2H), 3.30-3.26 (m, 4H), 2.51 (m, 4H).

Example 4

Preparation of Compound 4

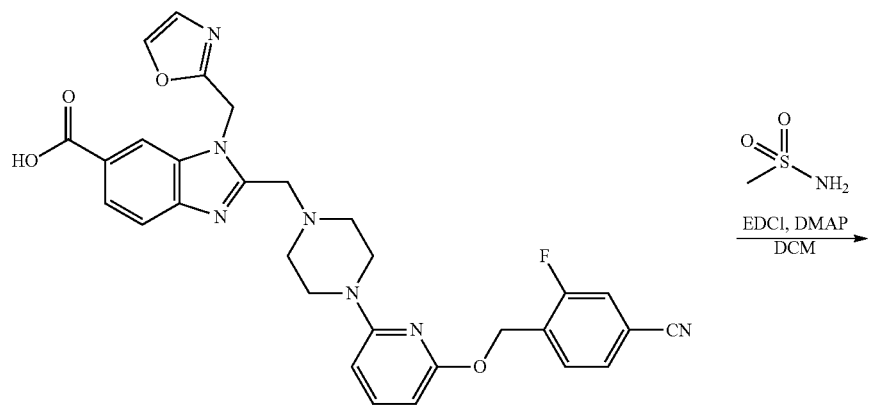

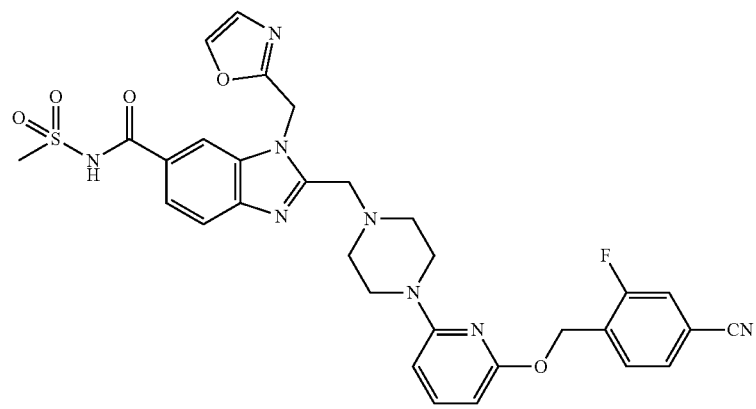

To a solution of the indicated precursor (70 mg, 123.33 umol, 1 eq) in DCM (3 mL) was added 2-chloro-1-methyl-pyridin-1-ium iodide (37.81 mg, 148.00 umol, 1.2 eq), methanesulfonamide (23.46 mg, 246.67 umol, 2 eq) and DMAP (1.51 mg, 12.33 umol, 0.1 eq) at 20° C. After the reaction was stirred at 20° C. for 10 min, TEA (37.44 mg, 370.00 umol, 51.50 uL, 3 eq) was added to the mixture at 20° C. The reaction was stirred at 20° C. for 16 h. TLC (Dichloromethane:Methanol=10:1, product Rf=0.60) showed SM disappeared and a new main spot was detected. The mixture was poured into water (10 mL) and extracted with ethyl acetate (10 mL*3). The combined ethyl acetate was washed with brine (15 mL), dried over $Na_2SO_4$, filtered and concentrated. The residue was purified by prep-TLC (Dichloromethane:Methanol=10:1). Compound 4 (26.45 mg, 38.65 umol, 31.34% yield, 94.20% purity) was obtained as white solid. $^1$H NMR (400 MHz, $CDCl_3$-d) δ ppm 1H NMR (400 MHz, CDCl3) δ ppm 8.14 (s, 1H), 7.81 (d, J=8.4 Hz, 1H), 7.74-7.68 (m, 1H), 7.62-7.55 (m, 2H), 7.43 (m, 2H), 7.34 (d, J=9.6 Hz, 1H), 7.04 (s, 1H), 6.12-6.21 (m, 2H), 5.79 (s, 2H), 5.42 (s, 2H), 3.98 (s, 2H), 3.39 (m, 7H), 2.61 (m, 4H). LCMS: RT=2.229 min, MS cal.:644.7, $[M+H]^+$=645.2.

Example 5

Preparation of Compound 5

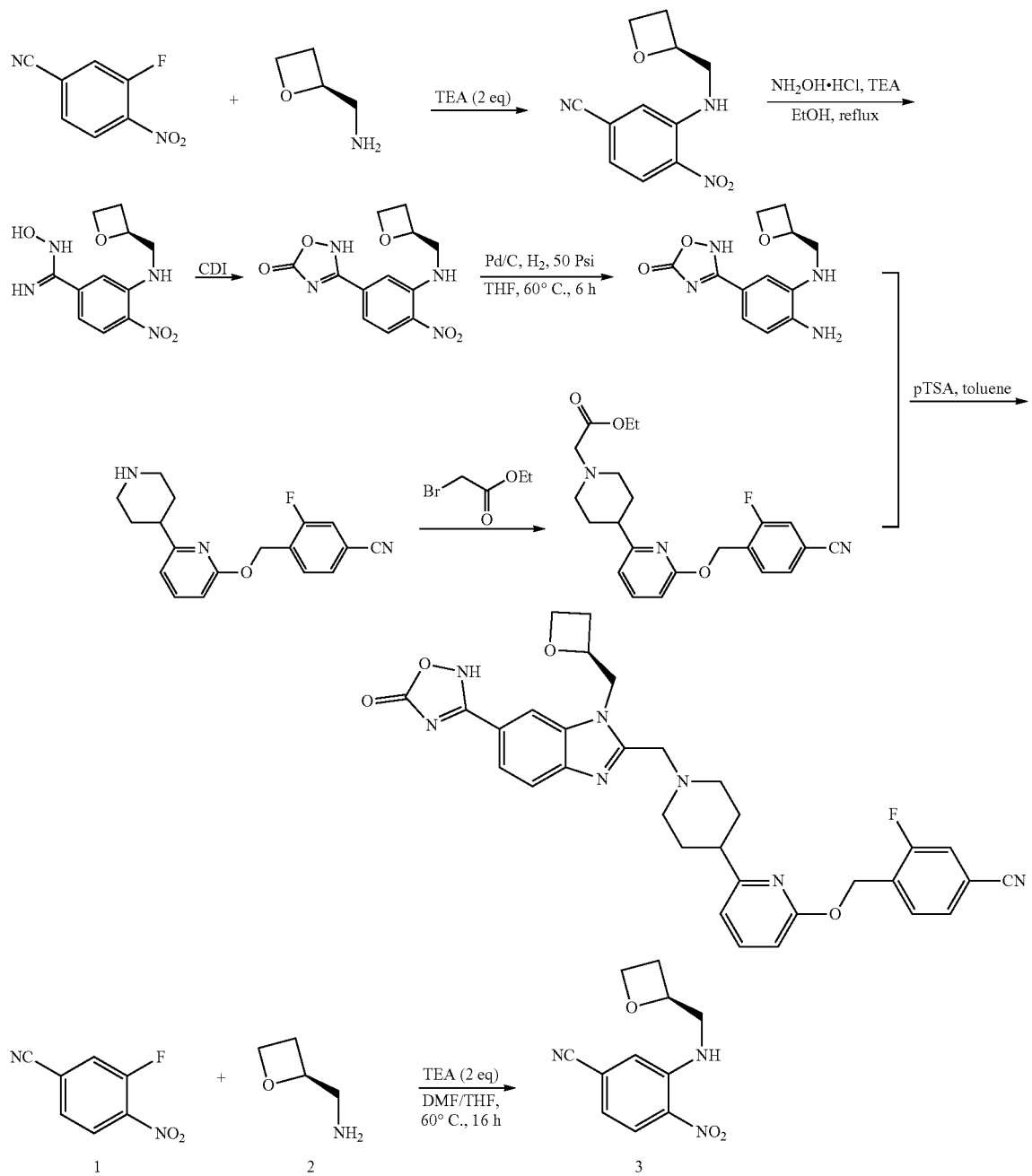

To a solution of Intermediate 1 (500 mg, 3.01 mmol, 1 eq) and Intermediate 2 (314.68 mg, 3.61 mmol, 1.2 eq) in THF (30 mL) and DMF (4 mL) was added TEA (609.18 mg, 6.02 mmol, 837.93 uL, 2 eq). The mixture was stirred at 60° C. for 16 hr. TLC (Petroleum ether:Ethyl acetate=3:1, $R_f$=0.3) showed a new spot was generated. The mixture was quenched with water (40 mL) and extracted with ethyl acetate (40 mL×3). The combined organic phase was washed with brine (20 mL×3), dried with anhydrous $Na_2SO_4$, filtered and concentrated in vacuum. The crude product was purified by silica gel column chromatography (Petroleum ether:Ethyl acetate=10:1~1:1). Intermediate 3 (740 mg, crude) was obtained as a yellow solid. $^1$H NMR (400 MHz, CHLOROFORM-d) δ 8.42 (br s, 1H), 8.28 (d, J=8.8 Hz, 1H), 7.29 (d, J=1.1 Hz, 1H), 6.91 (dd, J=1.4, 8.7 Hz, 1H), 5.17 (dt, J=3.7, 7.6 Hz, 1H), 4.83-4.73 (m, 1H), 4.62 (td, J=6.1, 9.2 Hz, 1H), 3.57 (t, J=5.0 Hz, 2H), 2.88-2.75 (m, 1H), 2.69-2.57 (m, 1H).

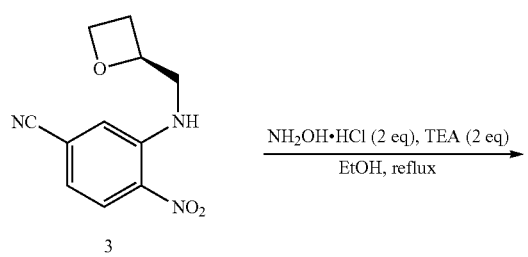

3

To a solution of Intermediate 3 (0.49 g, 2.10 mmol, 1 eq) in EtOH (20 mL) was added TEA (425.20 mg, 4.20 mmol, 584.87 uL, 2 eq) and NH$_2$OH·HCl (292.00 mg, 4.20 mmol, 2 eq). The mixture was stirred at 85° C. for 2 hr. TLC (Petroleum ether:Ethyl acetate=0:1, $R_f$=0.42) showed a new spot was generated. The reaction mixture was concentrated. H$_2$O (30 mL) was added and the aqueous phase was extracted with ethyl acetate (30 mL×3). The combined organic phase was washed with brine (20 mL), dried with anhydrous Na$_2$SO$_4$, filtered and concentrated under vacuum. The crude product was purified by silica gel column chromatography (Petroleum ether:Ethyl acetate=0:1). Intermediate 4 (0.48 g, 1.80 mmol, 85.81% yield) was obtained as a yellow solid. $^1$H NMR (400 MHz, METHANOL-d$_4$) δ 8.42 (br s, 1H), 8.15 (d, J=9.0 Hz, 1H), 7.34 (d, J=1.5 Hz, 1H), 6.98 (dd, J=1.8, 9.0 Hz, 1H), 5.22-5.10 (m, 1H), 4.77-4.69 (m, 1H), 4.65-4.57 (m, 1H), 3.78-3.61 (m, 2H), 2.84-2.72 (m, 1H), 2.68-2.55 (m, 1H).

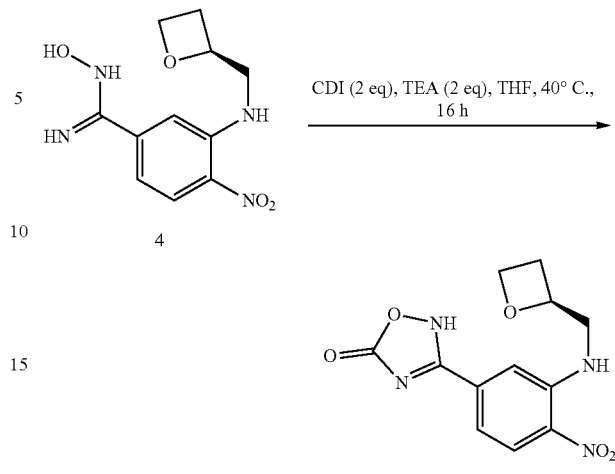

To a solution of Intermediate 4 (0.6 g, 2.25 mmol, 1 eq) in THF (30 mL) was added CDI (730.80 mg, 4.51 mmol, 2 eq) and TEA (456.06 mg, 4.51 mmol, 627.32 uL, 2 eq). The mixture was stirred at 40° C. for 16 hr. Another batch of CDI (365.40 mg, 2.25 mmol, 1 eq) and TEA (228.03 mg, 2.25 mmol, 313.66 uL, 1 eq) was added. The mixture was stirred at 40° C. for 4 hr. The reaction mixture was concentrated. NH$_4$Cl (50 mL) was added and the aqueous phase was extracted with ethyl acetate (50 mL×3) and DCM:i-PrOH=10:1 (50 mL×3). The combined organic phase was, dried over anhydrous Na$_2$SO$_4$, filtered and concentrated under vacuum. The residue was stirred in ethyl acetate (5 mL) for 10 min and then was filtered. The filter cake was washed with MeCN (3 mL×2). Intermediate 5 (0.6 g, 2.05 mmol, 91.11% yield) was obtained as a yellow solid. $^1$H NMR (400 MHz, METHANOL-d$_4$) δ 8.25 (d, J=8.8 Hz, 1H), 7.53 (d, J=1.7 Hz, 1H), 7.38 (s, 1H), 7.12 (dd, J=1.7, 8.9 Hz, 1H), 5.23-5.11 (m, 1H), 4.77-4.69 (m, 1H), 4.60 (td, J=6.0, 9.2 Hz, 1H), 3.78-3.63 (m, 2H), 2.85-2.73 (m, 1H), 2.63 (tdd, J=7.2, 9.1, 11.3 Hz, 1H).

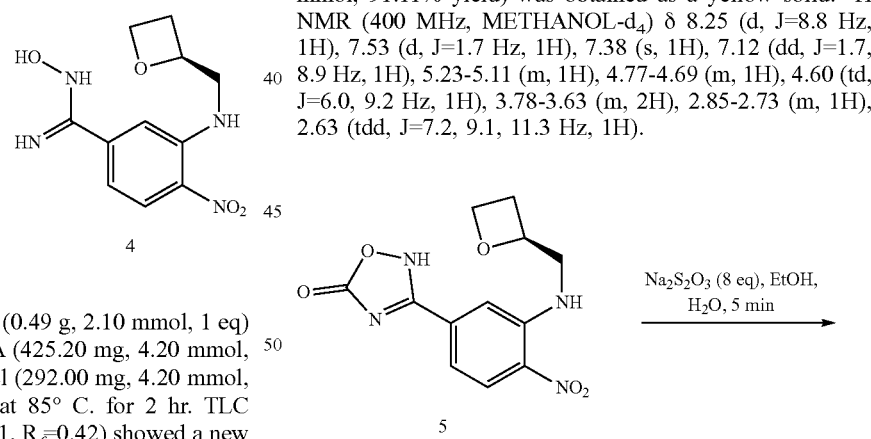

To a solution of Intermediate 5 (0.55 g, 1.88 mmol, 1 eq) in EtOH (20 mL) was added Na$_2$S$_2$O$_3$ (2.62 g, 15.06 mmol, 3.28 mL, 8 eq) in H$_2$O (16 mL). The mixture was stirred at 25° C. for 5 min. The mixture was concentrated to remove EtOH. H₂O (50 mL) was added and the mixture was extracted with ethyl acetate (50 mL×3). The combined organic phase was washed with brine (20 mL), dried with anhydrous Na₂SO₄, filtered and concentrated in vacuum. The product was used for the next step without purification. Intermediate 6 (410 mg, 1.56 mmol, 83.07% yield) was obtained as a yellow solid. ¹H NMR (400 MHz, METHANOL-d₄) δ 7.03-6.99 (m, 2H), 6.74 (d, J=8.4 Hz, 1H), 5.11 (dq, J=4.2, 6.9 Hz, 1H), 4.73 (dt, J=5.9, 8.0 Hz, 1H), 4.62 (td, J=6.0, 9.1 Hz, 1H), 3.52-3.36 (m, 2H), 2.80-2.71 (m, 1H), 2.60 (tdd, J=7.2, 9.1, 11.1 Hz, 1H).

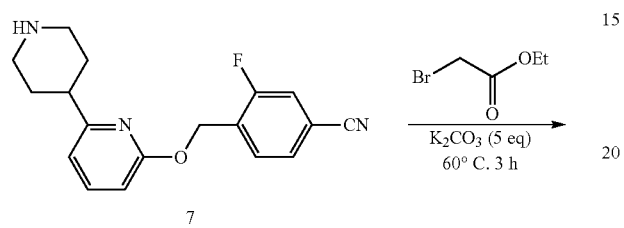

7

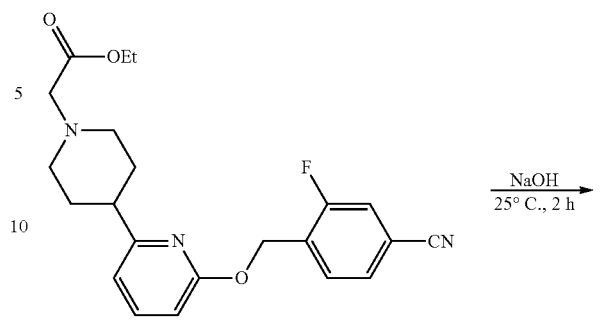

8

To a solution of Intermediate 7 (0.5 g, 1.61 mmol, 1 eq) and ethyl 2-bromoacetate (295.00 mg, 1.77 mmol, 195.37 uL, 1.1 eq) in MeCN (20 mL) was added K₂CO₃ (1.11 g, 8.03 mmol, 5 eq) at 20° C. The mixture was stirred at 60° C. for 3 hr. The reaction mixture was filtered, the cake was washed by ethyl acetate (20 mL). The filtrate was concentrated and the crude product was purified by silica gel column chromatography (Petroleum ether:Ethyl acetate=10:1~5:1). Intermediate 8 (430 mg, 1.08 mmol, 67.37% yield) was obtained as a yellow oil. ¹H NMR (400 MHz, CHLOROFORM-d) δ 7.64 (t, J=7.5 Hz, 1H), 7.54 (t, J=7.8 Hz, 1H), 7.45 (d, J=7.9 Hz, 1H), 7.38 (d, J=9.3 Hz, 1H), 6.78 (d, J=7.3 Hz, 1H), 6.65 (d, J=8.2 Hz, 1H), 5.57-5.49 (m, 2H), 4.22 (q, J=7.1 Hz, 2H), 3.27 (s, 2H), 3.07 (br d, J=11.5 Hz, 2H), 2.66-2.52 (m, 1H), 2.39-2.27 (m, 2H), 1.96 (dq, J=3.6, 12.3 Hz, 2H), 1.89-1.80 (m, 2H), 1.30 (t, J=7.2 Hz, 3H).

9

To a solution of Intermediate 8 (450 mg, 1.13 mmol, 1 eq) in MeOH (2 mL) and THF (5 mL) was added a solution of NaOH (67.93 mg, 1.70 mmol, 1.5 eq) in H₂O (5 mL) dropwise. The mixture was stirred at 25° C. for 2 hr. The mixture was concentrated to remove THF and MeOH. And then, 1 M HCl was added to the reaction mixture drop-wise until to pH 5. H₂O (30 mL) was added and the aqueous phase was extracted with ethyl acetate (30 mL×3), dried with anhydrous Na₂SO₄, filtered and concentrated under vacuum. The product was used for the next step without purification. Intermediate 9 (0.7 g, crude) was obtained as yellow solid. ¹H NMR (400 MHz, DMSO-d₆) δ 7.91 (dd, J=1.3, 10.0 Hz, 1H), 7.80-7.66 (m, 4H), 6.93 (d, J=7.2 Hz, 1H), 6.78 (d, J=8.2 Hz, 1H), 5.53-5.48 (m, 2H), 4.06 (s, 2H), 3.94-3.85 (m, 1H), 3.55 (br d, J=12.2 Hz, 1H), 3.16 (br s, 1H), 2.92-2.83 (m, 1H), 2.76 (br s, 1H), 2.07-1.96 (m, 3H).

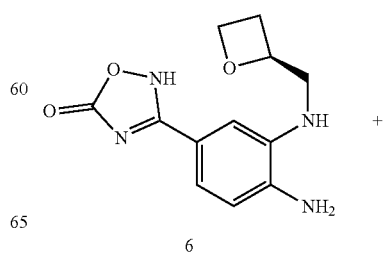

6

-continued

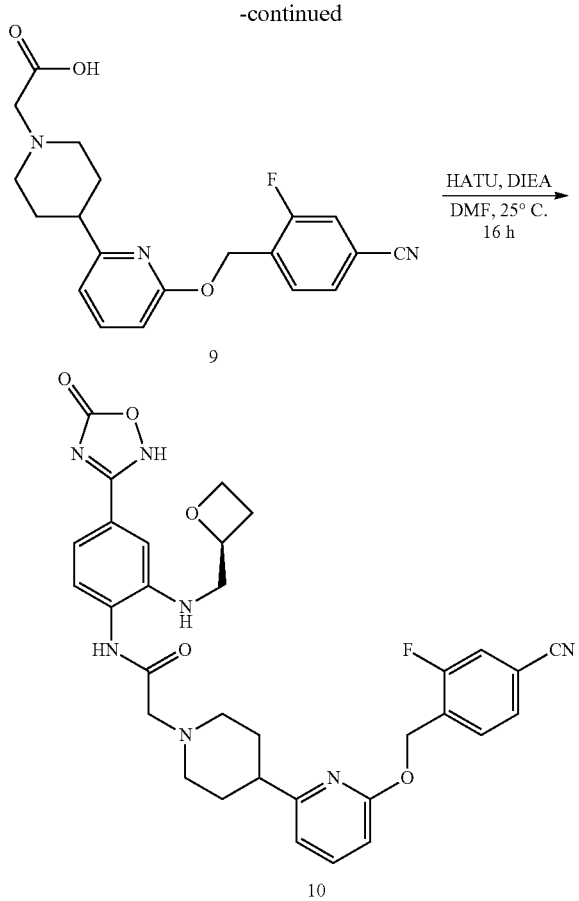

9

10

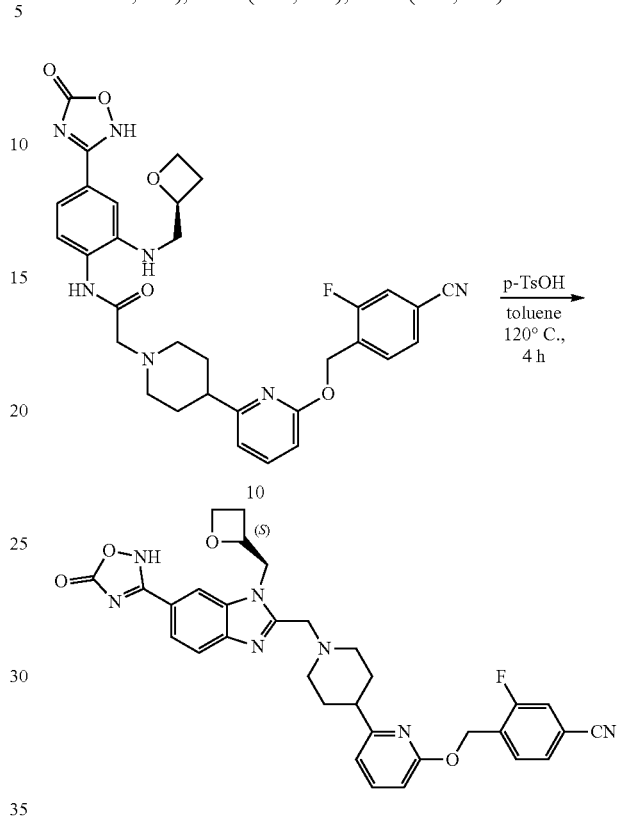

10

To a solution of Intermediate 9 (507.05 mg, 1.37 mmol, 1.8 eq) and Intermediate 6 (200 mg, 762.59 umol, 1 eq) in DMF (5 mL) was added HATU (434.94 mg, 1.14 mmol, 1.5 eq) and DIEA (197.12 mg, 1.53 mmol, 265.66 uL, 2 eq). The mixture was stirred at 25° C. for 16 hr.

The mixture was quenched with water (30 mL) and extracted with ethyl acetate (30 mL×3). The combined organic phase was washed with brine (20 mL×3), dried with anhydrous Na$_2$SO$_4$, filtered and concentrated under vacuum. The crude product was purified by prep-TLC (Ethyl acetate: Methanol=5:1, R$_f$=0.32). Intermediate 10 (180 mg, 293.33 umol, 38.47% yield) was obtained as a yellow solid. $^1$H NMR (400 MHz, CHLOROFORM-d) δ 9.38 (br s, 1H), 8.03 (s, 1H), 7.65-7.52 (m, 3H), 7.43 (br d, J=7.7 Hz, 1H), 7.33 (br d, J=9.5 Hz, 1H), 7.15 (br s, 2H), 6.80 (d, J=7.1 Hz, 1H), 6.67 (d, J=8.2 Hz, 1H), 5.50 (s, 2H), 5.02 (br s, 1H), 4.64 (br d, J=6.8 Hz, 1H), 4.58-4.49 (m, 2H), 4.31 (br s, 1H), 3.92 (s, 1H), 3.29 (br s, 2H), 3.08 (br d, J=9.0 Hz, 2H), 2.65 (br d, J=7.3 Hz, 2H), 2.49 (br s, 3H), 1.94 (br s, 3H).

To a solution of Intermediate 10 (170 mg, 277.04 umol, 1 eq) in toluene (6 mL) was added PTSA (23.85 mg, 138.52 umol, 0.5 eq). The mixture was stirred at 120° C. for 4 hr. The mixture was concentrated. The crude product was purified by prep-HPLC (NH$_4$HCO$_3$). Column: Waters Xbridge Prep OBD C18 150*40 mm*10 um; mobile phase: [water (10 mM NH4HCO3)-ACN]; B %: 25%-40%, 8 min. Compound 5 (12.01 mg, 19.55 umol, 7.06% yield, 96.96% purity) was obtained as a white solid. $^1$H NMR (400 MHz, METHANOL-d$_4$) δ 8.10 (s, 1H), 7.79-7.65 (m, 3H), 7.65-7.49 (m, 3H), 6.85 (d, J=7.2 Hz, 1H), 6.70 (d, J=8.0 Hz, 1H), 5.52 (s, 2H), 5.29 (m, 1H), 4.74 (m, 1H), 4.66 (m, 2H), 4.50 (m, 1H), 4.17-4.09 (d, J=13.6 Hz, 1H), 4.05-3.98 (d, J=13.6 Hz, 1H), 3.16 (m, 1H), 3.05 (m, 1H), 2.87-2.78 (m, 1H), 2.73-2.63 (m, 1H), 2.60-2.52 (m, 1H), 2.50-2.37 (m, 2H), 1.94-1.82 (m, 4H). LCMS: [M+H]$^+$=596.3.

Example 6

Preparation of Compound 6

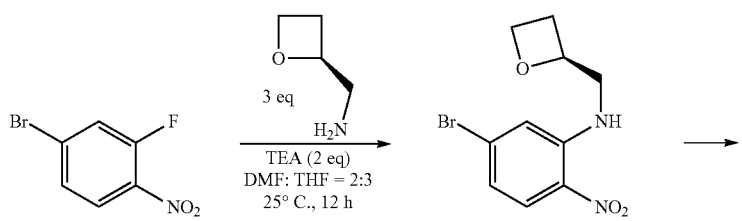

-continued
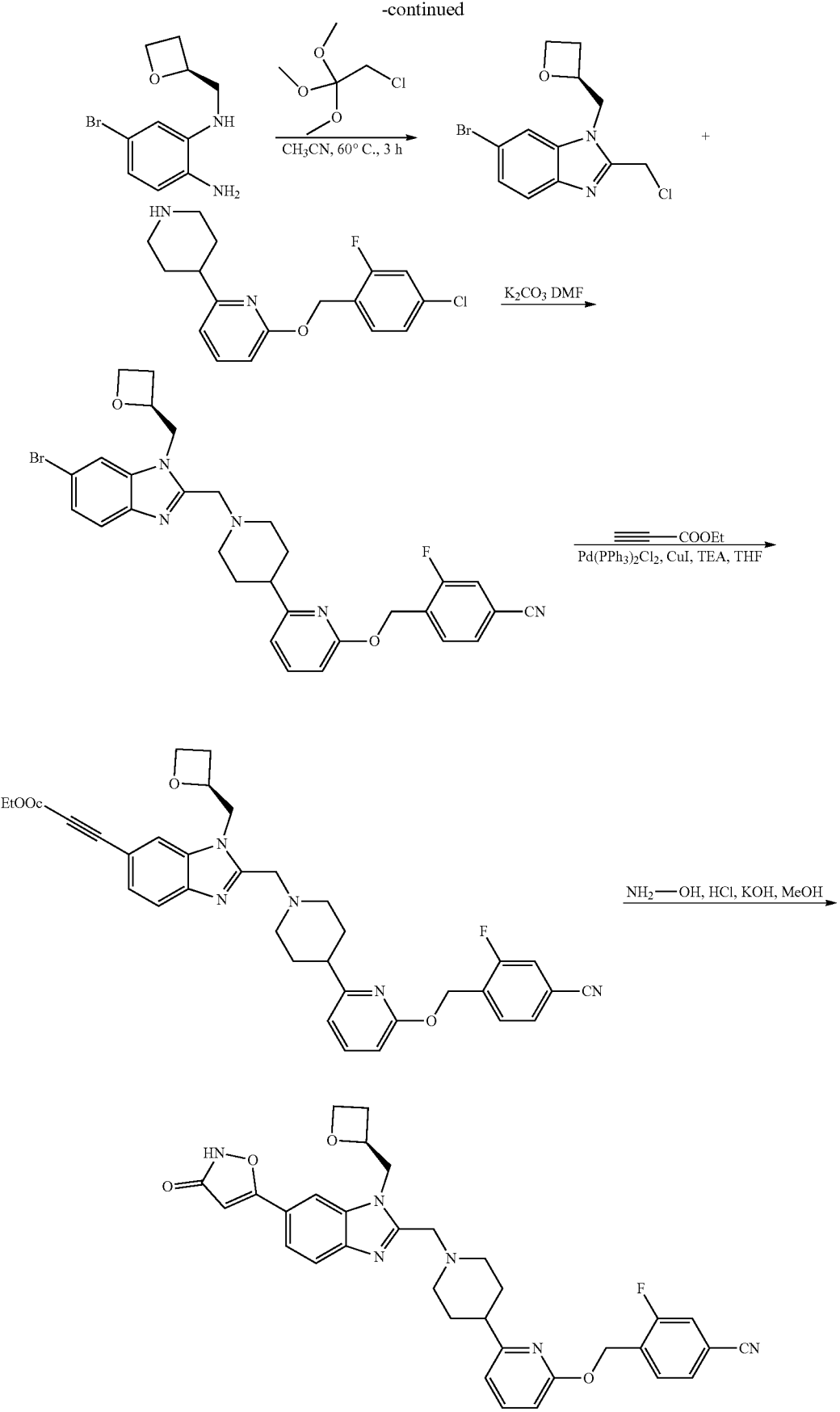

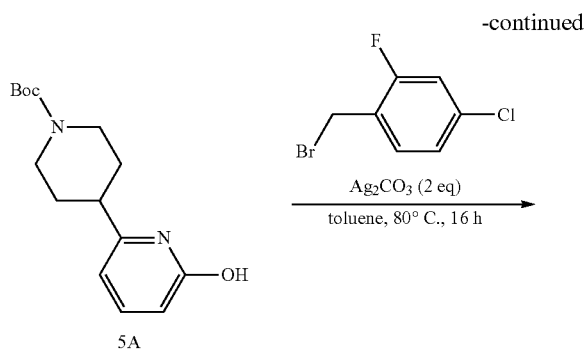

Ag₂CO₃ (594.39 mg, 2.16 mmol, 97.76 uL, 2 eq) as added to the solution of Intermediate 5A (300 mg, 1.08 mmol, 1 eq) and 1-(bromomethyl)-4-chloro-2-fluoro-benzene (289.03 mg, 1.29 mmol, 1.2 eq) in toluene (1 mL) at 20° C. The mixture was stirred at 80° C. for 16 h. The mixture was filtered and the filtrate concentrated. The residue was purified by column chromatography (SiO2, Petroleum ether/Ethyl acetate=80:1 to 20:1). Intermediate 5B (390 mg, 926.58 umol, 85.97% yield) was obtained as colorless oil. ¹H NMR (400 MHz, METHANOL-d4) δ ppm 7.58 (t, J=7.8 Hz, 1H), 7.48 (t, J=8.3 Hz, 1H), 7.23-7.15 (m, 2H), 6.82 (d, J=7.3 Hz, 1H), 6.64 (d, J=8.3 Hz, 1H), 5.40 (s, 2H), 4.16 (br d, J=13.2 Hz, 2H), 2.94-2.72 (m, 3H), 1.85-1.76 (m, 2H), 1.73-1.61 (m, 2H), 1.49 (s, 9H).

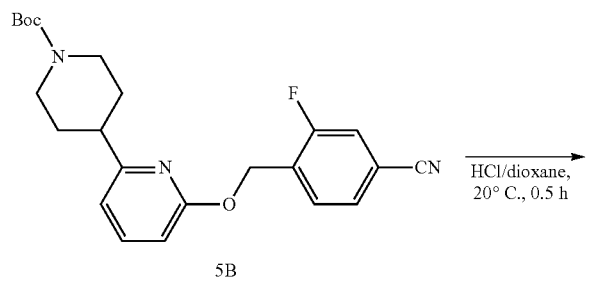

The solution of Intermediate 5B (370 mg, 879.06 umol, 1 eq) in HCl/dioxane (15 mL) was stirred at 20° C. for 0.5 h. The solution was concentrated to remove the solvent. Intermediate 5 was obtained as white solid. ¹H NMR (400 MHz, METHANOL-d4) δ ppm 8.07 (t, J=8.0 Hz, 1H), 7.58 (t, J=8.1 Hz, 1H), 7.34-7.25 (m, 2H), 7.19 (dd, J=5.0, 7.9 Hz, 2H), 5.53 (s, 2H), 3.53 (br d, J=12.8 Hz, 2H), 3.23-3.07 (m, 3H), 2.22-2.00 (m, 4H).

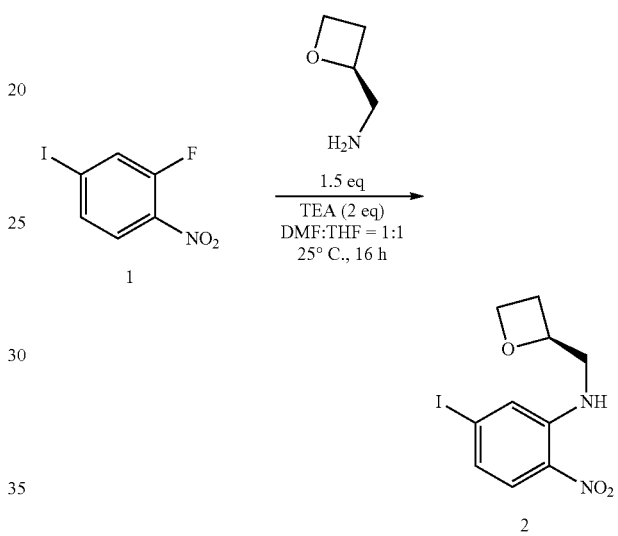

To a solution of Intermediate 1 (0.8 g, 3.00 mmol, 1 eq) and [(2S)-oxetan-2-yl]methanamine (391.56 mg, 4.49 mmol, 1.5 eq) in DMF (14 mL) and THF (7 mL) was added TEA (606.39 mg, 5.99 mmol, 834.10 uL, 2 eq) at 20° C. The solution was stirred at 25° C. for 16 h. The mixture was poured into water (30 mL) and extracted with ethyl acetate (20 mL*3). The combined ethyl acetate was washed with H₂O (20 mL*3), brine (10 mL), dried over Na₂SO₄, filtered and concentrated in vacuo. The residue was purified by column chromatography (SiO₂, Petroleum ether/Ethyl acetate=80:1 to 20:1). Intermediate 2 (681 mg, 2.04 mmol, 68.03% yield) was obtained as yellow solid. ¹H NMR (400 MHz, METHANOL-d4) δ ppm 8.34 (br s, 1H), 7.84 (d, J=8.9 Hz, 1H), 7.53 (d, J=1.6 Hz, 1H), 7.04 (dd, J=1.7, 8.9 Hz, 1H), 5.15-5.07 (m, 1H), 4.72 (dt, J=6.1, 8.0 Hz, 1H), 4.58 (td, J=6.0, 9.2 Hz, 1H), 3.68-3.53 (m, 2H), 2.81-2.71 (m, 1H), 2.61 (tdd, J=7.2, 9.1, 11.3 Hz, 1H).

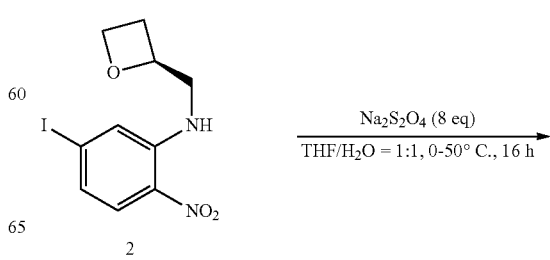

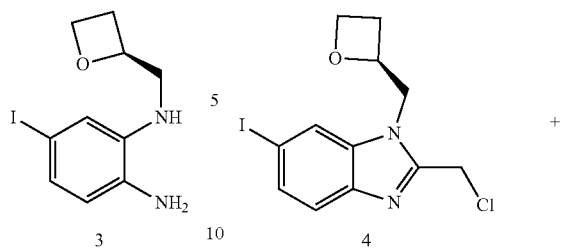

A solution of Na₂S₂O₃ (1.16 g, 6.66 mmol, 1.45 mL, 8 eq) in H₂O (10 mL) was added to the solution of Intermediate 2 (278 mg, 832.06 umol, 1 eq) in THF (10 mL) at 0° C. and the solution was stirred at 50° C. for 16 h. The solution was concentrated to remove most of THF. The mixture was extracted with ethyl acetate (10 mL*3). The combined ethyl acetate was washed with brine (15 mL), dried over Na₂SO₄, filtered and concentrated. Intermediate 3 (197 mg, crude) was obtained as yellow oil. ¹H NMR (400 MHz, METHANOL-d4) δ ppm 6.90-6.82 (m, 2H), 6.48 (d, J=8.1 Hz, 1H), 5.05 (dq, J=4.2, 6.9 Hz, 1H), 4.75-4.67 (m, 1H), 4.60 (td, J=6.0, 9.1 Hz, 1H), 3.41-3.32 (m, 1H), 2.78-2.68 (m, 1H), 2.64-2.52 (m, 1H).

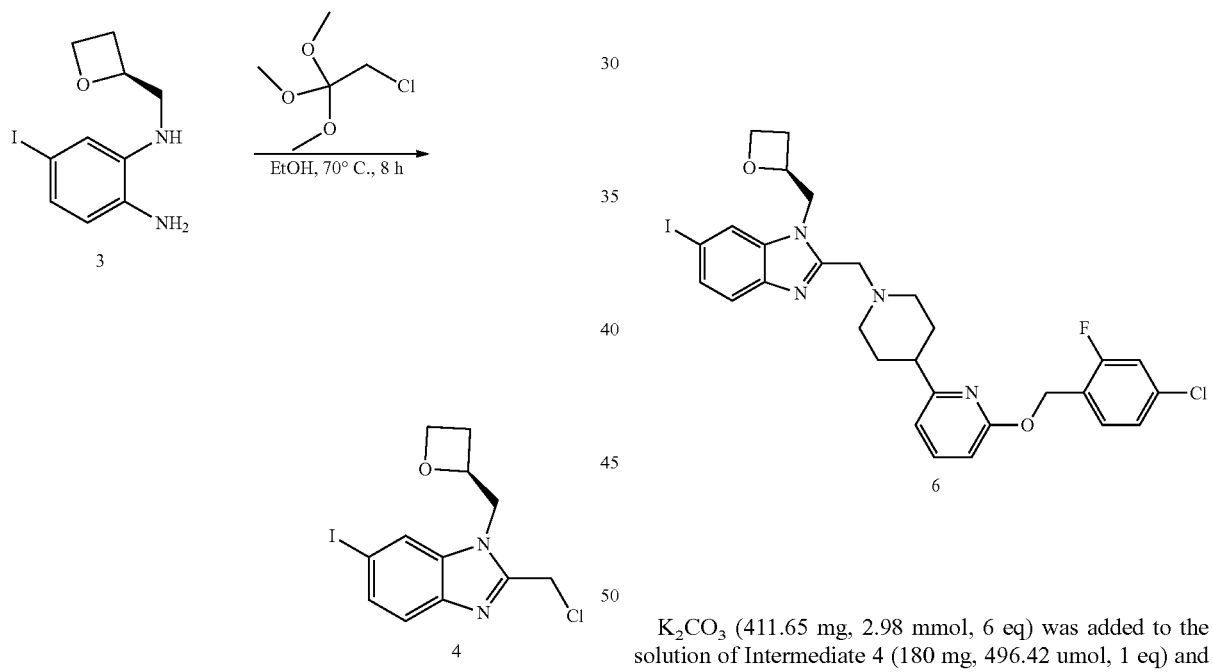

To a solution of Intermediate 3 (197 mg, 647.76 umol, 1 eq) in EtOH (10 mL) was added 2-chloro-1,1,1-trimethoxyethane (600.83 mg, 3.89 mmol, 522.46 uL, 6 eq) at 20° C. and the mixture was stirred at 70° C. for 16 h. The mixture was concentrated to remove most of solvent. The residue was purified by column chromatography (SiO₂, Petroleum ether/Ethyl acetate=80:1 to 20:1). Intermediate 4 (180 mg, 496.42 umol, 76.64% yield) was obtained as yellow solid. ¹H NMR (400 MHz, METHANOL-d₄) δ ppm 8.05 (d, J=1.3 Hz, 1H), 7.60 (dd, J=1.5, 8.5 Hz, 1H), 7.45 (d, J=8.6 Hz, 1H), 5.17 (dq, J=2.4, 7.1 Hz, 1H), 5.08-4.96 (m, 2H), 4.70-4.49 (m, 3H), 4.38 (td, J=6.0, 9.2 Hz, 1H), 2.76 (dtd, J=6.1, 8.1, 11.5 Hz, 1H), 2.44 (tdd, J=7.3, 9.1, 11.4 Hz, 1H).

K₂CO₃ (411.65 mg, 2.98 mmol, 6 eq) was added to the solution of Intermediate 4 (180 mg, 496.42 umol, 1 eq) and Intermediate 5 (283.76 mg, 794.28 umol, 1.6 eq, HCl) in CH₃CN (1 mL) at 20° C. and the mixture was stirred at 50° C. for 16 h. The mixture was filtered and the filtrate concentrated. The residue was purified by prep-TLC (Petroleum ether/Ethyl acetate=3:1). Intermediate 6 (280 mg, 389.54 umol, 78.47% yield, 90% purity) was obtained as yellow solid. ¹H NMR (400 MHz, METHANOL-d4) δ ppm 8.03 (d, J=1.2 Hz, 1H), 7.60-7.53 (m, 2H), 7.49 (s, 1H), 7.41 (d, J=8.6 Hz, 1H), 7.24-7.14 (m, 2H), 6.82 (d, J=7.2 Hz, 1H), 6.63 (d, J=8.1 Hz, 1H), 5.42 (s, 2H), 5.24 (dq, J=2.5, 7.2 Hz, 1H), 4.78 (s, 2H), 4.67-4.59 (m, 2H), 4.45 (s, 1H), 4.00-3.93 (m, 1H), 3.87-3.80 (m, 1H), 3.08-3.00 (m, 1H), 2.91 (br d, J=12.2 Hz, 1H), 2.85-2.74 (m, 1H), 2.69-2.58 (m, 1H), 2.56-2.45 (m, 1H), 2.36-2.19 (m, 2H), 1.91-1.78 (m, 4H).

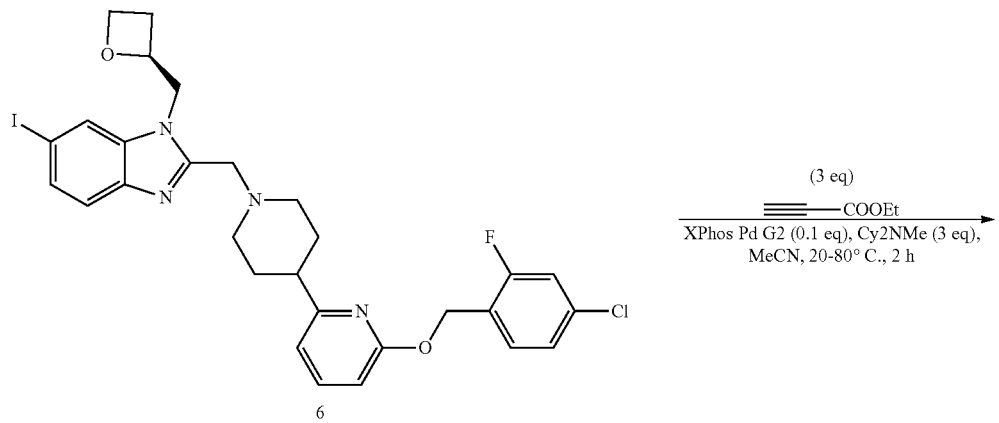

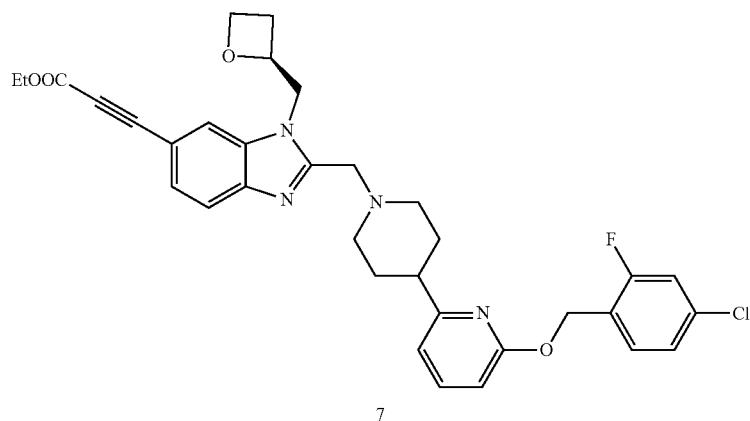

Xphos Pd G2 (29.43 mg, 37.41 umol, 0.1 eq) and N-cyclohexyl-N-methyl-cyclohexanamine (219.22 mg, 1.12 mmol, 238.03 uL, 3 eq) was added to a solution of Intermediate 6 (242 mg, 374.08 umol, 1 eq) and ethyl prop-2-ynoate (110.09 mg, 1.12 mmol, 110.09 uL, 3 eq) in CH₃CN (9 mL) at 20° C. and the mixture was stirred at 80° C. for 4 h. The mixture was poured into water (15 mL) and extracted with ethyl acetate (10 mL*3). The combined ethyl acetate was washed with brine (15 mL), dried over $Na_2SO_4$, filtered and concentrated. The residue was purified by column chromatography (SiO₂, Petroleum ether/Ethyl acetate=80:1 to 20:1) and TLC (Petroleum ether:Ethyl acetate=1:1). Intermediate 7 (110 mg, 160.43 umol, 42.89% yield, 90% purity) was obtained as yellow solid. ¹H NMR (400 MHz, METHANOL-d4) δ ppm 8.00-7.97 (m, 1H), 7.66 (d, J=8.4 Hz, 1H), 7.57 (t, J=7.8 Hz, 1H), 7.48 (d, J=8.3 Hz, 2H), 7.20 (s, 2H), 6.82 (d, J=7.3 Hz, 1H), 6.63 (d, J=8.2 Hz, 1H), 5.42 (s, 2H), 5.30-5.21 (m, 1H), 4.70-4.60 (m, 2H), 4.57 (s, 1H), 4.49 (td, J=5.9, 9.1 Hz, 1H), 4.28 (q, J=7.1 Hz, 2H), 4.03-3.97 (m, 1H), 3.88 (d, J=13.8 Hz, 1H), 3.04 (br d, J=8.9 Hz, 1H), 2.92 (br d, J=11.0 Hz, 1H), 2.86-2.74 (m, 1H), 2.71-2.60 (m, 1H), 2.57-2.47 (m, 1H), 2.38-2.20 (m, 2H), 1.92-1.78 (m, 5H), 1.33 (t, J=7.1 Hz, 3H).

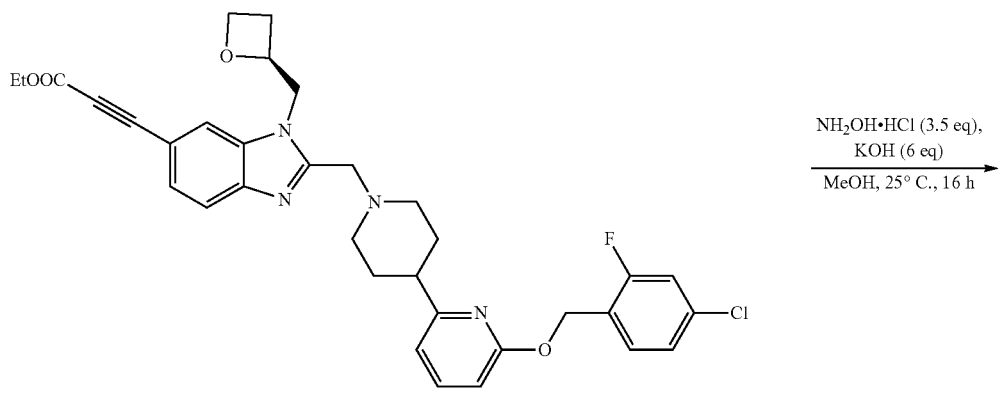

-continued

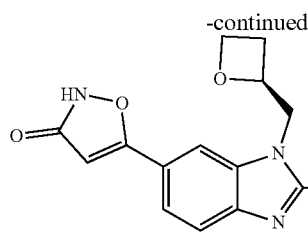

NH$_2$OH·HCl (51.24 mg, 737.31 umol, 3.5 eq) and KOH (94.55 mg, 1.69 mmol, 8 eq) was added to the solution of Intermediate 7 (130 mg, 210.66 umol, 1 eq) in MeOH (6 mL) at 20° C. The solution was stirred at 20° C. for 16 h. The mixture was poured into water (15 mL) and extracted with ethyl acetate (10 mL*3). The combined ethyl acetate was washed with brine (15 mL), dried over Na$_2$SO$_4$, filtered and concentrated. The residue was purified by prep-TLC (Ethyl acetate:Methanol=10:1). Compound 6 (30.46 mg, 48.76 umol, 23.14% yield, 96.69% purity) was obtained as white solid. $^1$H NMR (400 MHz, METHANOL-d$_4$) δ ppm 8.07 (s, 1H), 7.73-7.65 (m, 2H), 7.57 (t, J=7.6 Hz, 1H), 7.49 (t, J=8.0 Hz, 1H), 7.23-7.15 (m, 2H), 6.82 (d, J=7.2 Hz, 1H), 6.63 (d, J=8.2 Hz, 1H), 6.33 (s, 1H), 5.41 (s, 2H), 5.32-5.24 (m, 1H), 4.91 (m, 1H), 4.73 (d, J=15.4 Hz, 1H), 4.67-4.61 (m, 1H), 4.48 (m, 1H), 4.08-4.01 (d, J=13.6 Hz, 1H), 3.95-3.89 (d, J=13.6 Hz, 1H), 3.09 (m, 1H), 2.97 (m, 1H), 2.87-2.76 (m, 1H), 2.70-2.61 (m, 1H), 2.59-2.49 (m, 1H), 2.41-2.26 (m, 2H), 1.94-1.82 (m, 4H). LCMS: RT=2.395 min, MS cal.: 604.0, [M+H]$^+$=604.3.

Example 7

Preparation of Compound 7

Compound 7 was made in an analogous fashion to Compound 1. $^1$H NMR (400 MHz, CDCl$_3$) δ ppm 7.99 (s, 1H), 7.84 (d, J=8.4 Hz, 1H), 7.68 (d, J=8.4 Hz, 1H), 7.42 (t, J=8.0 Hz, 1H), 7.38-7.32 (m, 1H), 7.26-7.21 (m, 2H), 6.16 (m, 2H), 5.35 (s, 2H) 5.25 (m, 1H), 4.81-4.63 (m, 3H), 4.48 (m, 1H), 4.05-3.94 (s, 2H), 3.57-3.43 (m, 4H), 2.86-2.71 (m, 1H), 2.65 (m, 4H), 2.58-2.43 (m, 1H). LCMS: [M+H]+=650.2, 652.2.

Example 8

Preparation of Compound 8

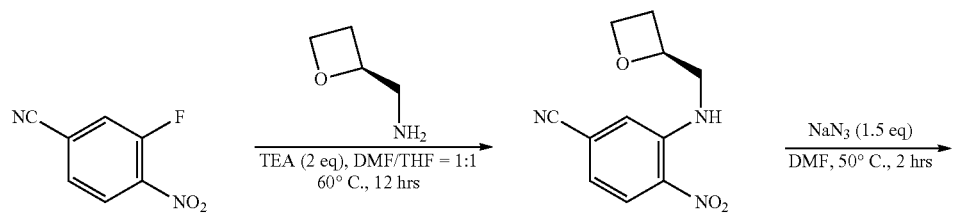

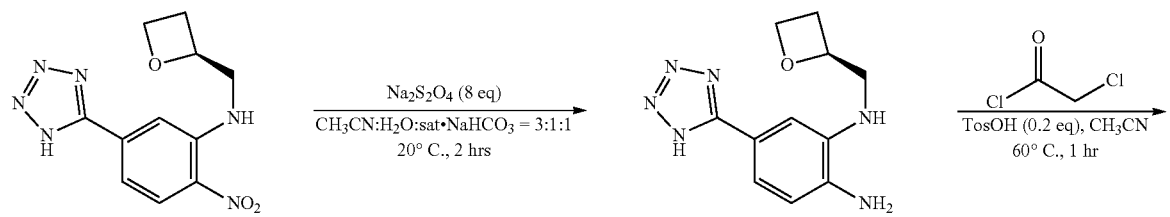

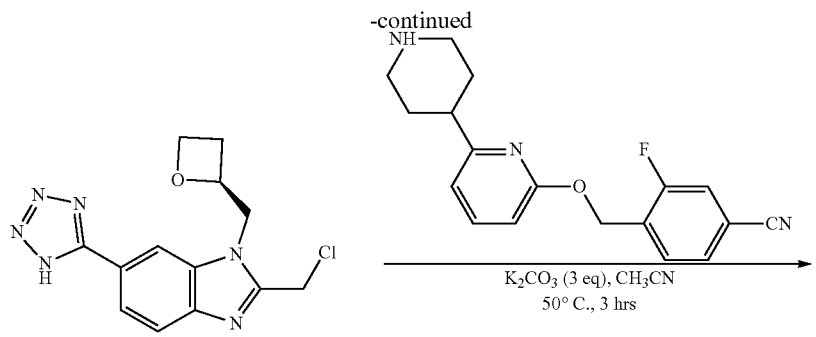

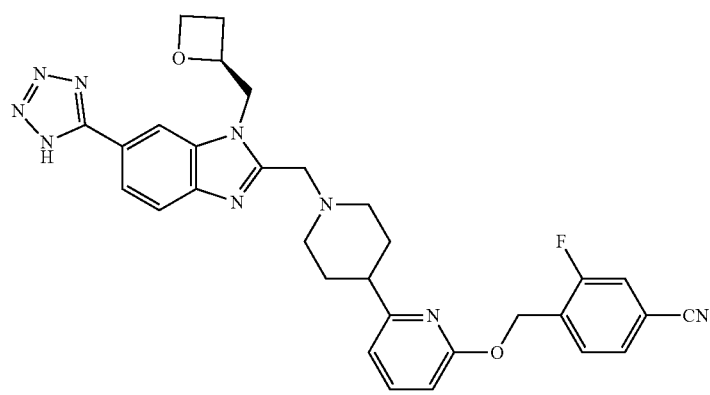

Compound 8 was prepared according to the scheme shown herein. $^1$H NMR (400 MHz, DMSO-d$_6$) δ 8.35 (s, 1H), 7.92-7.84 (m, 2H), 7.80-7.76 (d, J=8.4 Hz, 1H), 7.73-7.70 (m, 2H), 7.68-7.64 (t, J=8.0 Hz, 1H), 6.90 (d, J=8.0 Hz, 1H), 6.74 (d, J=8.0 Hz, 1H), 5.48 (s, 2H), 5.20-5.12 (m, 1H), 4.86-4.77 (m, 1H), 4.72-4.65 (m, 1H), 4.55-4.47 (m, 1H), 4.43 (m, 1H), 4.07-4.00 (d, J=13.6 Hz, 1H), 3.91-3.84 (d, J=13.6 Hz, 1H), 3.06 (m, 1H), 2.98-2.89 (m, 1H), 2.76-2.67 (m, 2H), 2.44 (m, 1H), 2.34-2.21 (m, 2H), 1.82-1.69 (m, 4H). LCMS: [M+H]$^+$=580.2

Example 9

Preparation of Compound 9

Compound 9 was prepared according to the methods disclosed herein. $^1$H NMR (400 MHz, MeOD) δ ppm 8.93 (s, 1H), 7.84 (s, 1H), 7.71-7.64 (t, J=7.2 Hz, 1H), 7.62-7.52 (m, 3H), 7.45 (s, 1H), 7.40-7.37 (s, 1H), 6.80 (d, J=7.2 Hz, 1H), 6.67 (d, J=8.0 Hz, 1H), 5.87 (s, 2H), 5.51 (s, 2H), 3.75 (s, 2H), 3.53-3.46 (d, J=2.0 Hz, 2H), 2.98-2.90 (m, 2H), 2.66-2.53 (m, 1H), 2.25-2.16 (m, 2H), 1.80-1.62 (m, 4H). LCMS: [M+H]$^+$=598.2

Example 10

Preparation of Compound 10

Compound 10 was made in an analogous fashion to Compound 8. WO 2022/040600, which is incorporated herein by references, is also instructive in the preparation of Compound 10. $^1$H NMR (400 MHz, DMSO-d$_6$) δ ppm 8.90 (s, 1H), 8.19 (s, 1H), 7.98 (s, 1H), 7.88 (m, 2H), 7.75 (d, J=8.4 Hz, 1H), 7.71-7.59 (m, 4H), 6.92 (d, J=7.2 Hz, 1H), 6.65 (d, J=8.0 Hz, 1H), 5.91 (s, 2H), 5.41 (s, 2H), 3.88 (d, J=13.6 Hz, 1H), 3.77 (d, J=13.6 Hz, 1H), 2.89-2.65 (m, 2H), 2.43-2.33 (m, 3H), 1.94-1.85 (m, 1H), 1.65 (m, 1H), 1.04 (m, 1H), 0.79 (m, 1H). LCMS: [M+H]$^+$=619.1

Example 11

Preparation of Compound 11

Compound 11 was made in an analogous fashion to Compound 8. $^1$H NMR (400 MHz, MeOD) δ ppm 8.94 (s, 1H), 8.25 (s, 1H), 8.05 (s, 1H), 8.03-8.00 (dd, J=8.4, 1.2 Hz, 1H), 7.80 (d, J=8.4 Hz, 1H), 7.70 (t, J=8.0 Hz, 1H), 7.65-7.54 (m, 3H), 6.85 (d, J=7.2 Hz, 1H), 6.70 (d, J=8.0 Hz, 1H), 6.05 (s, 2H), 5.54 (s, 2H), 4.03 (s, 2H), 3.17-3.09 (m, 2H), 2.74-2.62 (m, 1H), 2.47-2.35 (m, 2H), 1.90-1.79 (m, 4H). LCMS: [M+H]$^+$=607.4

Example 12
Preparation of Compound 12
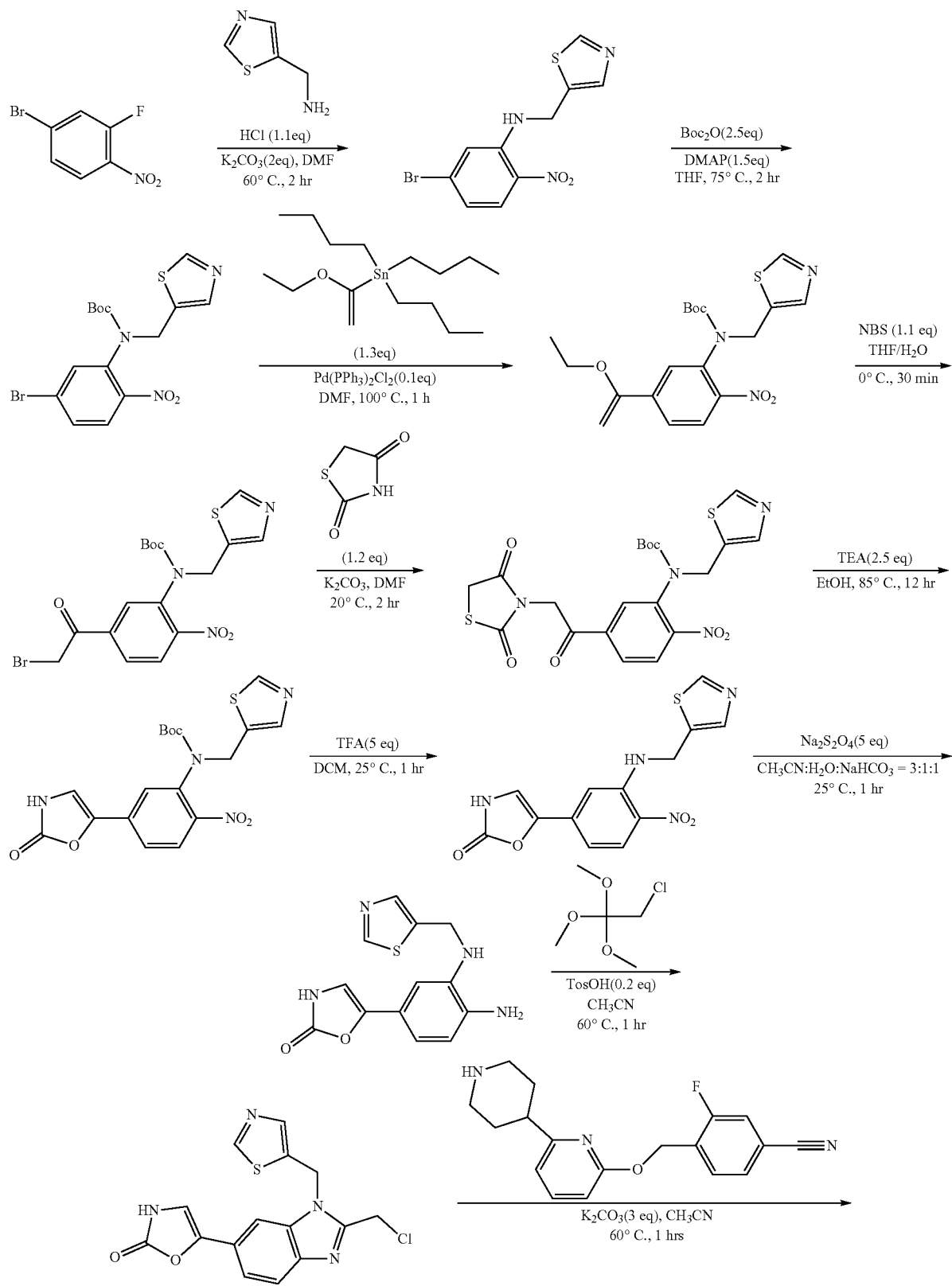

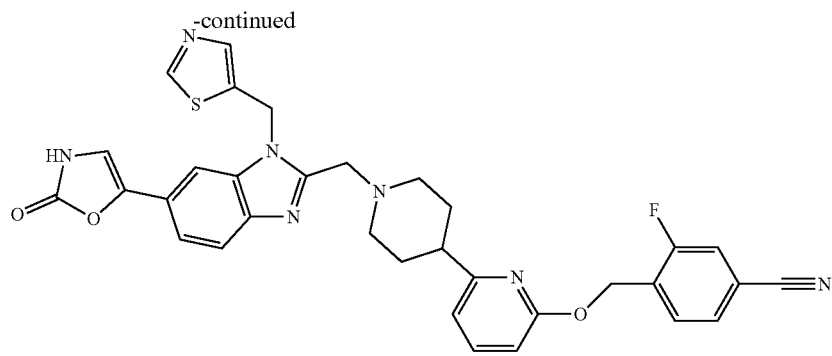

Compound 12 was prepared according to the scheme shown herein. $^1$H NMR (400 MHz, DMSO-$d_6$) δ ppm 10.75 (br s, 1H), 8.97 (s, 1H), 8.04 (s, 1H), 7.88 (d, J=10.0 Hz, 1H), 7.72-7.69 (m, 2H), 7.67 (s, 2H), 7.64-7.60 (t, J=17.30, 8.86 Hz, 3H), 7.45 (s, 1H), 7.39 (d, J=8.4 Hz, 1H), 6.86 (d, J=7.2 Hz, 1H), 6.71 (d, J=8.0 Hz, 1H), 5.90 (s, 2H), 5.47 (s, 2H), 3.83 (s, 2H), 3.29 (s, 1H), 2.94 (m, 2H), 2.64-2.55 (m, 1H), 2.22-2.13 (m, 2H), 1.78-1.60 (m, 4H). LCMS [M+H]$^+$=622.1.

Example 13

Preparation of Compound 13

Compound 13 was made in an analogous fashion to Compound 5. $^1$H NMR (400 MHz, DMSO-$d_6$) δ ppm 8.98 (s, 1H), 8.08 (s, 1H), 8.03 (s, 1H), 7.91-7.86 (d, J=6.4 Hz, 1H), 7.78-7.74 (d, J=8.4 Hz, 1H), 7.73-7.69 (m, 3H), 7.68-7.63 (t, J=8.0 Hz, 1H), 6.87 (d, J=7.2 Hz, 1H), 6.72 (d, J=8.0 Hz, 1H), 5.98 (s, 2H), 5.48 (s, 2H), 3.88 (s, 2H), 2.97 (m, 2H), 2.65-2.54 (m, 1H), 2.26-2.15 (m, 2H), 1.79-1.62 (m, 4H). LCMS: [M+H]$^+$=623.4.

Example 14

Preparation of Compound 14

Compound 14 was made in an analogous fashion to Compound 1. $^1$H NMR (400 MHz, MeOD) δ ppm 8.07 (s, 1H), 7.71-7.65 (m, 3H), 7.63-7.52 (m, 3H), 6.84 (d, J=7.2 Hz, 1H), 6.69 (d, J=8.0 Hz, 1H), 5.52 (s, 2H), 5.32-5.25 (m, 1H), 4.91 (m, 1H), 4.71 (m, 1H), 4.68-4.62 (m, 1H), 4.49 (m, 1H), 4.11-4.06 (d, J=13.6 Hz, 1H), 3.98-3.92 (d, J=13.6 Hz, 1H), 3.11 (, 1H), 2.98 (m, 1H), 2.87-2.77 (m, 1H), 2.71-2.61 (m, 1H), 2.49-2.60 (m, 1H), 2.45-2.29 (m, 2H), 1.91-1.78 (m, 4H). LCMS: [M+H]$^+$=571.1.

Example 15

Preparation of Compound 15

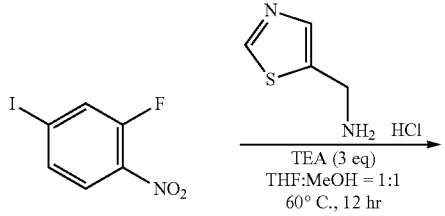

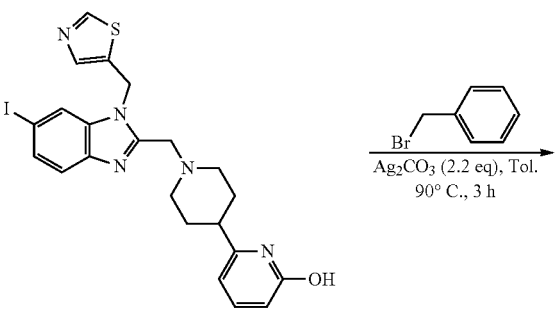

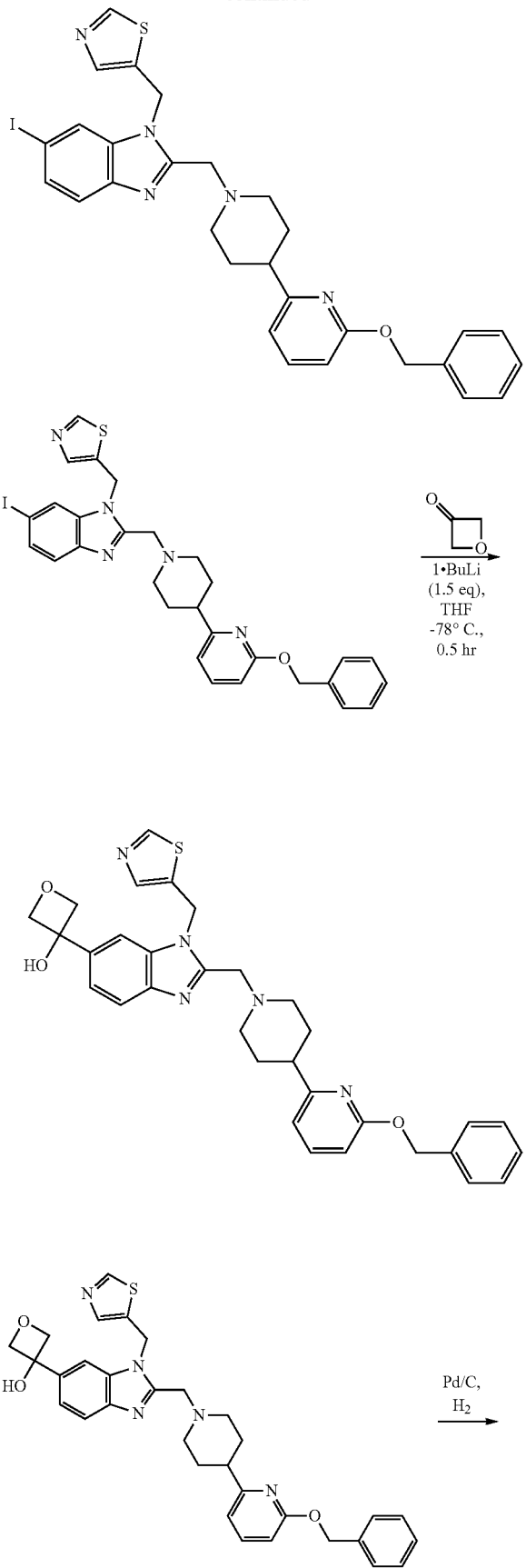
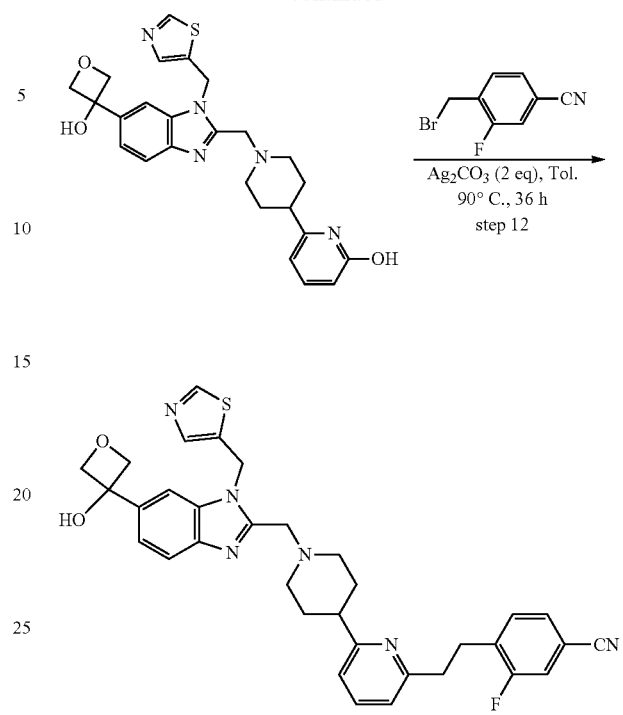
Compound 15 was prepared according to the scheme shown herein. $^1$H NMR (400 MHz, DMSO-$d_6$) δ ppm 8.96 (s, 1H), 8.01 (s, 1H), 7.88 (d, J=9.6 Hz, 1H), 7.77 (s, 1H), 7.72-7.68 (m, 2H), 7.67-7.60 (m, 2H), 7.46 (dd, J=8.4, 1.6 Hz, 1H), 6.86 (d, J=7.2 Hz, 1H), 6.71 (d, J=8.0 Hz, 1H), 6.37 (br s, 1H), 5.90 (s, 2H), 5.47 (s, 2H), 4.81-4.78 (d, J=6.4 Hz, 2H), 4.74 (d, J=6.4 Hz, 2H), 3.84 (s, 2H), 2.94 (m, 2H), 2.62-2.54 (m, 1H), 2.22-2.14 (m, 2H), 1.76-1.61 (m, 4H). LCMS: [M+H]$^+$=611.20.
Example 16
Preparation of Compound 16
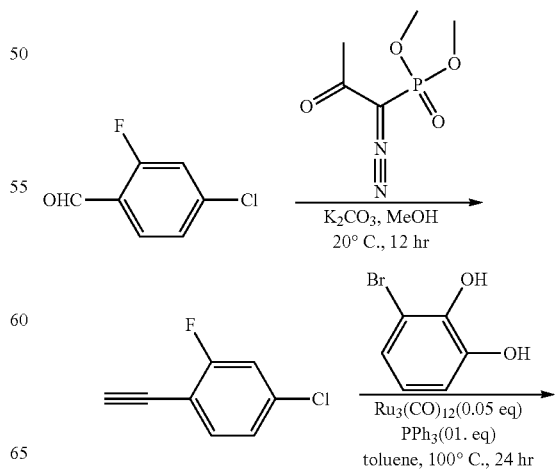

-continued

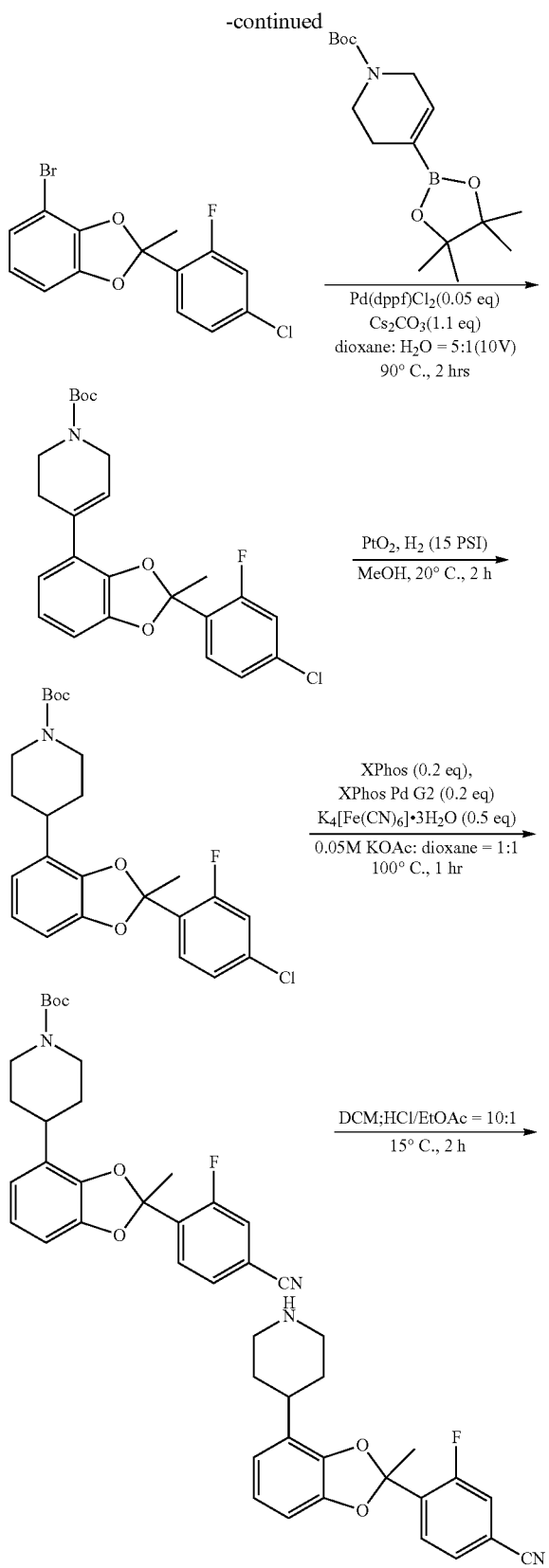

Aside from this intermediate, Compound 16 was made in an analogous fashion to Compound 8. $^1$H NMR (400 MHz, MeOD) δ ppm 8.12 (s, 1H), 7.86 (d, J=8.4 Hz, 1H), 7.70-7.62 (m, 2H), 7.52 (d, J=10.4 Hz, 1H), 7.44 (dd, J=8.0, 1.2 Hz, 1H), 6.73-6.66 (t, J=8.0 Hz, 1H), 6.65-6.59 (m, 2H), 5.22-5.12 (m, 1H), 4.57-4.51 (m, 2H), 4.40-4.35 (m, 1H), 4.30-4.25 (m, 2H), 3.42-3.26 (m, 2H), 2.81-2.65 (m, 4H), 2.52-2.38 (m, 1H), 1.98 (s, 3H), 1.91-1.83 (m, 4H). LCMS [M+H]$^+$=607.2.

Example B1

Biological Activity of the Compounds of the Present Disclosure

The biological activity of the compounds of the present disclosure was determined utilizing the assays described herein.

The $EC_{50}$ values of exemplary compounds in the low expression assay are shown in Table B1 below. The compounds tested were compound samples prepared according to the General Procedures described in the Examples section.

TABLE B1

| Compound No. | GLP1 $EC_{50}$ (nM) |
|---|---|
| 3 | 5938 |
| 4 | 231 |
| 5 | 45.4 |
| 6 | 10.6 |
| 7 | 148 |
| 8 | 14.986 |
| 9 | 460.91 |
| 10 | 117.55 |
| 11 | 53.247 |
| 12 | 704.26 |
| 13 | 25.154 |
| 14 | 49.991 |
| 15 | >10000 |
| 16 | 2.6796 |

Example B2

Rat Pharmacokinetics

Intravenous dosing: Compounds were formulated at 0.5 mg/mL in a solution comprising 5% polyethylene glycol 400 and 95% (12% (w/v) sulfobutyl-β-cyclodextrin in water) (v/v). Formulated compounds were sterile filtered through a 0.22 micron filter before dosing. Compounds were administered to male, 7-11-week-old Sprague-Dawley rats by jugular vein cannula infusion over 30 minutes at a dose of 1 mg/kg.

Oral dosing: Compounds were formulated at 0.3 mg/mL or 0.6 mg/mL in a solution comprising 5% polyethylene glycol 400 and 95% (12% (w/v) sulfobutyl-β-cyclodextrin in water) (v/v). Formulated compounds were administered to male, 7-11-week-old Sprague-Dawley rats by oral gavage at a dose of 10 mL/kg.

Sample collection: Blood collections of about 0.2 mL per time point were performed from jugular vein or other suitable site of each animal, into pre-chilled commercial EDTA-K2 tubes and placed on wet ice until centrifugation. Blood samples were processed for plasma by centrifugation at approximately 4° C., 3,200 g for 10 min. Plasma was collected and transferred into pre-labeled 96 well plate or polypropylene tubes, quick frozen over dry ice and kept at −60° C. or lower until LC-MS/MS analysis.

Data analysis: Plasma concentration versus time data was plotted in graph and analyzed by non-compartmental analysis approaches using the Phoenix WinNonlin 6.3 software program, or higher builds. Related PK parameters were calculated according to dosing route, e.g., CL, $V_{dss}$ and $C_0$ for intravenous administration, $C_{max}$, $T_{max}$ or % F for extravascular administration, and $T_{1/2}$, $AUC_{(0-t)}$, $AUC_{(0-inf)}$, $MRT_{(0-t)}$, $MRT_{(0-inf)}$ for all routes.

TABLE B2

| Compound No. | Rat $AUC_{0-t}$ | Rat $C_{max}$ | Rat $T_{1/2}$ |
|---|---|---|---|
| 13 | 102 | 171 ± 165 | 1.58 ± 1.03 |

Example B3

Metabolic Stability in Hepatocytes

Test compounds were incubated in rat and human hepatocytes and stability was assessed from the substrate depilation approach. Test compounds were dissolved in dimethyl sulfoxide (DMSO) to create a 10 mM Stock, and then further diluted to create a 1000×Working Stock of 1 mM with DMSO in 96-well plates for test compounds and the positive control (midazolam). Vials containing cryopreserved hepatocytes were removed from the liquid nitrogen tank and immediately immersed in a 37° C. water bath. The vials were shaken gently until the contents had thawed and were then immediately emptied into 48 mL of pre-warmed HT Medium in a 50 mL conical tube. Cells remaining in the vial were resuspended with 1.0 mL of pre-warmed HT Medium and added to the conical tube. The tube was capped and then gently inverted several times to resuspend the hepatocytes. The cell suspension was centrifuged at 50×g at room temperature for 5 minutes and the supernatant discarded. The cell pellet was loosened by gently swirling the centrifuge tube and was re-suspended in 4 mL of warm Dulbecco's Modified Eagle medium (DMEM). Cell density was determined by a cell counter by Nexcelom, and DMEM medium was added to obtain a target density of 1×106 cells/mL. The assay was carried out in 96-well microtiter plates. Test Compounds were incubated at 1 µM with 1×10^6 cells/mL hepatocytes in DMEM for 0, 30, 60, 120 and 240 minutes. The incubation was carried out with gentle shaking at 37° C. under a humid atmosphere of 95% air/5% $CO_2$. The volume of the incubation mixture was 37 µL with a final 0.1% DMSO. At each of the time points, the incubation was stopped by adding 150 µL quenching solution (100% acetonitrile, 0.1% formic acid containing bucetin as an internal standard for positive ESI mode). Subsequently, the mixtures were vortexed for 20 min and centrifuged at 4,000 RPM at 10° C. The supernatant (80 µL) was transferred to a clean 96-well plate and analyzed by LC-MS/MS. Midazolam at 1 µM with a final 0.1% DMSO was included as a positive control to verify assay performance. The percent parent remaining, intrinsic and predicted hepatic clearance and $t_{1/2}$ were calculated. All samples were analyzed by LC-MS/MS using an AB Sciex API 4000 instrument, coupled to a Shimadzu LC-20AD LC Pump system. Separation was achieved using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed below.

| Time (min) | Flow (µL/min) | % A | % B |
|---|---|---|---|
| 0 | 500 | 98 | 2 |
| 0.30 | 500 | 98 | 2 |
| 1.40 | 500 | 2 | 98 |
| 2.20 | 500 | 2 | 98 |
| 2.21 | 500 | 98 | 2 |
| 3.00 | 500 | 98 | 2 |

The ion optics of each test compound were optimized for their declustering potential (DP), collection energy (CE), collision-cell exit potential (CXP) and used in a selected ion monitoring experiment in the positive ion mode. The peak area ratio of each test compound to internal standard was then evaluated for stability. The extent of metabolism was calculated based on the disappearance of the test compound, compared to its initial concentration. The initial rates of clearance of the test compound were calculated using the linear regression plot of semi-log % remaining of the compound versus time. The elimination rate constant (k) of the linear regression plot was then used to determine $t_{1/2}$ and the intrinsic clearance ($CL_{int}$) using the following formula, where $C_{hepatocyte}$ (million cells/mL) is the cell density of the incubation:

$$k = -\text{slope}$$

$$t_{1/2} = 0.693/k$$

$$CL_{int} = k/C_{hepatocyte}$$

This method of intrinsic clearance determination assumes that the test compound concentration is far below the Michaelis-Menten constant of the compound to its metabolizing enzymes.

The predicted hepatic clearance ($CL_{hep}$) was calculated using the well stirred method with the following formula with $CL_{int(in\ vivo)}$ normalized based on liver weight:

$$CL_{int(in\ vivo)} = CL_{int} \times \text{Hepatocellularity} \times \text{liver weight}$$

$$CL_{hep\ predicted} = (CL_{int(in\ vivo)} \times Q_{liver})/(CL_{int(in\ vivo)} + Q_{liver})$$

Where $Q_{liver}$ ((ml/min/kg) is Liver Blood Flow

The relevant physiological parameters of liver weight, blood flow, and hepatocellularity for various species are listed below:

| Species | Liver Weight (g liver/kg body weight) | Hepatocellularity (106 cells/g liver) | Liver Blood Flow ($Q_{liver}$, mL/min/kg) |
|---|---|---|---|
| Human | 25.7 | 135 | 20.7 |
| Rat | 40 | 120 | 55.2 |

Results are presented in the Table B3 below for the intrinsic clearance (mL/min/kg) and half-life (t1/2).

TABLE B3

| Compound No. | Human CLint (mL/min/kg) | Human $T_{1/2}$ (min) | Rat CLint (mL/min/kg) | Rat $T_{1/2}$ (min) |
| --- | --- | --- | --- | --- |
| 8 | 7.99 ± 0.99 | 301.04 ± 37.39 | 46.53 ± 2.11 | 71.49 ± 3.24 |
| 11 | 19.71 ± 0.4 | 122.01 ± 2.46 | 68.26 ± 2.52 | 48.73 ± 1.8 |
| 13 | 35.84 ± 1.06 | 67.09 ± 1.99 | 110.59 ± 2.29 | 30.08 ± 0.62 |
| 16 | 6.22 ± 0.55 | 386.5 ± 34.27 | 6.93 ± 0 | 480 ± 0 |

Example B4

Passive Permeability and Efflux Ratio

Caco-2 cells (clone C2BBe1) were obtained from American Type Culture Collection (Manassas, VA). Cell monolayers were grown to confluence on collagen-coated, microporous membranes in 12-well assay plates. Details of the plates and their certification are shown below. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 µM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. The flux of lucifer yellow was also measured post-experimentally for each monolayer to ensure no damage was inflicted to the cell monolayers during the flux period. All samples were assayed by LC-MS/MS using electrospray ionization. The apparent permeability ($P_{app}$) and percent recovery were calculated as follows:

$$P_{app} = (dC_r/dt) \times V_r/(A \times C_A) \quad (1)$$

$$\text{Percent Recovery} = 100 \times ((V_r \times C_r^{final}) + (V_d \times C_d^{final}))/(V_d \times C_N) \quad (2),$$

where, $dC_r/dt$ is the slope of the cumulative receiver concentration versus time in µM $s^{-1}$; $V_r$ is the volume of the receiver compartment in $cm^3$; $V_d$ is the volume of the donor compartment in $cm^3$; A is the area of the insert (1.13 $cm^2$ for 12-well); $C_A$ is the average of the nominal dosing concentration and the measured 120-minute donor concentration in µM; $C_N$ is the nominal concentration of the dosing solution in µM; $C_r^{final}$ is the cumulative receiver concentration in µM at the end of the incubation period; $C_d^{final}$ is the concentration of the donor in µM at the end of the incubation period. Efflux ratio (ER) is defined as $P_{app}$ (B-to-A)/$P_{app}$ (A-to-B).

TABLE B4

| Compound # | $P_{app}$ (A-to-B) | $P_{app}$ (B-to-A) |
| --- | --- | --- |
| 8 | 1.8 | 18.8 |
| 13 | 46.9 | 51.1 |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of formula (I):

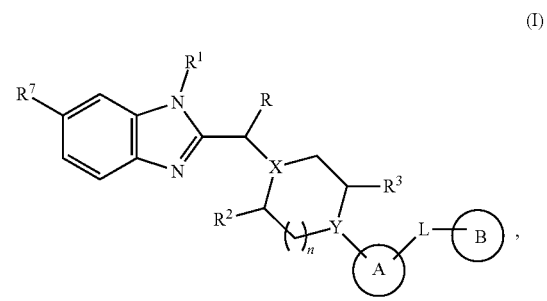

or a pharmaceutically acceptable salt thereof, wherein:
X is N or CH;
Y is N or $CR^4$;
n is 0 or 1;
R is hydrogen;
$R^1$ is —$C_1$-$C_6$ alkylene-$R^5$;
$R^2$ is hydrogen, oxo, or $C_1$-$C_6$ alkyl;
$R^3$ is hydrogen, oxo, or $C_1$-$C_6$ alkyl and $R^4$ is hydrogen, OH or $C_1$-$C_6$ alkyl,
or $R^3$ and $R^4$ are taken together with the carbon atoms to which they are attached to form $C_3$-$C_6$ cycloalkyl optionally substituted by halo or $C_1$-$C_3$ alkyl;
$R^5$ is 5 to 6-membered heteroaryl optionally substituted by halo, $C_1$-$C_6$ alkyl, $C_1$-$C_6$ alkoxy, $C_1$-$C_6$ alkenyl, or $C_1$-$C_6$ haloalkyl;
$R^7$ is selected from the group consisting of

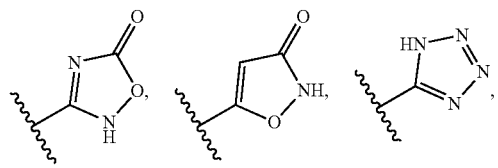

-continued

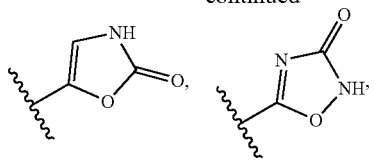

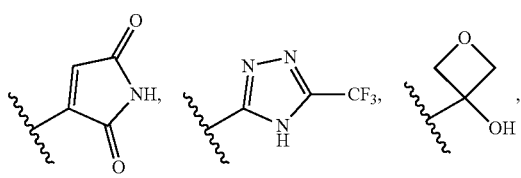

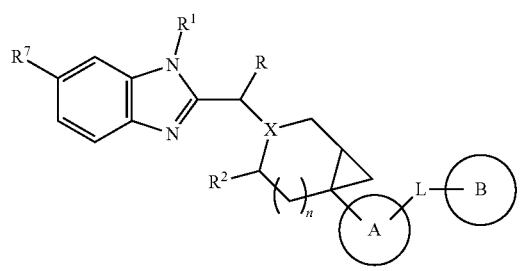

or $R^7$ is —C(O)NH—$R^8$, wherein $R^8$ is hydrogen, —OH, —S(O)$_2$—C$_1$-C$_6$ alkyl, or —C$_1$-C$_6$ alkyl optionally substituted by halo;

Ring A is 5- to 12-membered heterocyclyl, 5- to 12-membered heteroaryl, or C$_6$-C$_{14}$ aryl, each of which is independently optionally substituted by halo, oxo, —CN, C$_3$-C$_6$ cycloalkyl, or C$_1$-C$_6$ alkyl optionally substituted by halo or OH;

L is a bond, —O—, C$_1$-C$_6$ alkylene, *—O—C$_1$-C$_6$ alkylene-**, *—C$_1$-C$_6$ alkylene-O—**, or *-NR$^6$—C$_1$-C$_6$ alkylene-**, wherein:

* represents the point of attachment to ring A and ** represents the point of attachment to ring B;

when L is *—O—C$_1$-C$_6$ alkylene-**, the C$_1$-C$_6$ alkylene is optionally substituted by $R^L$, wherein each $R^L$ is independently C$_1$-C$_6$ alkyl or halo, or two $R^L$ are taken together with the carbon atom or atoms to which they are attached to form C$_3$-C$_6$ cycloalkyl or 3- to 6-membered heterocyclyl; and when L is C$_1$-C$_6$ alkylene, the C$_1$-C$_6$ alkylene is optionally substituted by $R^{L1}$, wherein each $R^{L1}$ is independently halo, OH, oxo, or C$_1$-C$_6$ alkyl, or two $R^{L1}$ are taken together with the carbon atom or atoms to which they are attached to form C$_3$-C$_6$ cycloalkyl or 3- to 6-membered heterocyclyl;

$R^6$ is hydrogen or C$_1$-C$_6$ alkyl; and

Ring B is C$_3$-C$_{10}$ cycloalkyl, C$_6$-C$_{14}$ aryl, 4- to 12-membered heterocyclyl, or 5- to 12-membered heteroaryl, each of which is independently optionally substituted by one to three substituents independently selected from the group consisting of halo, CN, oxo, C$_1$-C$_6$ alkyl, C$_1$-C$_6$ haloalkyl, —C(O)CH$_3$, —C(O)NH$_2$, —S(O)$_2$CH$_3$, cyclopropyl, and phenyl.

2. The compound of claim 1, wherein the compound is of Formula I-s:

(I-s)

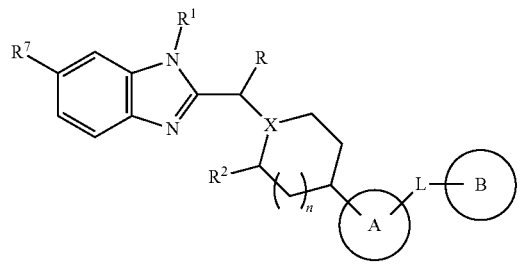

or a pharmaceutically acceptable salt thereof.

3. The compound of claim 1, wherein the compound is of Formula I-t:

(I-t)

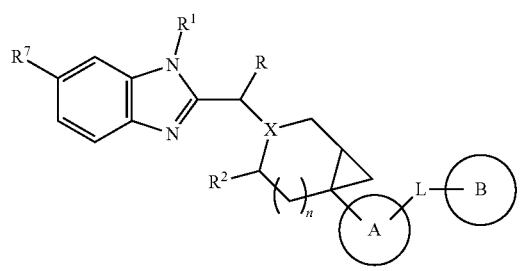

or a pharmaceutically acceptable salt thereof.

4. The compound of claim 1, wherein:
n is 1;
X is N;
$R^2$ is hydrogen;
$R^5$ is an optionally substituted five-membered heteroaryl comprising one or two heteroatoms selected from the group consist of oxygen, nitrogen, and sulfur;
$R^7$ is

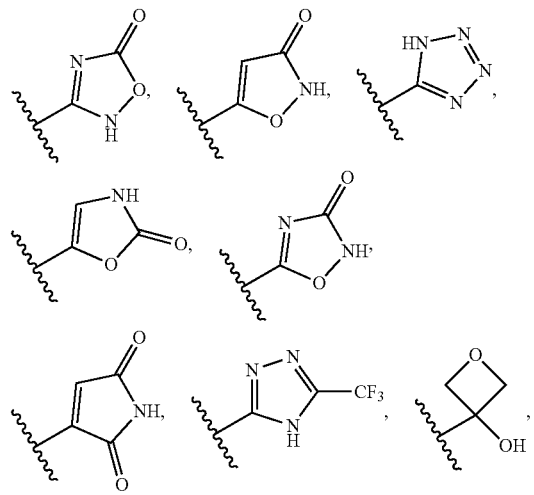

C(O)NHCH$_3$, [H]C(O)NH$_2$, C(O)NHCH$_2$CF$_3$, C(O)NHS(O)$_2$CH$_3$, or C(O)NHOH;

Ring A is an optionally substituted 6-9-membered heteroaryl;

L is a bond or *—O—CH$_2$—**;

Ring B is phenyl optionally substituted by one to three substituents independently selected from the group consisting of halo and cyano.

5. The compound of claim 1, or a pharmaceutically acceptable salt thereof, wherein R$^1$ is —CH$_2$—R$^5$.

6. The compound of claim 1, or a pharmaceutically acceptable salt thereof, wherein R$^5$ is 5-membered heteroaryl optionally substituted by halo, C$_1$-C$_6$ alkyl, C$_1$-C$_6$ alkoxy, C$_1$-C$_6$ alkenyl, or C$_1$-C$_6$ haloalkyl.

7. The compound of claim 2, or a pharmaceutically acceptable salt thereof, wherein R$^5$ is:

(i)

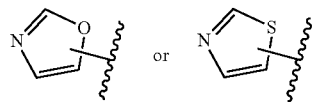

optionally substituted by halo, C$_1$-C$_6$ alkyl, C$_1$-C$_6$ alkoxy, C$_1$-C$_6$ alkenyl, or C$_1$-C$_6$ haloalkyl.

8. The compound of claim 1, or a pharmaceutically acceptable salt thereof, wherein:

X is N; and n is 1.

9. The compound of claim 8, or a pharmaceutically acceptable salt thereof, wherein R$^3$ and R$^4$ are taken together with the carbon atoms to which they are attached to form a cyclopropyl group.

10. The compound of claim 1, or a pharmaceutically acceptable salt thereof, wherein R$^7$ is selected from the group consisting of

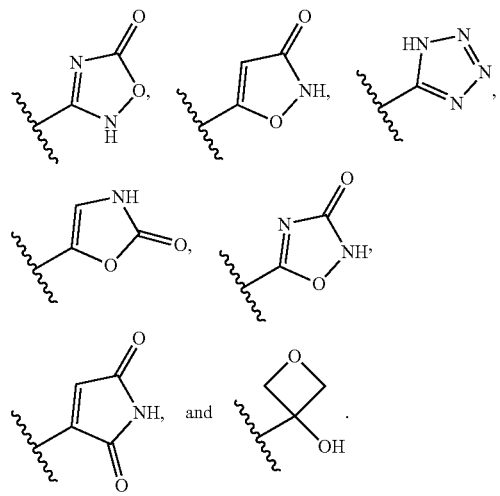

11. The compound of claim 1, or a pharmaceutically acceptable salt thereof, wherein R$^7$ is —C(O)NH—R$^8$.

12. The compound of claim 1, or a pharmaceutically acceptable salt thereof, wherein R$^8$ is:

(i) hydrogen;

(ii) —OH;

(iii) —S(O)$_2$—C$_1$-C$_6$ alkyl; or (iv) —C$_1$-C$_6$ alkyl optionally substituted by halo.

13. The compound of claim 12, or a pharmaceutically acceptable salt thereof, wherein R$^8$ is:

(i) —S(O)$_2$CH$_3$; or (ii) —C$_1$-C$_2$ alkyl, each of which is independently optionally substituted by halo.

14. The compound of claim 1, or a pharmaceutically acceptable salt thereof, wherein R$^8$ is —CH$_2$CF$_3$ or —CH$_3$.

15. The compound of claim 1, or a pharmaceutically acceptable salt thereof, wherein Ring A is 6-membered heteroaryl or 9-membered heteroaryl.

16. The compound of claim 1, or a pharmaceutically acceptable salt thereof, wherein Ring A is

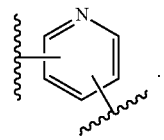

17. The compound of claim 1, or a pharmaceutically acceptable salt thereof, wherein Ring A is:

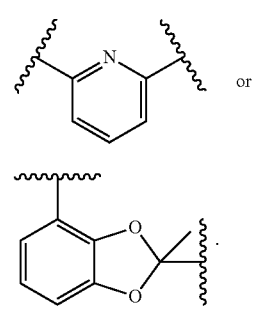

18. The compound of claim 1, or a pharmaceutically acceptable salt thereof, wherein L is *—O—C$_1$-C$_6$ alkylene-**.

19. The compound of claim 1, or a pharmaceutically acceptable salt thereof, wherein L is *—O—CH$_2$—**.

20. The compound of claim 1, or a pharmaceutically acceptable salt thereof, wherein Ring B is C$_6$ aryl, which is optionally substituted by one to three substituents independently selected from the group consisting of halo and CN.

21. The compound of claim 1, or a pharmaceutically acceptable salt thereof, wherein Ring B is C$_6$ aryl, which is optionally substituted by one to three substituents independently selected from the group consisting of —F, —Br, and —CN.

22. The compound of claim 1, or a pharmaceutically acceptable salt thereof, wherein Ring B is

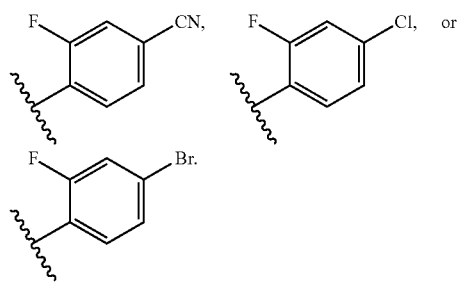

23. A compound selected from the group consisting of,
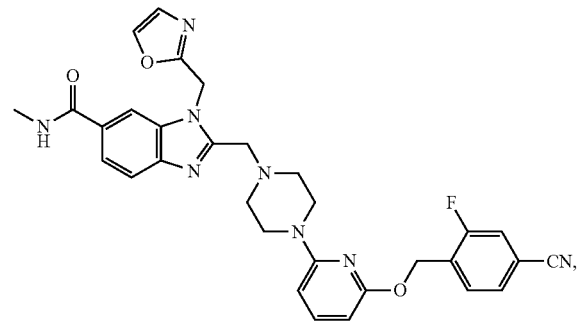
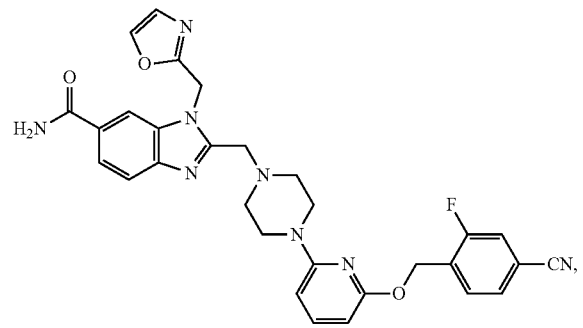
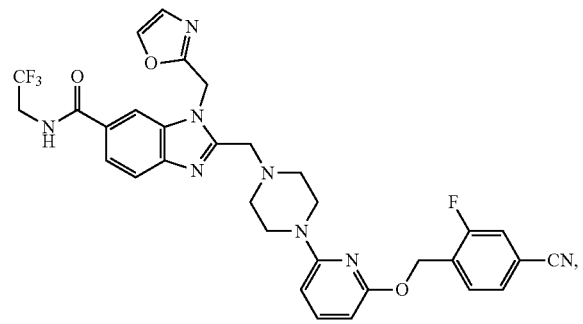
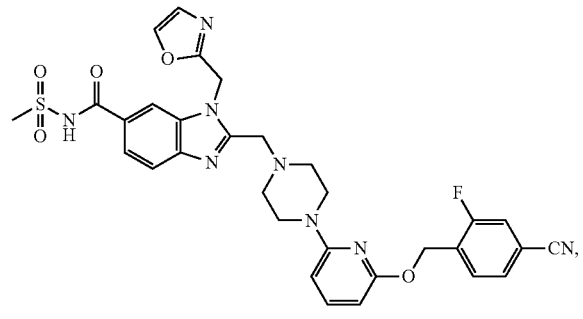
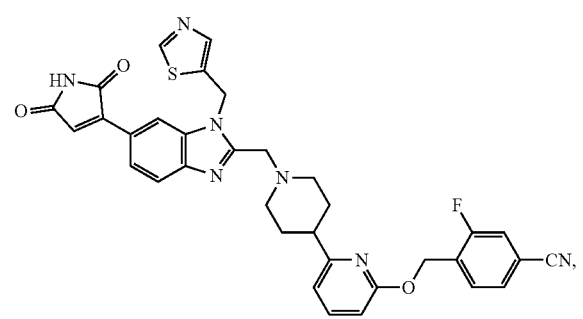
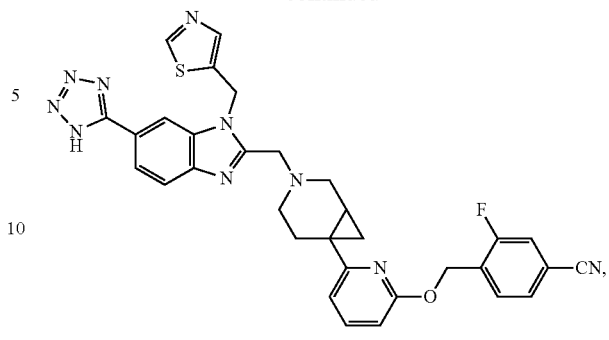
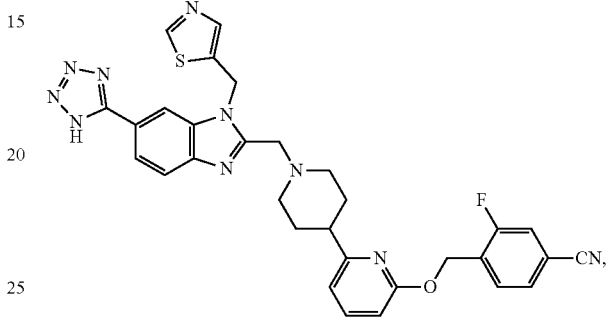
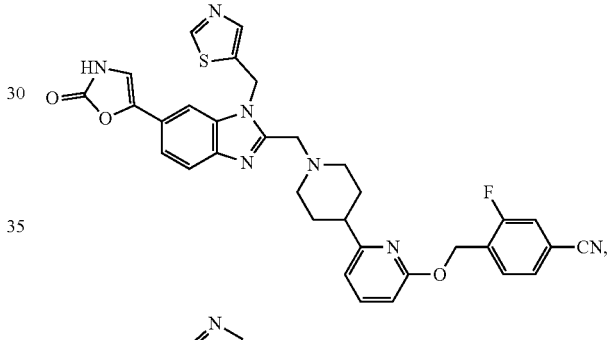
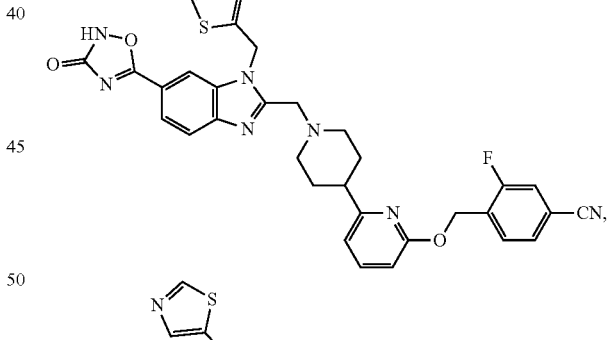
or a pharmaceutically acceptable salt thereof.

24. A pharmaceutical composition comprising the compound of claim 1, or a pharmaceutically acceptable salt thereof, and a pharmaceutically acceptable excipient.

25. A method of treating a disease mediated by glucagon-like peptide-1 receptor (GLP-1R) in an individual in need thereof, comprising administering to the individual a therapeutically effective amount of the compound of claim 1, or a pharmaceutically acceptable salt thereof.

26. The method of claim 25, wherein the disease is a liver disease.

27. The method of claim 26, wherein the liver disease is primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, or oti-antitrypsin deficiency.

28. The method of claim 25, wherein the disease is diabetes or a cardiometabolic disease.

29. A pharmaceutical composition comprising the compound of claim 23, or a pharmaceutically acceptable salt thereof, and a pharmaceutically acceptable excipient.

30. The compound of claim 1, or a pharmaceutically acceptable salt thereof, wherein $R^5$ is

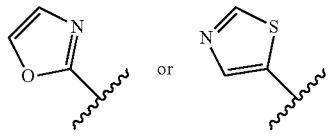 [SMILES: *c1ncco1 ; *c1cncs1]

optionally substituted by halo $C_1$-$C_6$ alkyl, $C_1$-$C_6$ alkoxy, $C_1$-$C_6$ alkenyl, or $C_1$-$C_6$ haloalkyl.

31. The compound of claim 1, or a pharmaceutically acceptable salt thereof, wherein $R^5$ is

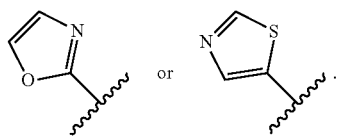 [SMILES: *c1ncco1 ; *c1cncs1]

32. The method of claim 25, wherein the disease is obesity.

* * * * *